United States Patent
Bennett et al.

(10) Patent No.: US 7,272,525 B2
(45) Date of Patent: Sep. 18, 2007

(54) PORTABLE FLUID SENSING DEVICE AND METHOD

(75) Inventors: James Bennett, Santa Clara, CA (US); G. Cameron Dales, Saratoga, CA (US); John M. Feland, III, Palo Alto, CA (US); Oleg Kolosov, San Jose, CA (US); Eric Low, Berkeley, CA (US); Leonid Matsiev, San Jose, CA (US); William C. Rust, Mountain View, CA (US); Mikhail Spitkovsky, Sunnyvale, CA (US); Mark Uhrich, Redwood City, CA (US)

(73) Assignee: Visyx Technologies, Inc., Sunnyvale, CA (US)

( * ) Notice: Subject to any disclaimer, the term of this patent is extended or adjusted under 35 U.S.C. 154(b) by 0 days.

(21) Appl. No.: 11/111,846

(22) Filed: Apr. 20, 2005

(65) Prior Publication Data

US 2006/0031030 A1 Feb. 9, 2006

Related U.S. Application Data

(60) Provisional application No. 60/564,371, filed on Apr. 21, 2004.

(51) Int. Cl.
  *G01F 25/00* (2006.01)
  *G01L 27/00* (2006.01)
  *G01N 11/00* (2006.01)

(52) U.S. Cl. ......................... 702/100; 702/50

(58) Field of Classification Search .............. 702/45, 702/50, 100; 73/861.19, 861.24
See application file for complete search history.

(56) References Cited

U.S. PATENT DOCUMENTS

| | | |
|---|---|---|
| 5,586,445 A | 12/1996 | Bessler |
| 5,708,191 A | 1/1998 | Greenwood et al. |
| 5,741,961 A | 4/1998 | Martin et al. |
| 5,886,250 A | 3/1999 | Greenwood et al. |
| 6,044,694 A | 4/2000 | Anderson et al. |
| 6,082,180 A | 7/2000 | Greenwood |

(Continued)

FOREIGN PATENT DOCUMENTS

DE   100 50 299 A1   4/2002

(Continued)

OTHER PUBLICATIONS

Brand, Oliver; "Micromachined Viscosity Sensor for Real-Time Polymerization Monitoring", 1997 International Conference on Solid-State Sensors and Actuators, Chicago, Jun. 16-19, 1997, Transducers 97, pp. 121-124.

(Continued)

*Primary Examiner*—Michael Nghiem

(57) ABSTRACT

Fluid monitoring methods, systems and apparatus are disclosed, including a portable subassembly that is in electrical communication with a sensor in contact with the fluid being monitred. Preferred embodiments for the sensor include one or more flexural resonator sensing elements. In preferred embodiments the sensor subassembly is ported to multiple fluidic systems to monitor the fluid properties in an effecient manner.

8 Claims, 23 Drawing Sheets

U.S. PATENT DOCUMENTS

| | | | |
|---|---|---|---|
| 6,082,181 | A | 7/2000 | Greenwood |
| 6,182,499 | B1 | 2/2001 | McFarland et al. |
| 6,223,589 | B1 | 5/2001 | Dickert et al. |
| 6,311,549 | B1 | 11/2001 | Thundat et al. |
| 6,336,353 | B2 | 1/2002 | Matsiev et al. |
| 6,393,895 | B1 | 5/2002 | Matsiev et al. |
| 6,401,519 | B1 | 6/2002 | McFarland et al. |
| 6,494,079 | B1 | 12/2002 | Matsiev et al. |
| 6,845,663 | B2 * | 1/2005 | Lopatin et al. ........... 73/290 V |
| 6,873,916 | B2 | 3/2005 | Kolosov |
| 2002/0178805 | A1 | 12/2002 | DiFoggio et al. |
| 2004/0107055 | A1 | 6/2004 | Kolosov et al. |
| 2005/0145019 | A1 * | 7/2005 | Matsiev et al. ............ 73/53.01 |

FOREIGN PATENT DOCUMENTS

| | | |
|---|---|---|
| EP | 0 282 251 | 9/1988 |
| EP | 0 943 091 | 5/2003 |
| WO | WO99/18431 | 4/1999 |
| WO | WO 01/67068 | 9/2001 |
| WO | WO 02/077613 | 10/2002 |
| WO | WO 02/099414 | 12/2002 |

OTHER PUBLICATIONS

Grate, Jay W., "Smart Sensor System for Trace Organophosphorus and Organosulfur Vapor Detection Employing a Temperature-Controlled Array of Surface Acoustic Wave Sensors, Automated Sample Preconcentration, and Patter", Anal. Chem., vol. 65, 1993, pp. 1868-1881.

Greenwood, M.S., "On-line Sensor for Density and Viscosity Measurements of a Liquid or Slurry for Process Control in the Flood Industry", 1999 AiChE Annual Meeting.

Hammond et al., An Acoustic Automotive Engine Oil Quality Sensor; 1997 IEEE International Frequency Control Symposium, pp. 72-80.

Martin, Bret A., "Viscosity and Density Sensing with Ultrasonic Plate Waves", Sensors and Actuators, vol. A21-A23, 1990, pp. 704-708.

Matsiev, Leonid, "Application of Flexural Mechanical Resonators to Simultaneous Measurements of a Liquid Density and Viscosity", IEEE Ultrasonics Symposium Proceedings, 1999, pp. 457-460.

Trolier, Susan, "Preparation of Chemically Etched Piezoelectric Resonators for Density Meters and Viscometers", Mat. Res. Bull., vol. 22, 1987, pp. 1267-1274.

U.S. Appl. No. 60/456,767 entitled "Mechanical Resonator" filed Mar. 21, 2003; Padowitz et al. (19 pages).

U.S. Appl. No. 60/456,767 entitled "Resonator Sensor Assembly" filed Mar. 21, 2003; Kolosov et al. (22 pages).

U.S. Appl. No. 10/394,543 entitled "Application Specific Integrated Circuitry for Controlling Analysis for a Fluid" filed Mar. 21, 2003; Kolosov et al. (57 pages).

U.S. Appl. No. 10/452,264 entitled "Machine Fluid Sensor and Method" filed Jun. 2, 2003; Matsiev et al. (32 pages).

U.S. Appl. No. 60/505,943 entitled "Environmental Control System Fluid Sensing System and Method" filed Sep. 25, 2003; Matsiev et al. (46 pages).

PCT Application Ser. No. PCT/US03/32983 entitled "Environmental Control System Fluid Sensing System and Method" filed Oct. 17, 2003; Matsiev et al. (53 pages).

U.S. Appl. No. 10/804,446 entitled "Mechanical Resonator" filed Mar. 19, 2004; Kolosov et al. (20 pages).

PCT Application Ser. No. PCT/US04/008555 entitled "Application Specific Integrated Circuitry for Controlling Analysis for a Fluid" filed Mar. 19, 2004; Kolosov et al. (66 pages).

U.S. Appl. No. 10/804,379 entitled "Resonator Sensor Assembly" filed Mar. 19, 2004; Kolosov et al. (23 pages).

PCT Application Ser. No. PCT/US04/008552 entitled "Resonator Sensor Assembly" filed Mar. 19, 2004; Kolosov et al. (24 pages).

* cited by examiner

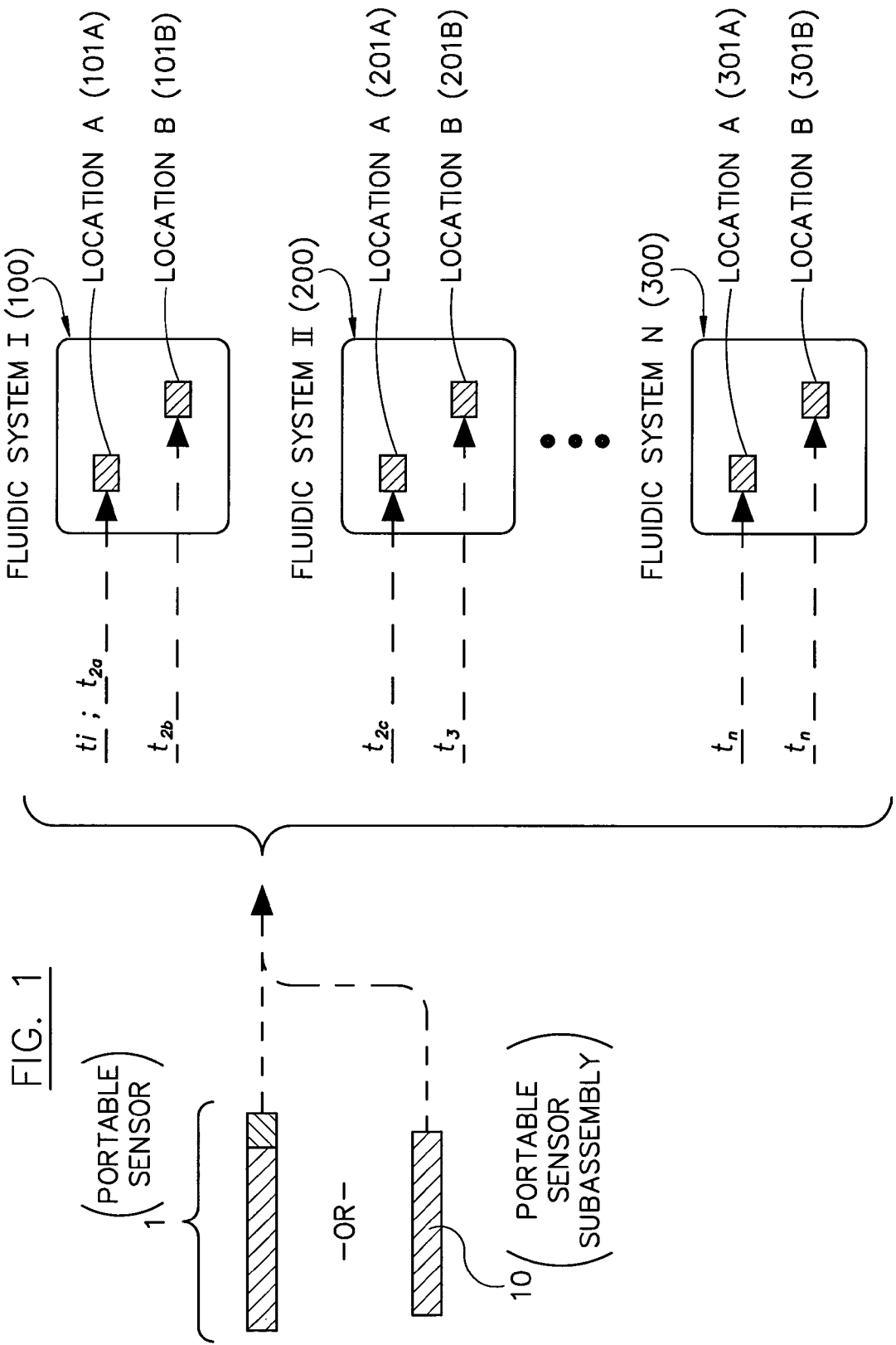

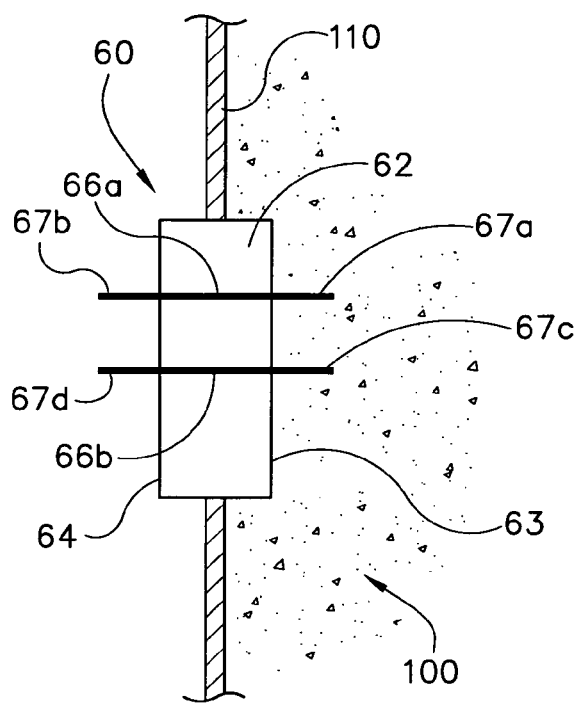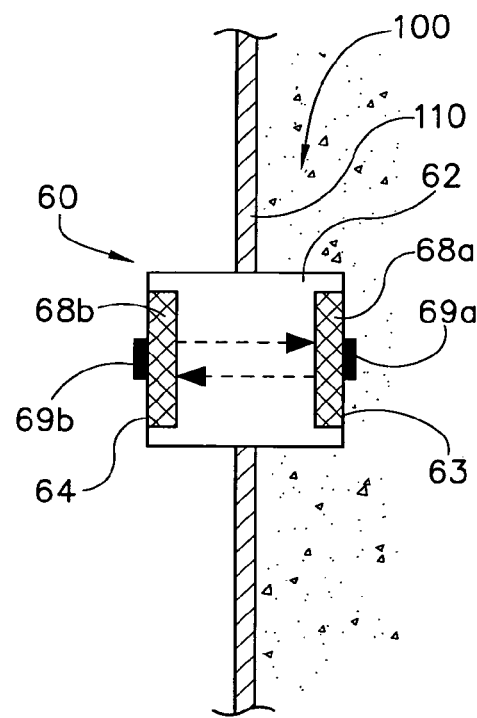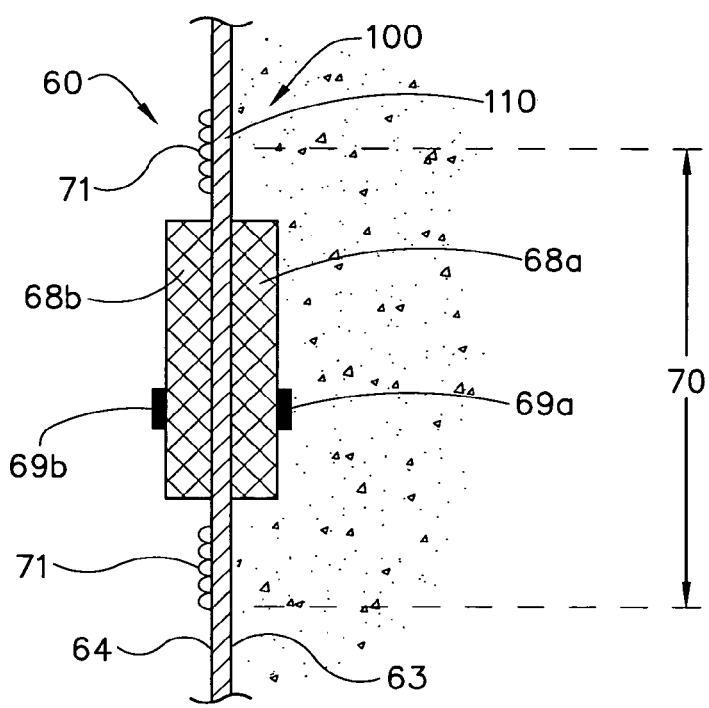

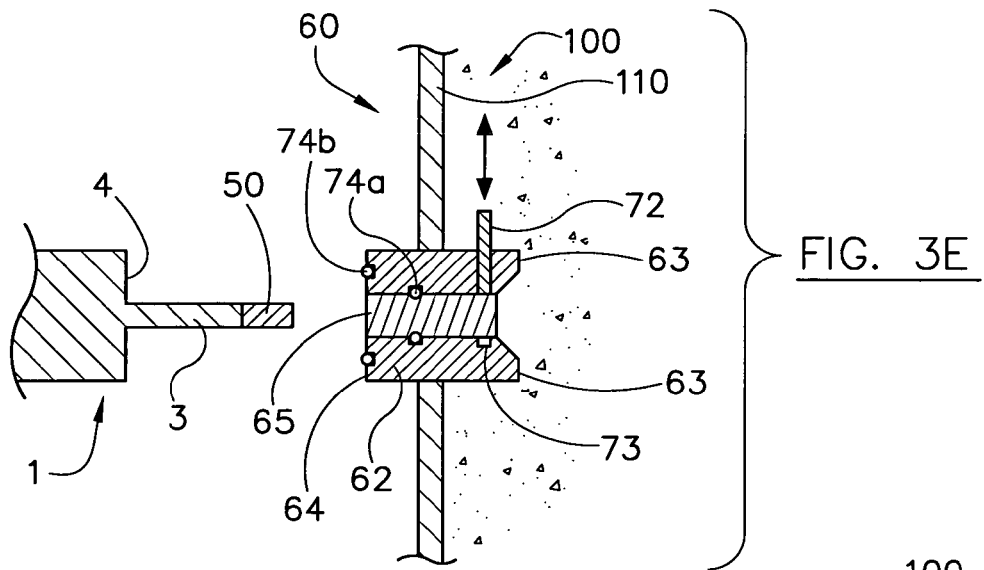
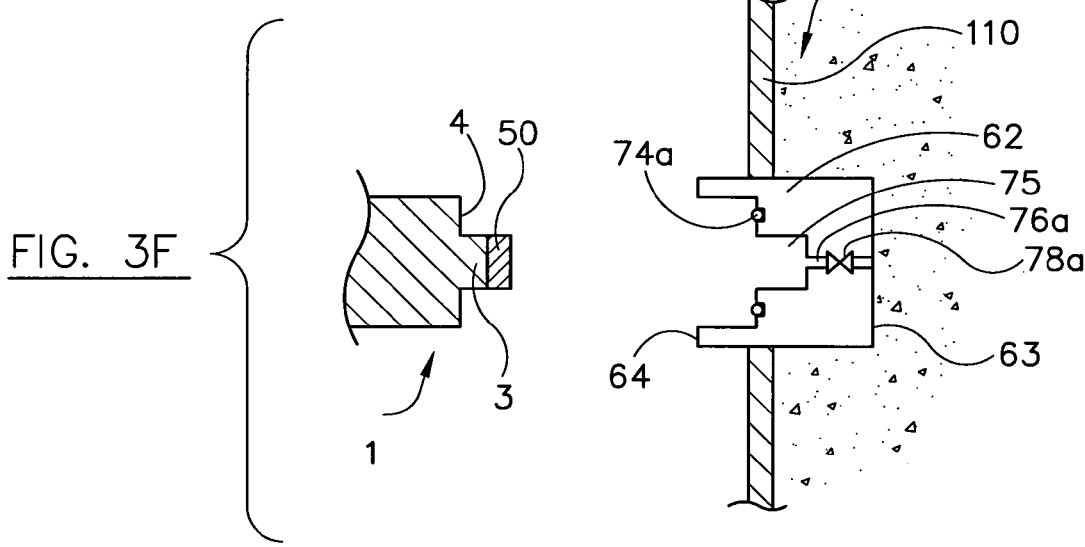
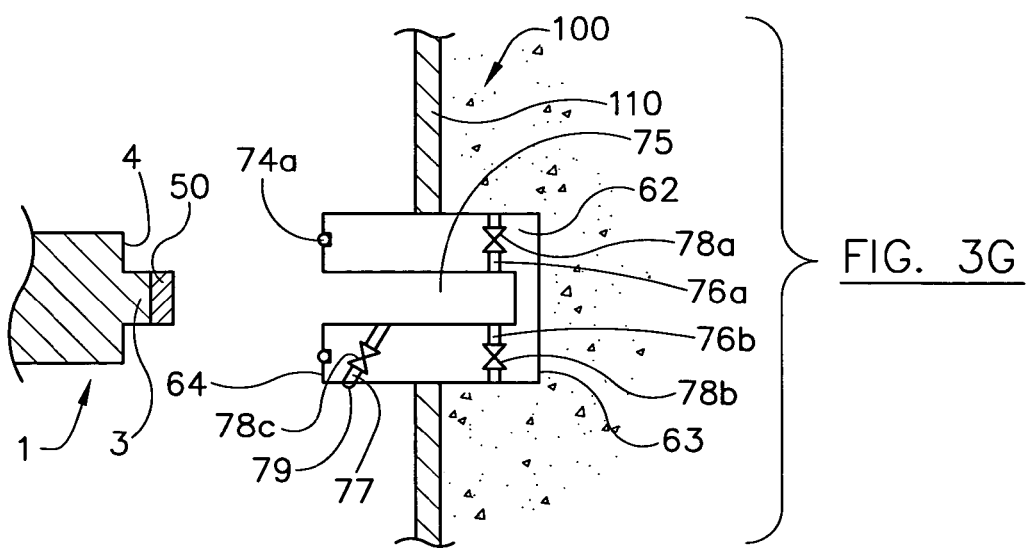

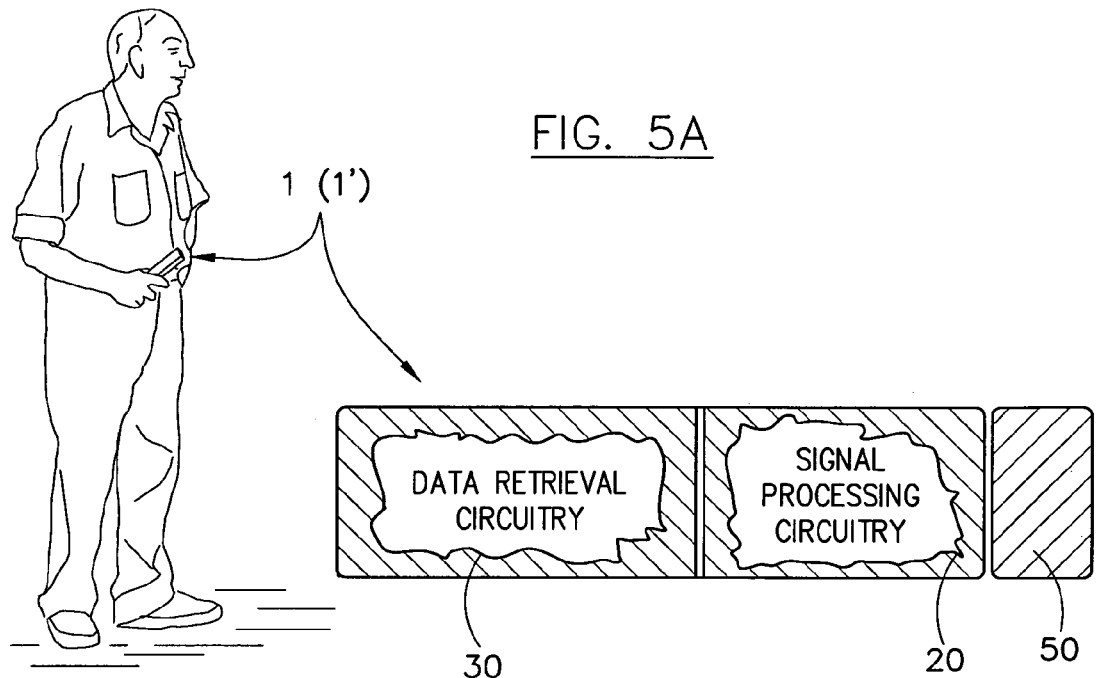
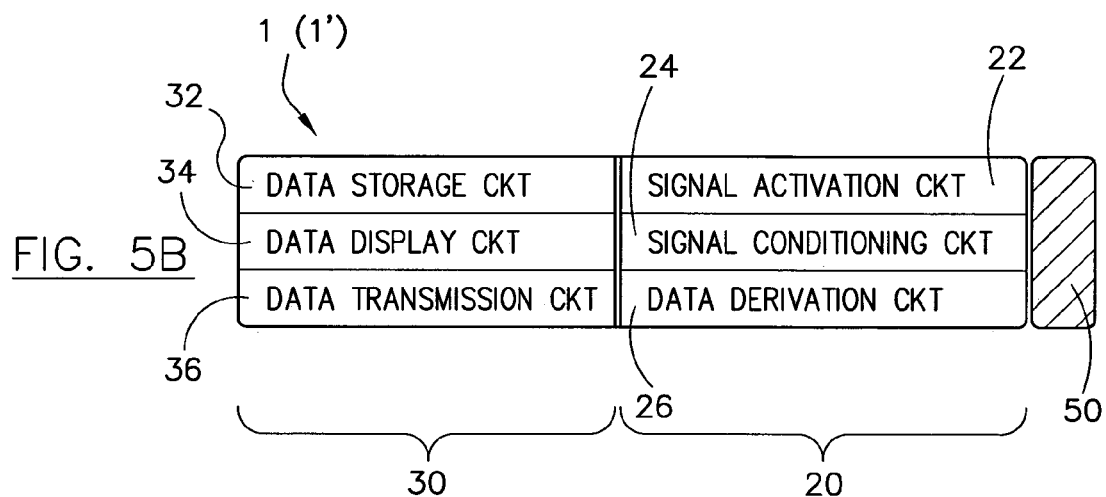
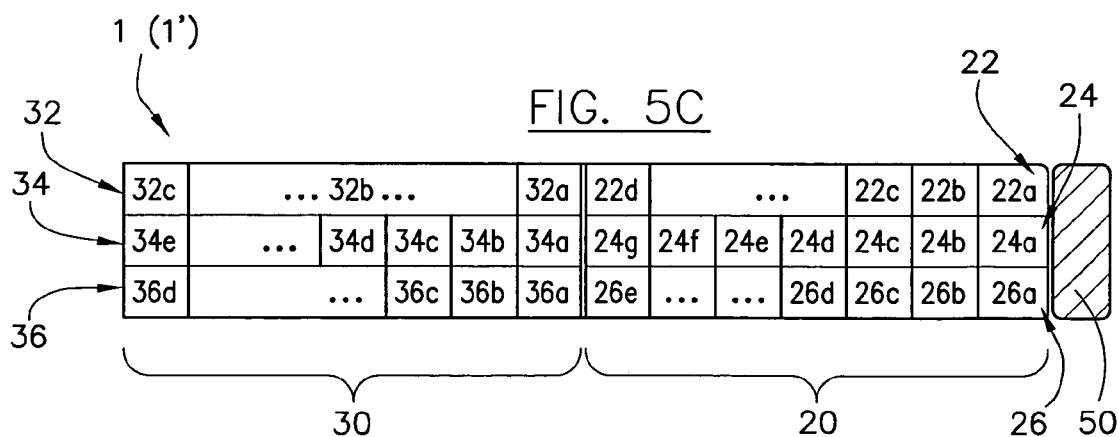

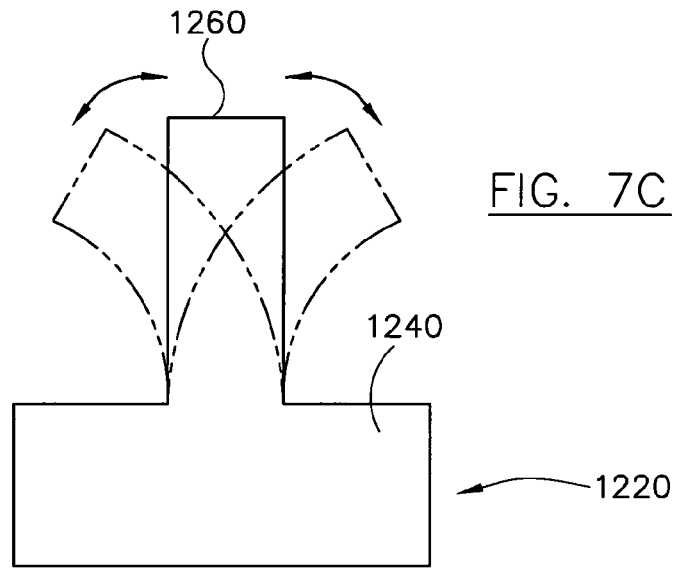
FIG. 7C
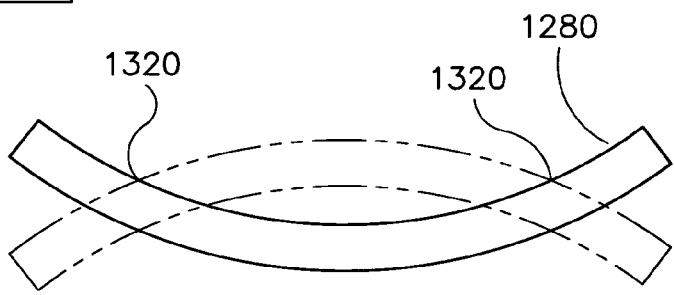
FIG. 7D
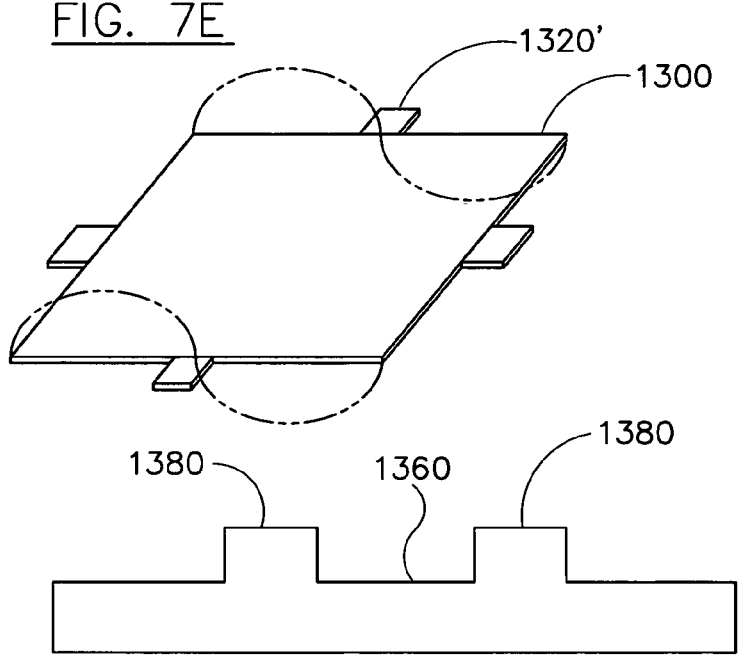
FIG. 7E
FIG. 7F

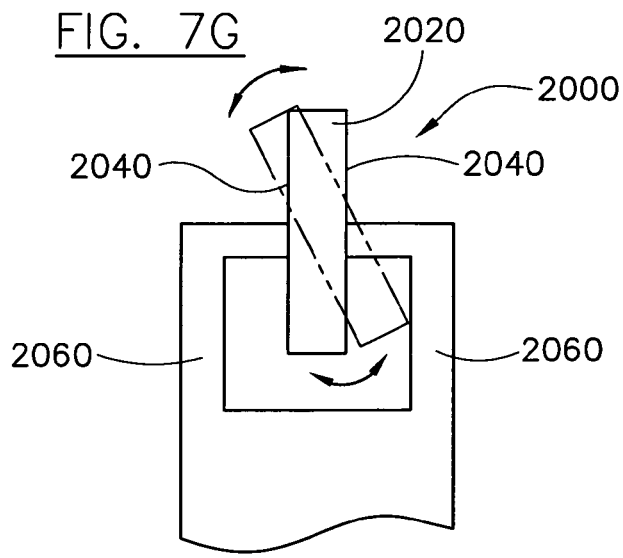
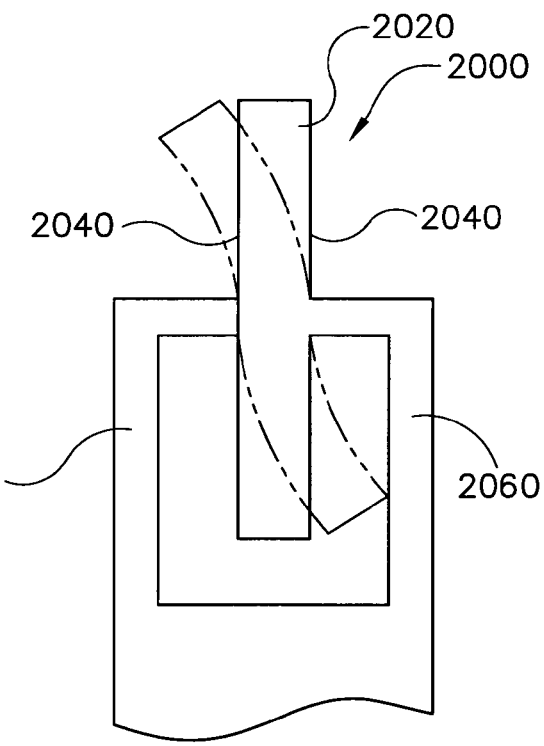
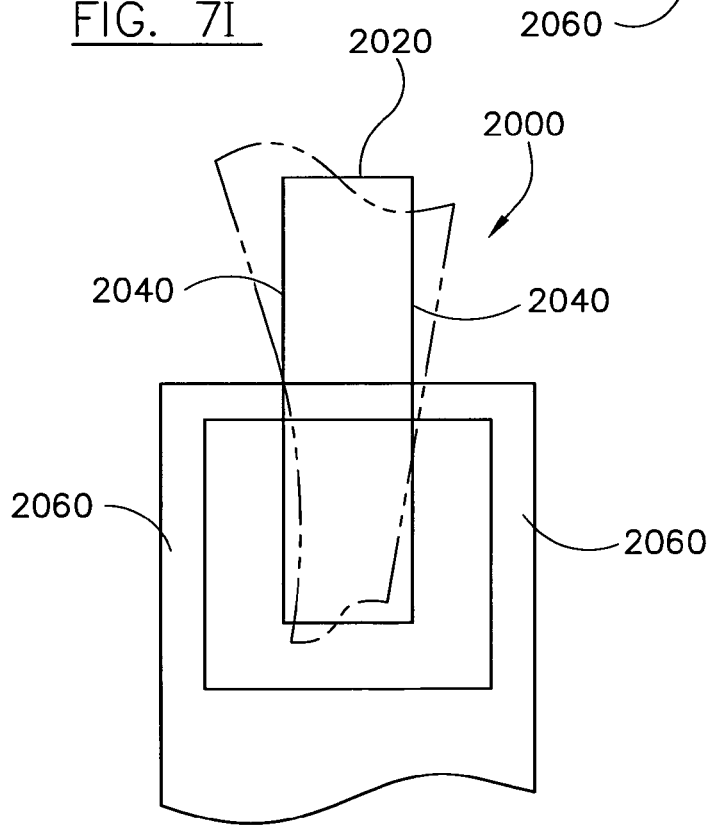

FIG. 8B $$V_{out}(C_o, C_p, L_o, C_s, R_o, Z(\omega), A, B, \rho, \eta, \omega, \varepsilon) \quad (1)$$

$$V_{out}(\omega) = \frac{V_o(Z_{in}(\omega))}{(Z_{in}(\omega))+(Z_{tf}(\omega))} \quad (2)$$

$$Z_{in} = R_{in}*(1/i\omega C_{in})(R_{in}+1/i\omega C_{in})^{-1} \quad (3)$$

$$Z_{tf} = (1/i\omega C_p)(R_o+1/i\omega C_s+i\omega L_o) \\ (1/i\omega C_p+R_o+1/i\omega C_s+i\omega L_o)^{-1} \quad (4)$$

$$Z(\omega) = Ai\omega p + B*(\omega\rho\eta)^{1/2}(1+i) \quad (5)$$

$$\varepsilon_{measured} = a + k*C_{p(measured)} \quad (6)$$

$$\varepsilon_{measured} = [\varepsilon_{cal} - (\varepsilon_{cal} - 1) * [C_{p_{cal}}/(C_{p_{cal}} - C_{p_o})]] + \\ [C_{p(measured)} * [(\varepsilon_{cal} - 1)/(C_{p_{cal}} - C_{p_{o(vacuum)}})]] \quad (7)$$

$$a = [\varepsilon_{cal} - (\varepsilon_{cal} - 1) * [C_{p_{cal}}/(C_{p_{cal}} - C_{p_o})]] \quad (8)$$

$$k = [(\varepsilon_{cal} - 1)/(C_{p_{cal}} - C_{p_{o(vacuum)}})] \quad (9)$$

$$C_{p(measured)} \text{ IS A FUNCTION OF "k"} \quad (10)$$

FIG. 8C $$Z(\omega) = Ai\omega\rho + B\sqrt{\omega\rho\eta}\,(1+i)$$

$$Z(\omega) = i\omega\Delta L + \Delta Z\sqrt{\omega}\,(1+i)$$

$$\Delta L = A\rho, \quad \Delta Z = B\sqrt{\rho\eta}$$

FIG. 9D

APPROXIMATED FLUID CHARACTERISTICS

| | | DENSITY | VISCOSITY | DIELECTRIC CONSTANT |
|---|---|---|---|---|
| TUNING FORK 1.1 TEMP. 25° C | OIL TYPE 1 | $\rho$ | $\eta$ | $\varepsilon$ |
| | OIL TYPE 2 | $\rho$ | $\eta$ | $\varepsilon$ |
| | OIL TYPE 3 | $\rho$ | $\eta$ | $\varepsilon$ |
| CALIBRATION VARIABLES $V_1$ $V_2$ $V_3$ $V_4$ $V_5$ $V_6$ $V_7$ | OIL TYPE 4 | $\rho$ | $\eta$ | $\varepsilon$ |
| | OIL TYPE 5 | $\rho$ | $\eta$ | $\varepsilon$ |
| | OIL TYPE 6 | $\rho$ | $\eta$ | $\varepsilon$ |
| | ⋮ | ⋮ | ⋮ | ⋮ |
| | OIL TYPE N | $\rho$ | $\eta$ | $\varepsilon$ |

FIG. 9E

APPROXIMATED FLUID CHARACTERISTICS

| | | DENSITY | VISCOSITY | DIELECTRIC CONSTANT |
|---|---|---|---|---|
| TUNING FORK 1.1 TEMP. 40° C | OIL TYPE 1 | $\rho'$ | $\eta'$ | $\varepsilon'$ |
| | OIL TYPE 2 | $\rho'$ | $\eta'$ | $\varepsilon'$ |
| | OIL TYPE 3 | $\rho'$ | $\eta'$ | $\varepsilon'$ |
| CALIBRATION VARIABLES $V_1'$ $V_2'$ $V_3'$ $V_4'$ $V_5'$ $V_6'$ $V_7'$ | OIL TYPE 4 | $\rho'$ | $\eta'$ | $\varepsilon'$ |
| | OIL TYPE 5 | $\rho'$ | $\eta'$ | $\varepsilon'$ |
| | OIL TYPE 6 | $\rho'$ | $\eta'$ | $\varepsilon'$ |
| | ⋮ | ⋮ | ⋮ | ⋮ |
| | OIL TYPE N | $\rho'$ | $\eta'$ | $\varepsilon'$ |

APPLICATIONS  FIG. 12A
- TRANSPORTATION (AIR, SEA, LAND, SPACE)
- WORKING VEHICLES (CONSTRUCTION, AGRICULTURE, MINING, SUB-SEA ROV, TRUCKING)
- MILITARY VEHICLES (HMVVE, TANKS, TRUCKS, ect)
- HEAVY MACHINERY (INDUSTRIAL, MANUFACTURING)
- INDUSTRIAL WASTEWATER
- DRINKING WATER
- OIL AND GAS EXPLORATION AND PRODUCTION
  (DRILLING, WELLBORE AND PRODUCTION LOGGING, LABORATORY OIL ANALYSIS, SEPARATION)
- FUEL AND HYDROCARBON TRANSPORTATION
- REFINING (REACTORS, CONDUITS, CONDENSERS)
- PETRO CHEMICAL (REACTORS, CONDUITS, CONDENSERS)
- CHEMICAL (REACTORS, CONDUITS, CONDENSERS)
- FOOD STORAGE AND PROCESSING
- HEAT EXCHANGERS
- CRYOGENIC SYSTEMS
- BIOSENSORS
- CHEMICAL SENSORS
- POWER GENERATION (RECIPROCAL, TURBINE, HYDRO, FUEL CELLS)
- VAPOR DETECTION (HUMIDITY, FUMES)
- MEDICAL (DEVICE AND PHARMA)
- LABORATORY (AUTOMATED, HAND-HELD)
- PRINTING (INDUSTRIAL PRINTERS, DESKJET)
- MANUFACTURING (PAINTS, INKS)
- MANUFACTURING EQUIPMENT MONITORING
  (CNC EQUIPMENT LUBRICANT, EXTRUSION POLYMER MONITORING)
- ENVIRONMENTAL HAZARD SAMPLING AND MONITORING
- HOMELAND SECURITY
- PETROCHEMICAL TRANSPORTATION FLUIDIC SYSTEMS  FIG. 12B
- ENGINES (RECIPROCAL, TURBINE, ELECTRIC)
- BRAKES (AUTOMOTIVE, INDUSTRIAL)
- TRANSMISSIONS (HYDRAULIC, GEAR)
- HEAT EXCHANGERS (RADIATORS, HVAC&R, COOLERS, CHILLERS)
- FUEL STORAGE AND TRANSMISSION
- PIPELINES
- STORAGE TANKS
- HVAC&R SYSTEMS
- COMPRESSORS (AIR, GAS)
- VACUUM PUMPS
- GEAR BOXES
- DEWARS
- BUILDINGS (ATMOSHERICS IN BUILDINGS AND HOUSES ..aka. HUMIDITY SENSOR)
- MAMMALIAN BODY (VEINS, LUNGS, GUT)
- WELLS (OIL, GAS, WATER)
- PRINTING PRESS
- TURBINES
- LUBRICATION SYSTEMS

FIG. 12C

FLUIDS
- OILS, GREASES, HYDRAULICS (SYNTHETICS AND HC)
- GASES (REACTOR FEEDS, HC'S, INORGANICS INCLUDING CRYO'S)
- HEAT EXCHANGER FLUID (WATER, GLYCOL, "DOWTHERMS", REFRIGERANTS)
- CRUDE OIL
- FUEL (GASOLINE, DEISEL, BIODEISEL, ETHANOL, METHANOL, HYDROGEN)
- MAMMALIAN (BLOOD, URINE, VAGINAL)
- FOOD (BATTER, OILS, GREASES, GELS, PASTES, ALCOHOLS)
- SOLVENTS (LABORATORY, INDUSTRIAL, HOME)
- CLEANERS (WINDSHEILD WASHER FLUUID, ETC.)
- INK
- FLUIDIZED BEDS
- AMBIENT AIR
- EXHAUST GASES
- HYDROGEN
- INERT GASES

PORTABLE FLUID SENSING DEVICE AND METHOD

BACKGROUND OF INVENTION

The present invention generally relates to the field of fluid sensors and more particularly to the field of portable fluid sensor devices and methods useful in field operations, including field operations involving process monitoring, process control and/or process or system servicing. The present invention relates, in preferred embodiments, to portable fluid sensor devices and methods adapted for use in closed fluid systems such as recirculating fluid systems (e.g., environmental control systems, engine systems, transportation vehicle systems, etc.). The present invention relates, in particularly preferred embodiments, to the field of fluid sensor devices and methods involving a mechanical resonator sensor such as a flexural resonator sensor.

Effective approaches for measuring characteristics of fluids using mechanical resonators are disclosed in commonly-owned U.S. Pat. Nos. 6,401,519; 6,393,895; 6,336,353; 6,182,499; 6,494,079 and EP 0943091 B1, each of which are incorporated by reference herein for all purposes. See also, Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is also incorporated by reference herein for all purposes. The use of a quartz oscillator in a sensor has been described as well in U.S. Pat. Nos. 6,223,589 and 5,741,961, and in Hammond, et al., "*An Acoustic Automotive Engine Oil Quality Sensor*", Proceedings of the 1997 IEEE International Frequency Control Symposium, IEEE Catalog No. 97CH36016, pp. 72-80, May 28-30, 1997.

The use of other types of sensors is also known in the art. For example, the use of acoustic sensors has been addressed in applications such as viscosity measurement in J. W. Grate, et al, Anal. Chem. 65, 940A-948A (1993)); "*Viscosity and Density Sensing with Ultrasonic Plate Waves*", B. A. Martin, S. W. Wenzel, and R. M. White, Sensors and Actuators, A21-A23 (1990), 704-708; "*Preparation of chemically etched piezoelectric resonators for density meters and viscometers*", S. Trolier, Q. C. Xu, R. E. Newnham, Mat. Res. Bull. 22, 1267-74 (1987); "*On-line Sensor for Density and Viscosity Measurement of a Liquid or Slurry for Process Control in the Food Industry*", Margaret S. Greenwood, Ph.D. James R. Skorpik, Judith Ann Bamberger, P. E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and "*Micromachined viscosity sensor for real-time polymerization monitoring*", O. Brand, J. M. English, S. A. Bidstrup, M. G. Allen, Transducers '97, 121-124 (1997). See also, U.S. Pat. No. 5,586,445 ("*Low Refrigerant Charge Detection Using a Combined Pressure/Temperature Sensor*").

Notwithstanding the above, there remains a need in the art for alternative or improved sensor devices and methods for efficiently evaluating fluids used in fluidic systems, including for example in residential, commercial and industrial process streams and/or in machines used in such process streams and/or in stand-alone machines. Examples in which such a need exists include those fluidic systems used in connection with the petroleum, chemical, pharmaceutical, healthcare, environmental, military, aerospace, construction, heating, ventilating, air-conditioning, refrigeration, food, and transportation industries. In particular, there remains a need in the art for a cost-effective approach for servicing fluidic systems where such fluidic systems are of a common type but are very numerous (e.g., residential air-conditioning fluidic systems) and/or are found within a common service sector but have temporally and/or spatially diverse fluid characteristics (e.g., transportation vehicle fluidic systems).

SUMMARY OF INVENTION

It is therefore an object of the present invention to provide improved sensor devices and methods for efficiently monitoring fluids used in fluidic systems. In particular, it is an object of the invention to a cost-effective approach for monitoring multiple, numerous and/or diverse fluidic systems. In preferred embodiments, it is an object of the invention to provide devices and methods for efficiently and effectively monitoring multiple properties of a fluid in such fluidic systems.

Briefly, therefore, the present invention is broadly directed to various methods for monitoring a property of a fluid in a fluidic system using a sensor, such as a mechanical resonator sensor. In preferred embodiments, the sensor is a flexural resonator sensor.

The invention is also broadly directed to various systems for monitoring a property of one or more fluids in one or more fluidic systems, and in preferred embodiments, in multiple fluidic systems. The system generally comprises a sensor interfaced with a fluidic system, such as a mechanical resonator sensor. In preferred embodiments, the sensor is a flexural resonator sensor. The system also comprises one or more circuits, such as signal processing circuits and/or data retrieval circuits.

The invention is further broadly directed to various apparatus for use in monitoring a property of one or more fluids in one or more fluidic systems. Such apparatus generally comprise a personally portable or hand-held unit—sensor or sensor subassembly. In preferred embodiments, the unit includes a flexural resonator sensor or flexural resonator sensor subassembly.

In the methods, systems and apparatus of the present invention, a property of a fluid in a fluidic system is monitored using a sensor interfaced with the fluidic system. In some embodiments, the interfaced sensor is formed from and includes at least one sensor subassembly interfaced with an installed unit that is either a sensor or another sensor subassembly. Likewise, the systems and apparatus of the present invention comprise a sensor or a sensor subassembly. In each case, the sensor is preferably a mechanical resonator sensor, and is most preferably a flexural resonator sensor. In preferred embodiments, a flexural resonator sensor comprises a flexural resonator sensing element having a sensing surface for contacting the fluid being sensed. In operation during a sensing period, the sensing surface of a flexural resonator displaces or is displaced by at least a portion of the fluid being sensed. The flexural resonator sensor can be operated passively or actively, and if actively operated, is preferably excited using a stimulus signal. The particular nature of the stimulus signal is not critical, but in some embodiments, the stimulus signal can be a waveform having a frequency (e.g., a predetermined frequency) or having a range of frequencies (e.g., being swept over a determined or predetermined range of frequencies), and in each such case, having a frequency or a range of frequencies of less than about 1 MHz. In some embodiments, additional sensors (e.g., such as temperature and/or pressure sensors) can be employed in combination with a mechanical resonator sensor such as a flexural resonator sensor. In some embodiments, alternative sensors can be employed in place of a mechanical resonator sensor such as a flexural resonator sensor. Further discussion of preferred sensors and sensor subassemblies (comprising or more components of a sensor), as well as the preferred use thereof, are described hereinafter.

General Overview—Methods

Generally, the method comprises porting a sensor or a sensor subassembly to a (first) fluidic system. The ported sensor or ported sensor subassembly is interfaced with the (first) fluidic system at a (first) location. The interfaced sensor is operationally configured for generating or retrieving data (directly or upon activation in an active sensing step) that can be associated with one or more properties of the fluid. Hence, the interfaced sensor generally comprises a sensing element (e.g., a flexural resonator) having a sensing surface for contacting the fluid, and a data retrieval circuit in electrical communication with the sensing element. The data retrieval circuit can be in electrical communication with the sensing element directly, or alternatively, via a signal processing circuit that processes (e.g., via signal conditioning circuitry that amplifies, biases, converts, etc. or otherwise conditions, and/or via data derivation circuitry that detects a signal of or that determines a parameter based on) raw data coming from the sensing element or from a storage media storing such raw data. In preferred embodiments, the interfaced sensor comprises a sensing element (e.g., a flexural resonator) having a sensing surface for contacting the fluid, a signal processing circuit (e.g., an amplifying circuit) in electrical communication with the flexural resonator, and a data retrieval circuit in electrical communication with the signal processing circuit. Regardless of the particular configuration for the interfaced sensor, the fluid is sensed, actively or passively, using the interfaced sensor during a first sensing period to generate data associated with one or more properties of the fluid. The generated data is then stored (e.g., in memory within a data storage media), displayed (e.g., in a graphical user interface or other display device) or (meaning additionally or alternatively) transmitted, for example between one or more of: an installed related components of the fluidic system; the interfaced sensor; the ported sensor subassembly; or a remote data repository, and in any case, using for example, hard-wired or wireless communications protocols.

Typically, at some time after the first sensing period (regardless of whether there are additional intermittent sensing periods), the general method can further generally comprise disinterfacing (e.g., disengaging) the sensor or sensor subassembly from the (first) location of the (first) fluidic system. The disinterfaced sensor or disinterfaced sensor subassembly can be ported away from the (first) location of the (first) fluidic system, and thereafter, the sensor or sensor subassembly can be (re)ported to one or more of (i) another (second) fluidic system, (ii) another (second) location of the (first) fluidic system, or (iii) the same (first) location of the (first) fluidic system—in each case for interfacing therewith to monitor a property of a fluid during a separate discrete (second) sensing period. Optionally, the sensing element surface exposed to the fluid under test can be washed (e.g., using rinse water or other appropriate solvent) or alternatively, disposed and replaced, between sensing periods.

In particular for example, after first sensing period, the general method can further generally comprise porting the disinterfaced sensor or the subassembly thereof to a second fluidic system and interfacing the disinterfaced ported sensor or ported sensor subassembly with the second fluidic system to form a (second) interfaced sensor. The fluid in the second fluidic system is sensed during a second sensing period using the (second) interfaced sensor to generate data associated with one or more properties of the fluid in the second fluidic system. The generated data is stored, displayed or transmitted using the data retrieval circuit of the (second) interfaced sensor.

As an alternative (or additional) example, after the first sensing period, the method can further generally comprise porting the disinterfaced sensor or the subassembly thereof to a second location of the first fluidic system, and interfacing the disinterfaced ported sensor or ported sensor subassembly with the first fluidic system at the second location thereof to form a (second) interfaced sensor. The fluid in the fluidic system is sensed during a second sensing period at the second location using the interfaced sensor to generate data associated with one or more properties of the fluid at the second location in the fluidic system. The generated data is stored, displayed or transmitted using the data retrieval circuit.

As another alternative (or additional) example, after the first sensing period, the method can further generally comprise porting the disinterfaced ported sensor or the ported sensor subassembly thereof to the first fluidic system at a later second time, and interfacing the disinterfaced ported sensor or ported sensor subassembly with the first location of the first fluidic system at the second time to form an interfaced sensor. The fluid in the fluidic system is sensed at the same first location during the second sensing period using the interfaced sensor to generate data associated with one or more properties of the fluid at the second time in the fluidic system. The generated data is stored, displayed or transmitted at the second time in the fluidic system using the data retrieval circuit.

Generally, in any of the embodiments discussed herein, fluid properties of a fluidic system can be monitored either locally (at the fluidic system) or remotely (at a location removed from the fluidic system)—or both locally and remotely, including for example with different degrees of information available locally and remotely. Local monitoring can include one or more display devices, including for example a user interface allowing user input/output with the interfaced sensor and/or with the ported sensor or ported sensor subassembly. Remote monitoring can include a remote data repository (e.g., remote, centrally-located server comprising a database), and can additionally or alternatively also include a user interface. Hard-wired and/or wireless communications can facilitate remote monitoring of fluid properties in the fluidic system, including data transfer between any of one or more of: (i) the interfaced sensor, (ii) the ported sensor or ported sensor subassembly and/or (iii) one or more remote data reception units (e.g., remote monitoring station). Additionally, at least a portion of such communications can be effected over known and developing communication infrastructures using known and developing protocols, such as internet infrastructures and protocols (both hard-wired and wireless infrastructure and protocols). Such remote monitoring can be supplemented by local monitoring.

General Overview—Systems and Apparatus

In the systems or apparatus of the invention, the ported sensor, the ported sensor subassembly and/or the interfaced sensor comprises a sensor, and preferably a mechanical resonator sensor such as a flexural resonator sensor. The sensor comprises a sensing surface for contacting a fluid. In preferred embodiments, a flexural resonator sensor (or subassembly thereof) comprises a flexural resonator sensing element having a sensing surface for contacting the fluid being sensed. The sensing surface of a flexural resonator is adapted for or configured for displacing (or being displaced by) at least a portion of the fluid being sensed, at least during sensing operations. Although much of the description is presented herein in the context of flexural resonator sensors, various aspects of the invention are not limited to such sensors. In addition, other sensors (or sensor subassemblies) can be used in combination with the mechanical resonator sensor or other types of sensors mentioned above. For example, temperature sensors and/or pressure sensors can be employed in combination with the mechanical resonators or other type of sensors.

A system of the invention can be effective for monitoring a property of a fluid in a fluidic system. Such a monitoring system generally comprises a sensor (e.g., a flexural resonator sensor) interfaced with a fluidic system. As interfaced, the interfaced sensor can comprise a sensing element (e.g., a flexural resonator) having a sensing surface adapted for or configured for contacting the fluid, and being responsive to changes in one or more properties of a fluid. The interfaced sensor further comprises a data retrieval circuit in electrical communication with the sensing element—directly, or via one or more intermediate circuits (e.g., a signal processing circuit)—the data retrieval circuit being effective for storing, displaying or transmitting data (in each case including raw or processed data. The interfaced sensor can, as an alternative to or in addition to the data retrieval circuit, further comprise one or more signal processing circuits (e.g., a signal conditioning circuit such as an amplifying circuit, etc., and/or a data derivation circuit such as a signal detection circuit or a microprocessor, etc.) for processing (raw or previously processed) data originating from the sensing element (e.g., flexural resonator). In general, the interfaced sensor can be a sensor formed by interfacing a sensor (in its entirety) with the fluidic system, or alternatively, the interfaced sensor can be a sensor formed by interfacing one or more portable sensor subassemblies with one or more previously installed sensors or previously installed sensor subassemblies.

An apparatus of the invention can be useful in connection with fluidic systems for monitoring a property of a fluid therein. Generally, the apparatus of the invention comprise a personally portable sensor such as a mechanical resonator sensor (e.g., flexural resonator sensor) or a personally portable subassembly thereof. In preferred embodiments, the sensor or sensor subassembly comprise one or more of the following, in any of the various permutations/combinations: a sensing element (e.g., flexural resonator sensing element) having a sensing surface for contacting a fluid; signal processing circuitry adapted for or configured for processing raw data or previously-processed data or retrieved data (e.g., previously stored or transmitted data); and/or data retrieval circuitry for retrieving data (e.g., data storage circuitry, data display circuitry and/or data transmittal circuitry). In preferred embodiments, the signal processing circuit is in or is adapted for or configured for receiving an signal (directly or indirectly) from a flexural resonator sensing element during a sensing period and processing that received signal. The processing of the received signal preferably effects a data output, for example, via the data retrieval circuitry, that can be useful for communicating a status or condition of the fluid to a person upon operation of the sensor in connection with the fluidic system.

The present invention offers significant advantages over previously-known approaches for monitoring a fluid in a fluidic system. In particular, the invention offers substantial flexibility to configure devices and methods that are efficient, effective and affordable for generating data associated with one or more properties of a fluid, and thereby providing a more comprehensive dataset from which process control and/or servicing decisions can be made. This flexibility allows for applications of the devices and methods of the invention across diverse industries, including for example, across industries such as the petroleum, chemical, pharmaceutical, healthcare, environmental, military, aerospace, construction, heating, ventilating, air-conditioning, refrigeration, food, and transportation industries. Significantly, the present invention also offers the advantage of for servicing fluidic systems where such fluidic systems are of a common type but are very numerous (e.g., air-conditioning fluidic systems, healthcare systems) and/or are found within a common service sector but have temporally and/or spatially diverse fluid characteristics (e.g., transportation vehicle fluidic systems, military platform fluidic systems, etc.).

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 1 is a schematic representation of the general methods, systems and/or apparatus of the invention.

FIGS. 3A through 3G are schematic representations of the general methods, systems and/or apparatus of the invention illustrating interfacing across a barrier defining a portion of the fluidic system.

FIG. 5A through 5C are schematic representations of a ported sensor comprising signal processing circuitry and/or data retrieval circuitry.

FIGS. 7A through 7I are schematic representations of a fluidic system (FIG. 7A) and of several configurations for flexural resonator sensing elements (FIG. 7B through 7I).

FIGS. 8A through 8C are a schematic representation of an equivalent circuit for a sensor comprising a flexural resonator sensing element (FIG. 8A) and of equations relating thereto (FIG. 8B and FIG. 8C).

FIGS. 9A through 9E are schematic representations of one preferred approach for circuitry that can be used in connection with embodiments of the invention, at least a portion of the circuitry being realized in an application specific integrated circuit (ASIC).

FIGS. 12 A through 12C are tables listing preferred application areas (fields of use), fluidic systems and fluids for which the methods, systems and apparatus of the inventions can be employed.

Figure 2A:
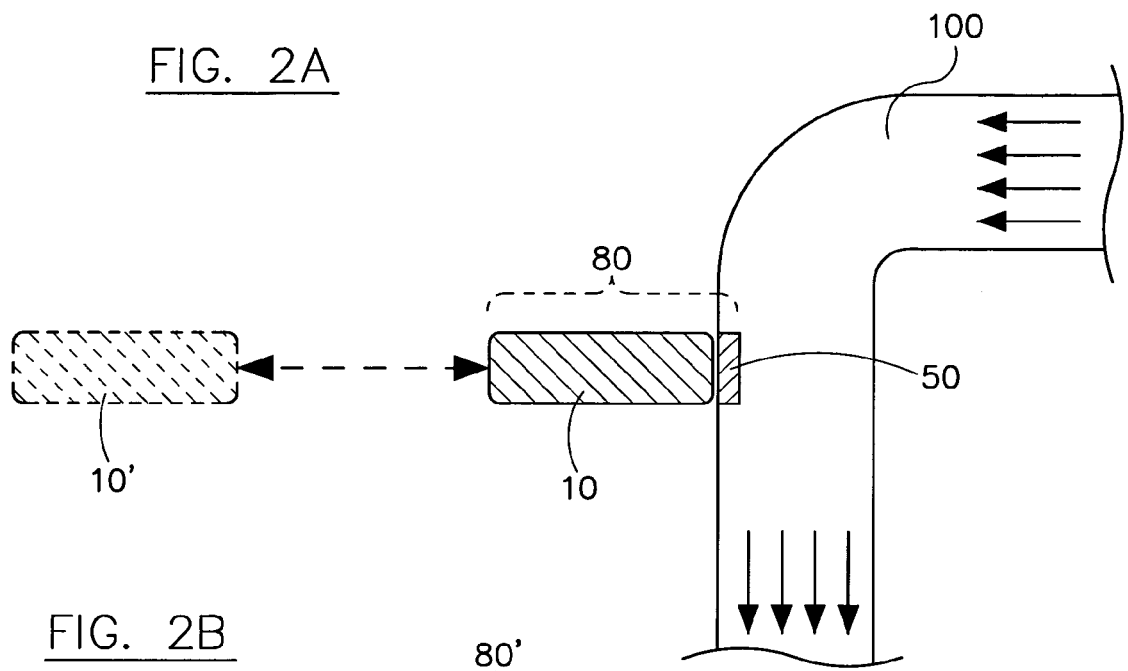
FIGS. 2A through 2C are schematic representations of the general methods, systems and/or apparatus of the invention illustrating sensor segmentation, in particular forming an interfaced sensor from a ported sensor subassembly and an installed sensor/sensor subassembly.

The invention is described in further detail below with reference to the figures, in which like items are numbered the same in the several figures.

DETAILED DESCRIPTION OF THE INVENTION

The following paragraphs describe certain features and combinations of features that can be used in connection with each of the methods, systems and apparatus of the invention, as generally described above. Also, particular features described hereinafter can be used in combination with other described features in each of the various possible combinations and permutations. As such, the invention is not limited to the specifically described embodiments.

Preferred General Methods

A preferred general method of the invention can be described, for example, with reference to FIG. 1, in which a ported sensor 1 or ported sensor subassembly 10 is interfaced with the (first) fluidic system 100 (indicated as "Fluidic System I") at a (first) location 101A (indicated as "Location A"). Using the interfaced sensor, the fluid is sensed during a first sensing period (indicated as "$t_1$") to generate data, which is then stored, displayed or transmitted using the data retrieval circuit of the interfaced sensor. After the first sensing period, the portable sensor 1 or sensor subassembly 10 is disinterfaced from the (first) location 101A of the (first) fluidic system 100, and ported away therefrom. Thereafter, the sensor 1 or sensor subassembly 10 can be (re)ported back to the same first fluidic system 100 at the same location 101A for sensing the fluid again during a later in time second sensing period (indicated as "$t_{2a}$"). Additionally or alternatively, thereafter the sensor 1 or sensor subassembly 10 can be (re)ported back to the same first fluidic system 100, but at a different (second) location 101B (indicated as "Location B") for sensing during a later in time second sensing period (indicated as "$t_{2b}$"). In addition or in the alternative to the aforementioned, thereafter the sensor 1 or sensor subassembly 10 can be ported to a second fluidic system 200 (indicated as "Fluidic System II") that is separate and discrete from the first fludic system 100, and having a first location 201A (indicated as "Location A") and optionally having a separate and distinct second location 201B (indicated as "Location B"). The sensing can be effected at the first location 201A of the second fluidic system 200 during a second sensing period (indicated as "$t_{2c}$"). Further sensing can thereafter be effected at other locations during other sensing periods. For example, thereafter, the sensing can be effected at the second location 201B of the second fluidic system 200 during a third sensing period (indicated as "$t_3$"). In like generalized manner, the sensing can thereafter be effected at one or more locations 301A, 301B of additional fluidic systems 300 (indicated as "Fluidic System N") during an $n^{th}$ sensing period (indicated as "$t_n$").

Figure 4A:
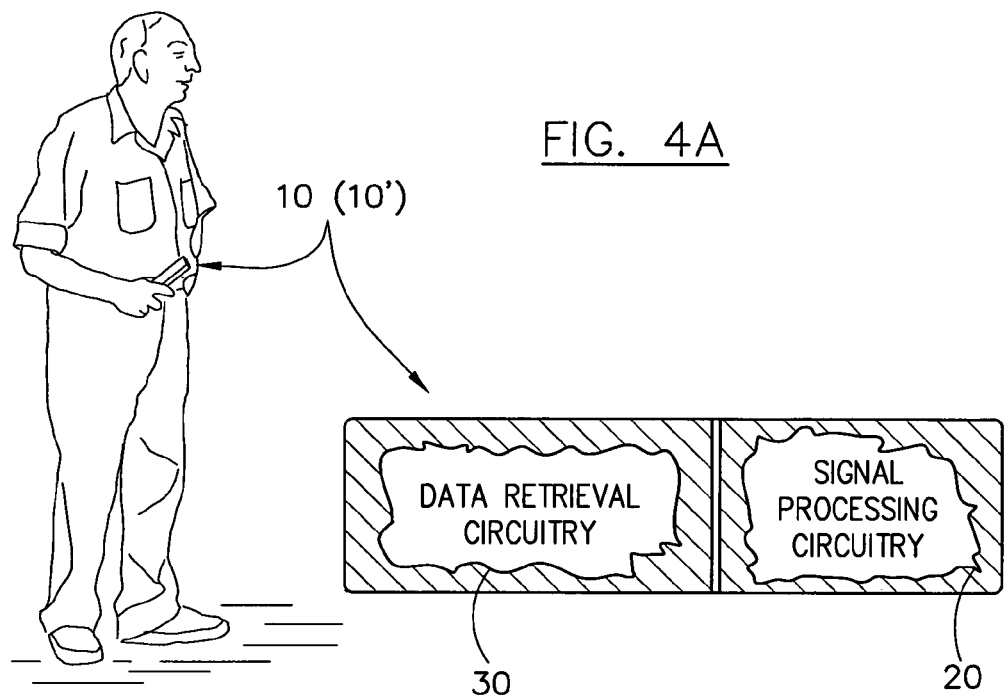
FIGS. 4A through 4C are schematic representations of a ported sensor subassembly comprising signal processing circuitry and/or data retrieval circuitry.

In a further generally preferred approach of the general method, with reference to FIGS. 2A and 4A, an interfaced sensor 80 is formed by interfacing at least one ported subassembly to form the interfaced sensor 80 in segmented form—specifically by interfacing a (first) portable and ported subassembly 10 (shown as 10' in its disinterfaced position) and a (second) installed sensor/sensor subassembly, typically comprising a sensing element 50. The second sensor/subassembly (e.g., comprising sensing element 50) can be preinstalled within the fluidic system 100, relative to the time at which the first subassembly 10 is ported to the fluidic system. Significantly, the segmentation of the interfaced sensor device 80 provides a technical basis which allows for efficient and economically attractive approach for monitoring fluids within a fluidic system 100 (e.g., for process control, quality control and/or servicing needs), because the first ported subassembly 10 (10') can be intermittently interfaced with installed sensors/sensor subassemblies at numerous locations on the same fluidic system or on numerous different fluidic systems and in either case, at numerous various times. Segmentation of the interfaced sensor 80 into an discretely packaged functional units, at least one of which is portable/ported, provides an economic and operational flexibility benefit over componently-fixed (e.g., "hard-wired/hard-plumbed") installed solutions for monitoring of numerous fluidic systems. In some cases, it provides a unique solution for fluidic systems that could not otherwise be multiplexed using componently-fixed (e.g., hard-wired) monitoring systems, including for example a fluidic system on a fleet of aircraft or a fleet of trucks or a fleet of cars). The particular segmentation approach is not narrowly critical to the invention. Generally, the installed sensor/sensor subassembly (typically already residing in physical local association with the fluidic system) comprises a sensing element 50 (e.g., mechanical resonator such as a flexural mechanical resonator) having a sensing surface positioned (meaning already positioned or adapted to be positionable) for contacting the fluid. The installed sensor/sensor subassembly may, optionally, also include one or more additional sensing elements (of the same type—e.g. an additional flexural resonator, or of a different type—e.g., a temperature sensing element or pressure sensing element) and/or one more signal processing circuits (e.g., a signal conditioning circuit such as an amplifier circuit, and/or e.g., a data derivation circuit such as a signal detection circuit) and/or one or more data retrieval circuits (e.g., a data storage circuit, a data display circuit, a data transmission circuit) for storing, displaying or transmitting data originating from the sensing element, before or after signal processing in a signal processing circuit. Generally, the ported sensor subassembly 10 (10') comprises one or more data retrieval circuits 30 in electrical communication with the sensing element 50 (e.g., flexural resonator)—either directly or indirectly (e.g., via a signal processing circuit 20). The data retrieval circuit comprises circuitry adapted for storing, displaying or transmitting data. The ported subassembly 10 may, additionally or alternatively, also include one or more signal processing circuits 20 (e.g., an amplifier circuit) for processing (e.g., amplifying) the (previously processed and/or raw) data sensed by the sensing element and/or for processing a data stream from a data retrieval circuit (e.g., a data stream from a stored memory circuit). Further details and particularly preferred embodiments of forming the interfaced sensor from the segmented subassemblies—specifically from the ported subassembly and the installed subassembly, including specific apparatus adapted therefore, are described below, and each of the below-described details are specifically considered in various combination with this and other generally preferred approaches described herein.

Figure 3A:
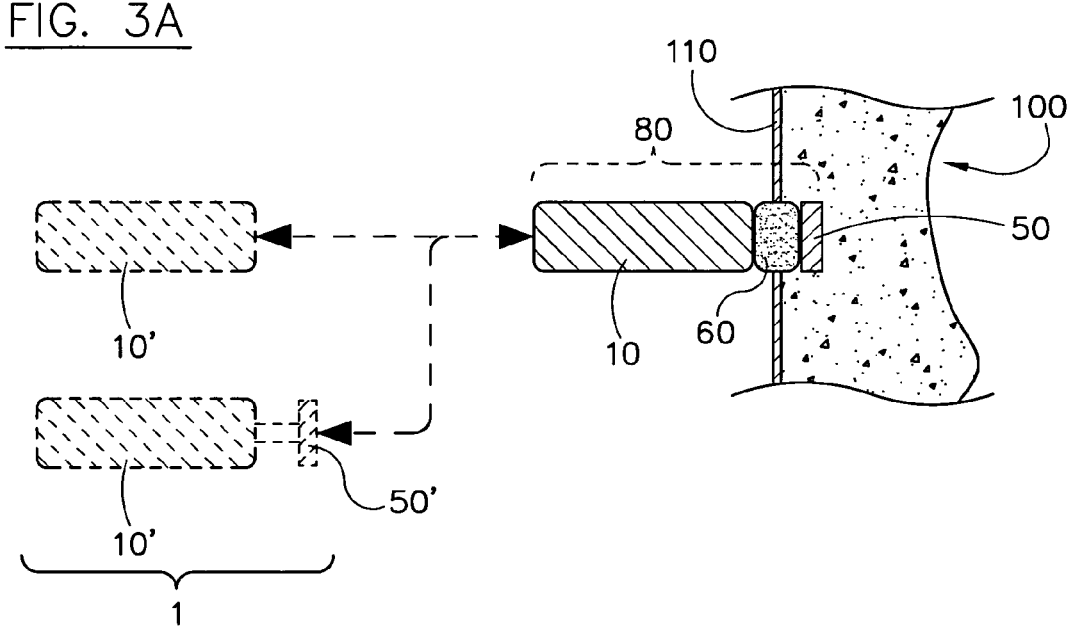

In still a further generally preferred approach of the general method, with reference to FIG. 3A, the ported sensor subassembly 10, or alternatively the ported sensor 1 in its entirety, is interfaced with the (first or second) fluidic system 100 across a physical barrier 110 defining a portion of the fluidic system 100. The physical barrier 110 can include any portion of the physical structure which contains the fluid within the fluidic system. Hence, the barrier 110 can be, for example, the surface (e.g., wall, bottom) of a container, or the surface (e.g., peripheral wall) of a conduit. Preferably, the ported sensor 1 or ported sensor subassembly. 10 is interfaced across the barrier 110 without compromising the integrity of the fluidic system 100. The integrity of the fluidic system is not compromised if the fluidic system remains substantially intact—without substantial loss of fluid material and/or without substantial reduction of fluid pressure during the interfacing step. The amount of lost material or reduced pressure that would be substantial depends generally on the system and operational considerations, but is generally not more than about 10%, preferably not more than about 5%, more preferably not more than about 2% and most preferably not more than about 1%, based on total amount or total absolute pressure, respectively. Further details of interfacing the ported sensor or ported sensor subassembly across the barrier, including specific apparatus adapted for such interfacing, are described below, and each of the below-described details are specifically considered in various combination with this and other generally preferred approaches described herein.

In another generally preferred approach of the general method, with reference to FIG. 3A, the ported sensor 1 or ported sensor subassembly 10 is ported and interfaced, for example as described in any of the aforementioned general methods. The fluid is sensed using the interfaced sensor 80 and the data generated in the sensing step (i.e., whether processed data or raw data) is stored, displayed or transmitted using the data retrieval circuit. One or more of the storing step, the displaying step or the transmitting step comprises communicating with the data retrieval circuit of the ported sensor 1 or ported sensor subassembly 10 using a wireless communication protocol. As used herein, a wireless communication protocol includes at least one transfer of data using electromagnetic radiation. The wireless communication can generally be between the data retrieval circuit of the ported sensor or ported subassembly and an installed sensor/sensor subassembly comprising a sensing element (e.g., a mechanical resonator such as a flexural resonator), and optionally, an installed signal processing circuit (e.g., amplifying circuit) and optionally, an installed (second) data retrieval circuit. Additionally or alternatively, the wireless communication can generally be between the data retrieval circuit of the ported sensor or ported subassembly and a wireless communication receiving circuit at a remote location (e.g., installed in a service truck parked relatively nearby the fluid-sensing location). Further details of wireless communication protocols involving the data retrieval circuit of the ported sensor or ported sensor subassembly, including specific apparatus adapted for such communication, are described below, and each of the below-described details are specifically considered in various combination with this and other generally preferred approaches described herein.

In yet a further generally preferred approach of the general method, with reference to FIGS. 4A and 5A, the ported sensor 1 (1') or ported sensor subassembly 10 (10') is a hand-held (i.e., personally portable) device. The hand-held device can comprise a hand-held sensor (in its entirety) or a hand-held sensor subassembly (e.g., as described above and below in connection with segmented assemblies) and in either case, can be ported by a person to the (first or second) fluidic system at various times as necessary or desired, and in each case, interfaced and used for sensing the fluid, for example as described in any of the aforementioned general methods. Hand-portable sensors or sensor subassemblies provide substantial advantages, including especially for remote field operations and/or for centralized service applications on mobile fluidic systems and/or for monitoring or servicing of complex fluidic systems (having multiple independent fluidic systems) or geometry-constrained (e.g., densely packed) fluidic systems. In these and other applications, hard-configured multiplexing systems may be inefficient and/or cost-prohibitive. In contradistinction, hand-held systems provide the benefits of multiplexing without creating unnecessary and largely unused or underutilized redundancies in sensing systems or components thereof. Further details of using hand-held sensors and hand-held sensor subassemblies in the methods of the present invention, including specific apparatus adapted therefor, are described below, and each of the below-described details are specifically considered in various combination with this and other generally preferred approaches described herein.

Each of the aforementioned generally preferred approaches can be applied independently or in combination with each other, in each of the possible various permutations. Also, each of the aforementioned generally preferred approaches can be applied in further combination with more particular aspects, including particular protocols and/or particular apparatus features, as described below.

Preferred General Systems and Apparatus

The present invention also include devices effective for monitoring fluids in fluidic systems according to the aforementioned methods. In general, such devices are systems or apparatus that comprise one or more sensors, and/or that comprise one or more sensor subassemblies adapted for or configured for interfacing with one or more other sensors/sensor subassemblies to form an interfaced sensor that is operational or that has enhanced operational functionality.

A preferred general system of the invention can comprise an interfaced sensor in a fluidic system, where the interfaced sensor comprises a sensing element, and at least one or both of a data retrieval circuit or a signal processing circuit.

In this respect, with reference to FIG. 2A, in one preferred general embodiment the interfaced sensor 80 of the fluidic system 100 can comprise the sensing element 50 (e.g., a flexural resonator) fixedly attached to the fluidic system 100, and preferably positioned or positionable such that the sensing surface of the sensing element 50 can contact the fluid during operation of the interfaced sensor 80. In this preferred general embodiment, the interfaced sensor 80 can further comprise a portable sensor subassembly 10 (shown as 10' in a removed position) that is removably interfaced with (the sensing element 50 fixedly attached to) the fluidic system 100. The portable, removable sensor subassembly 10 comprises a data retrieval circuit adapted for or configured for electrical communication with the sensing element—directly, or indirectly (as noted above)—for storing, displaying or transmitting (raw or processed) data. The interfaced sensor 80 can alternatively or additionally, further comprise one or more signal processing circuits for processing the (raw or previously processed) data. Further details of this preferred general embodiment, including specific subassemblies thereof and uses thereof are described herein (above and below), and each of the herein-described details are specifically considered in combination with this and other generally described features of the systems and apparatus.

In another preferred general embodiment, with reference to FIG. 3A, the interfaced sensor 80 of the fluidic system 100 can further comprise a mechanical or electrical coupling 60 adapted or configured such that the sensor 1 (shown in the removed position) or sensor subassembly 10 (shown as 10' in a removed position) can be removably engaged with the fluidic system 100 for operation of the interfaced sensor 80, but without compromising the integrity of the fluidic system 100 (as discussed above in connection with the method). Further details of this preferred general embodiment, including specific couplings uses thereof are described herein (above and below), and each of the herein-described details are specifically considered in combination with this and other generally described features of the systems and apparatus.

The invention is also directed to various apparatus for use (alone or as part of a monitoring system) in monitoring a property of a fluid in a fluidic system using one or more flexural resonators.

In one generally preferred embodiment, with reference to FIGS. 3A and 4A, such an apparatus can comprise a portable sensor subassembly 10 (10') (e.g., preferably a hand-held sensor subassembly), that can interface with a flexural resonator sensing element 50 that is pre-installed in the fluidic system 100. The hand-held sensor subassembly 10 can comprise a signal processing circuit 20 adapted for electrical communication with one or more flexural resonators sensing elements 50, and being adapted for or configured for at least receiving an input signal from the one or more flexural resonators during a sensing period and processing the received signal to generate data associated with one or more properties of the fluid. Optionally, the hand-held subassembly 10 can further comprise signal processing circuitry 20 adapted for and configured for providing a stimulus to the flexural resonator sensing element 50. The hand-held subassembly 10 further comprises, a data retrieval circuit 30 in electrical communication with the signal processing circuit 20, for storing, displaying or transmitting the generated data. Further details of this preferred general embodiment, including specific features thereof and uses thereof are described herein (above and below), and each of the herein-described details are specifically considered in combination with this and other generally described features of the systems and apparatus.

In another generally preferred embodiment, with further reference to FIGS. 3A, 4A and 5A, such an apparatus comprises a hand-held sensor 1 or hand-held sensor subassembly 10 (10'), in each case adapted for or configured for being removably coupled with the fluidic system 100. The hand-held sensor 1 or hand-held sensor subassembly 10' comprises a flexural resonator sensing element 50 having a sensing surface adapted for or configured for contacting a fluid. Preferably, but optionally, the hand-held sensor 1 or hand-held sensor subassembly 10 of this embodiment further comprises a data retrieval circuit 30 in electrical communication with the flexural resonator, for storing, displaying or transmitting data. Preferably, but optionally, the hand-held sensor 1 or hand-held sensor subassembly 10 of this embodiment further comprises a signal processing circuit 20 in electrical communication with the flexural resonator, for storing, displaying or transmitting data. Further details of this preferred general embodiment, including specific features thereof and uses thereof are described herein (above and below), and each of the herein-described details are specifically considered in combination with this and other generally described features of the systems and apparatus.

Figure 6A:
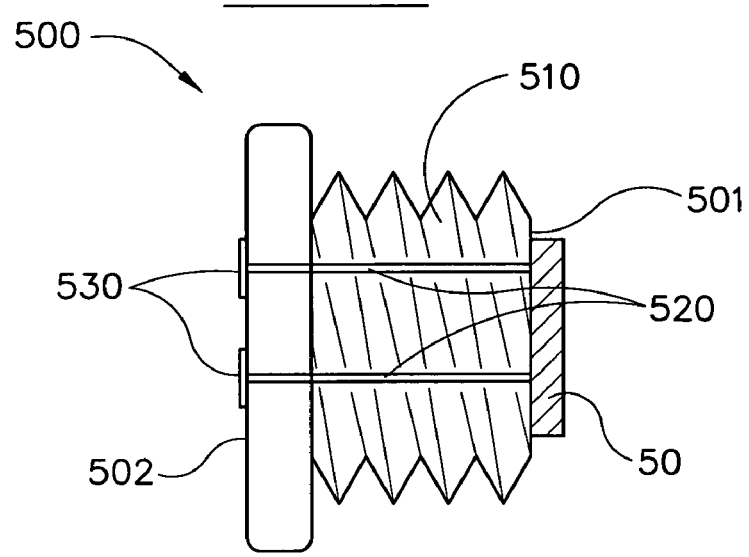
FIGS. 6A and 6B are section views of some preferred apparatus of the invention.

In another generally preferred embodiment, with reference to FIGS. 3A and 6A, such an apparatus can comprise a plug 500 having a body 510 adapted for removable engagement with the fluidic system 100, e.g, such as a fluid reservoir of the fluidic system 100, and a flexural resonator sensing element 50 mounted on a first surface 501 of the plug and having a sensing surface for contacting the fluid in the fluid reservoir or other portion of the fluidic system 100. The plug 500 is further adapted for or configured for electrical communication (e.g., hard-wired or wireless communication protocols) between the flexural resonator sensing element 50 and one or both of a signal processing circuit or a data retrieval circuit. Preferably, for example, the plug 500 can comprise one or more conductive paths 520 extending through the plug and providing electrical communication between the flexural resonator sensing element 50 and one or more contacts 530 on a second surface 502 of the plug, such that a portable sensor subassembly 10 can be interfaced with an installed flexural resonator sensing element 50 through the one or more contacts 530. In this aspect, the plug 500 can operate as a mechanical or electrical coupling 60. The plug 500 can additionally or alternatively further comprise a temperature sensor mounted on or fluidically near the first surface 501 of the plug, and one or more conductive paths extending through the plug and providing electrical communication between the temperature sensor and one or more contacts on the second surface of the plug. Further details of this preferred general embodiment, including specific features thereof and uses thereof are described herein (above and below), and each of the herein-described details are specifically considered in combination with this and other generally described features of the systems and apparatus.

Figure 6B:
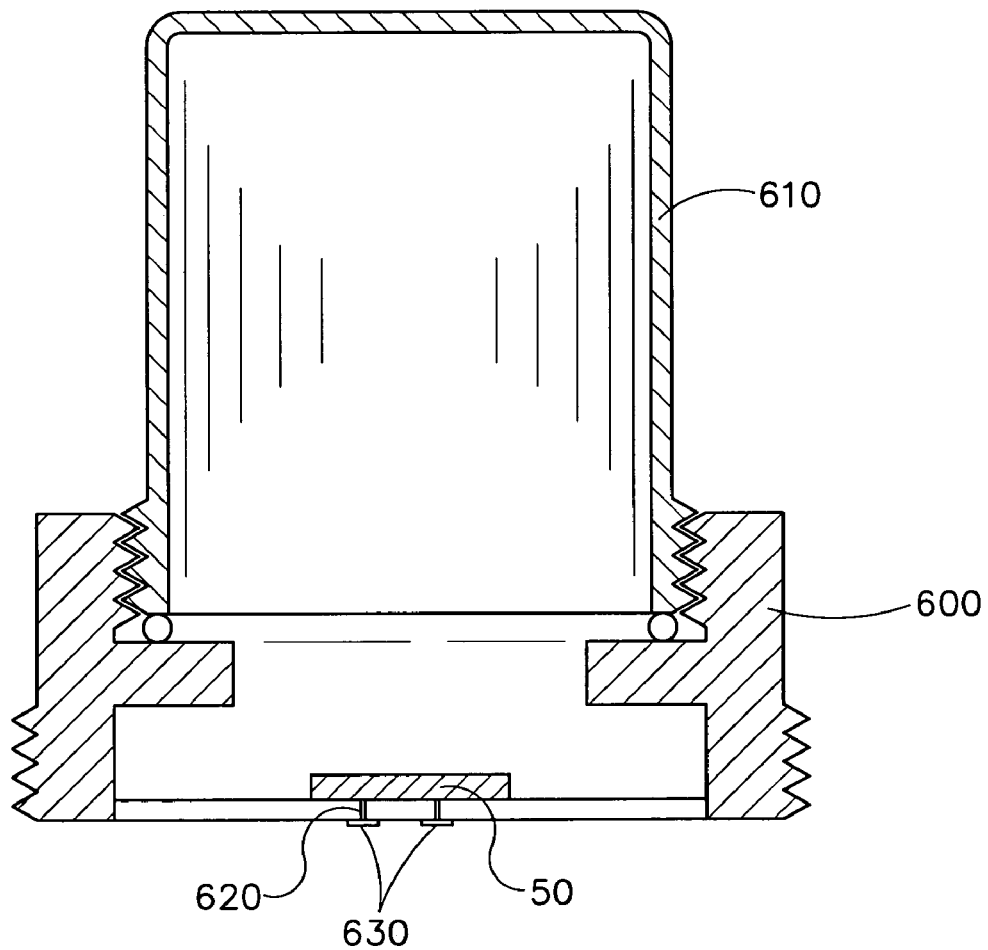

In another preferred general embodiment of such an apparatus for use in monitoring a property of a fluid in a fluidic system, the apparatus comprises, with reference to FIGS. 3A and 6B, a structure 600 supporting a fluid filter 610 and adapted for engagement with the fluidic system 100, and a flexural resonator sensing element 50 mounted on or integrated with the support structure 600. The support structure 600 is adapted for or configured for providing electrical communication between the flexural resonator sensing element 50 and a data retrieval circuit (not shown). Preferably, the apparatus can further comprise one or more conductive paths 620 providing electrical communication between the flexural resonator sensing element 50 and one or more contacts 630 on an accessible surface of the support structure 600, such that a portable sensor subassembly 10 can be interfaced with the flexural resonator sensing element 50 through the one or more contacts 630. In this aspect, the supporting structure 600 can operate as a mechanical and/or electrical coupling 60. In these preferred embodiments, the apparatus can further comprise a temperature sensor mounted on or integrated with the support structure 600, and one or more conductive paths providing electrical communication between the temperature sensor and one or more contacts the accessible surface of the support structure 600. Further details of this preferred general embodiment, including specific features thereof and uses thereof are described herein (above and below), and each of the herein-described details are specifically considered in combination with this and other generally described features of the systems and apparatus.

Each of the aforementioned generally preferred systems or apparatus can be applied independently or in combination with each other, in each of the possible various permutations. Also, each of the aforementioned generally preferred approaches can be applied in further combination with more particular aspects, including particular methodology protocols and/or particular apparatus features, as described above and/or below.

Monitoring of Fluidic Systems

In each of the aforementioned generally preferred approaches and/or embodiments, the fluidic system can be, with respect to the fluid, an open fluidic system or a closed fluidic system. An open fluidic system can comprise one or more fluids and having one or more fluidic surfaces that are exposed to an open uncontrolled atmosphere. For example, an open fluidic system can be an open container such as an open-top tank or an open well of a batch reactor or of a parallel batch reactor (e.g., microtiter plate). Alternatively, the fluidic system can be a closed fluidic system. A closed fluidic system can comprise one or more fluids that are generally bounded by a barrier so that the fluids are constrained. For example, a closed fluidic system can include a pipeline (e.g., for oil and/or gas transport) or a recirculating fluidic system, such as an oil system associated with an engine, or a refrigerant or coolant system associated with various residential, commercial and/or industrial applications. A closed fluidic system can be in fluid communication with an open fluidic system. The fluid communication between a closed fluidic system and an open fluidic system can be isolable, for example, using one or more valves. Such isolation valves can configured for uni-directional fluid flow, such as for example, a pressure relief valve or a check valve. In general, the fluidic system (whether open or closed) can be defined by manufactured (e.g., man-made) boundaries comprising one or more barriers. The one or more barriers defining manufactured boundaries barriers can generally be made from natural or non-natural materials. Also, in general, the fluidic system (whether open or closed) can be a flow system such as a continuous flow system or an intermittent-flow system, a batch system, or a semi-batch system (sometimes also referred to as a semi-continuous system). In many instances, fluidic systems that are flow systems are closed fluidic systems. The fluidic systems, whether fluidically-open fluidic systems or fluidically-closed fluidic systems as described above, can be open systems or closed systems with respect to heat transfer. Hence, the systems, considered as a whole or in relevant portion thereof, can be heat releasing fluidic systems, heat absorbing fluidic systems or adiabatic systems.

In particular, for example, mechanical resonators such as flexural resonators can be used in connection with liquids or gasses having a wide range of fluid properties, such as a wide range of viscosities, densities and/or dielectric constants (each such property being considered independently or collectively as to two or more thereof). For example, liquid fluids can generally have viscosities ranging from about 0.1 cP to about 100 000 cP, and/or can have densities ranging from about 0.0005 g/cc$^3$ to about 20 g/cc$^3$ and/or can have a dielectric constant ranging from about 1 to about 100. Gaseous fluids can, for example, generally have viscosities ranging from about 0.001 to about 0.1 cP, and/or can have densities ranging from about 0.0005 to about 0.1 g/cc$^3$ and/or can have a dielectric constant ranging from about 1 to about 1.1. The fluids can be ionic fluids or nonionic fluids. As an example, ionic fluids can have a conductivity ranging from about 1 (Ohm-cm)$^{-1}$ to about 1 (GOhm-cm)$^{-1}$. The fluids of the invention can include relatively pure liquid or gaseous elements (e.g., liquid $N_2$, gaseous $O_2$, gaseous or liquid $H_2$) or relatively pure liquid or gaseous compounds (e.g., liquid $H_2O$, gaseous $CH_4$). The fluids of the inventions can also be single-phase or multi-phase mixtures of gases, liquids and/or solids, including for example: mixtures of gasses; mixtures of liquids (e.g., solutions); two-phase mixtures of a first liquid and a second liquid (e.g., liquid-liquid emulsion); two-phase mixtures of liquids and gasses (e.g., a liquid having gas sparging or bubbling, e.g, a liquid nebulized through a gaseous environment); two-phase mixtures of liquids and solids (e.g, colloidal solutions; dispersions; suspensions); two-phase mixtures of solids and gases (e.g., fluidized bed systems); and/or three-phase mixtures of gasses, liquids and solids. Particular examples of preferred fluids are described herein, including in discussion below regarding preferred applications of the methods and devices of the invention.

The operating conditions of the fluid in the fluidic system is not narrowly critical to the invention. Generally, the fluids within a particular fluidic system and/or fluids in different fluidic systems can have widely varying process conditions, such as temperature, pressure flowrate. Generally, the temperature can range from about or below the freezing point of the fluid to above the vaporization temperature, including for example to superheated temperatures and/or for supercritical fluids. Particular temperature ranges can be preferred for particular fluids. Generally, the pressure within a fluidic system can likewise cover a wide range, including for example ranging from about vacuum conditions to about 25,000 psig. In preferred applications, the pressure can be lower, ranging from vacuum conditions to about 15,000 psig, from vacuum conditions to about 10,000 psig, from vacuum conditions to about 5,000 psig, from vacuum conditions to about 1,000 psig, from vacuum conditions to about 500 psig, or from vacuum conditions to about 100 psig. In an alternative embodiment, the pressure range in each of the aforementioned ranges can have lower pressure limit of about 1 psig or about 10 psig or about 20 psig.

In the methods and systems and apparatus of the invention, the particular property being monitored is not narrowly critical. In general, the property of interest will depend on the fluid and the significance of the monitoring with respect to a particular fluidic system in a particular commercial application. The property being monitored for a particular fluidic system may also depend to some extent on the type of sensor. Significantly, some properties of fluids (both liquids and gasses) are of general importance across a wide range of commercial applications. For example, the viscosity of a fluid is of near universal interest for many fluidic systems. Likewise, the density of a fluid is also of great general interest for many fluidic systems. It is especially advantageous to be able to monitor both viscosity and density of a fluid—based on the same monitoring event (e.g., concurrently or simultaneously, using the same sensing element, on the same fluid sample). Significantly, flexural resonators such as tuning forks, unimorphs (e.g, disc benders), bimorphs, torsional resonators, etc. have been demonstrated by Matsiev et al. to have the capability of such concurrent or simultaneous monitoring of both viscosity and density. See Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is incorporated by reference herein for all purposes, and see also commonly-owned U.S. Pat. Nos. 6,401,519; 6,393,895; 6,336,353; 6,182,499; 6,494,079 and EP 0943091 B1, each of which are incorporated by reference herein for all purposes. Dielectric constant is also a very significant property of interest for many commercial applications—particularly for applications involving ionic liquids. See Id. Other properties can also be of interest, alternatively to or in addition to the aforementioned properties. For example, temperature and/or pressure and/or flow rate are similarly of near-universal interest across a wide range of commercial applications. Parallel resistance can also be of interest.

In general, as noted above, the particular sensor of the methods and systems and apparatus of the present invention is not limited. Generally, the sensors useful in connection with this invention are adapted to monitor one or more properties of a fluid—that is, to generate data associated with one or more properties of the fluid. The data association with a property in this context means data (typically obtained or collected as a data stream over some time period such as a sensing period), including both raw data (directly sensed data) or processed data, can be directly informative of or related to (e.g., through correlation and/or calibration) an absolute value of a property and/or a relative value of a property (e.g., a change in a property value over time). In many applications, the raw data can be associated to a property of interest using one or more correlations and/or using one or more calibrations. Typically such correlations and/or calibrations can be effected electronically using signal processing circuitry, either with user interaction or without user interaction (e.g., automatically).

Particular sensors can be selected based on needed or desired property (or properties) of interest, and on required specifications as to sensitivity, universality, fluid-compatability, system-compatability, as well as on business considerations such as availability, expense, etc. Because of the substantial universal nature of viscosity and/or density and/or dielectric properties for many diverse fluidic systems, sensors that are suited for monitoring these properties are preferred. There are many sensors known in the art for measuring one or more of viscosity, density and/or dielectric. Accordingly, the selection of one or more of such sensor types is not critical to the invention.

Preferably, the sensor is a mechanical resonator sensor. The mechanical resonator can include, for example, flexural resonators, surface acoustic wave resonators, thickness shear mode resonators and the like. Various types of flexural resonators can be employed, including for example tuning forks, cantilevers, bimorphs, unimorphs, membrane resonators, disc benders, torsion resonators, or combinations thereof. Flexural resonator sensing elements comprising tuning fork resonators are particularly preferred. The tuning fork resonator can have two tines (e.g., binary-tined tuning fork) or more than two tines, such as three tines (e.g., a trident tuning fork) or four tines (e.g., a quaternary-tined tuning fork). In some applications, a tuning fork resonator may be configured (e.g., with respect to geometry and electrode configuration) for resonating within a single plane. For some applications, a tuning fork may be may be configured (e.g., with respect to geometry and electrode configuration) for resonating in two or more different planes relative to each other, such as in two planes perpendicular to each other.

Such flexural resonator sensors are well known in the art. See Matsiev, "*Application of Flexural Mechanical Resonators to Simultaneous Measurements of Liquid Density and Viscosity*," IEEE International Ultrasonics Symposium, Oct. 17-20, 1999, Lake Tahoe, Nev., which is incorporated by reference herein for all purposes, and see also commonly-owned U.S. Pat. Nos. 6,401,519; 6,393,895; 6,336,353; 6,182,499; 6,494,079 and EP 0943091 B1, each of which are incorporated by reference herein for all purposes. More recent advances include those described in co-pending applications, such as U.S. Ser. No. 10/452,264 entitled "Machine Fluid Sensor And Method" filed on Jun. 2, 2003 by Matsiev et al (co-owned, describing applications involving flexural resonator technologies in machines, such as transportation vehicles); U.S. Ser. No. 60/505,943 entitled "Environmental Control System Fluid Sensing System and Method" filed on Sep. 25, 2003 by Matsiev et al. and related PCT Application No. PCT/US03/32983 entitled "Environmental Control System Fluid Sensing System and Method" filed on Oct. 17, 2003 by Matsiev et al (each co-owned, describing applications involving flexural resonator technologies in heating, ventilation, air-conditioning and refrigeration systems and in machines such as engine systems related thereto); U.S. Appl. No. 2002/0178805 A1(describing applications involving flexural resonator technologies in down-hole oil well applications such as well-logging systems); U.S. Ser. No. 10/804,446 entitled "Mechanical Resonator" filed on Mar. 19, 2004 by Kolosov et al. (co-owned, describing various advantageous materials and coatings for flexural resonator sensing elements); U.S. Ser. No. 10/804,379 entitled "Resonator Sensor Assembly" filed on Mar. 19, 2004 by Kolosov et al., and PCT Application. No. PCT/US04/08552 entitled "Resonator Sensor Assembly" filed on Mar. 19, 2004 by Kolosov et al. (each co-owned, describing various advantageous packaging approaches for applying flexural resonator technologies); and U.S. Ser. No. 10/394,543 entitled "Application Specific Integrated Circuitry For Controlling Analysis For a Fluid" filed on Mar. 21, 2003 by Kolosov et al., and PCT Application. No. PCT/US04/008555 entitled "Application Specific Integrated Circuitry For Controlling Analysis For a Fluid" filed on Mar. 19, 2004 by Kolosov et al. (each co-owned, describing electronics technologies involving application-specific integrated circuit for operating flexural resonator sensing elements), each of which are incorporated herein by reference for all purposes, and each of which includes descriptions of preferred embodiments for flexural resonator sensors and use thereof in connection with the methods and apparatus and systems of the present invention. Further details regarding flexural resonator sensors and/or flexural resonator sensing element are described below, but are generally applicable to each approach and/or embodiment of the inventions disclosed herein.

Although much of the description is presented herein in the context of flexural resonator sensors, various aspects of the invention are not limited to such sensors.

Hence, other types of sensors (or sensor subassemblies) can also be used in place of mechanical resonators.

In addition, other sensors (or sensor subassemblies) can be used in combination with the mechanical resonator sensor or other types of sensors mentioned above. Particularly preferred sensors for use in combination with mechanical resonators, such as flexural resonators, include temperature sensors, pressure sensors, flow sensors, conductivity sensors, thermal conductivity sensors, among others.

The methods and systems and apparatus of the invention can be used to monitor fluidic systems for various purposes. The inventions can be advantageously used, for example, to monitor fluids in any of the following field applications: materials or process research, materials or process development, materials or process quality assurance (QA), process monitoring/evaluation, process control, and service applications involving any of the foregoing.

Further details of preferred fluidic systems, fluids, properties, sensors and monitoring, including specific methodology approaches and apparatus features thereof are described herein (above and below), and each of the herein-described details are specifically considered in various combinations and permutations with the generally described aspects in this subsection of the specification.

Porting

As described above in connection with the generally preferred approaches, systems, and apparatus (e.g., in connection with FIG. 1), the sensor or a sensor subassembly is ported to one or more locations on one or more fluidic systems for interfacing with such systems. Later (e.g., after sensing), the sensor or sensor subassembly is disinterfaced and the ported away from that location of the fluidic system, and typically then ported again (re-ported) to a second location, a second fluidic system or to the same location, but at a later time.

The particular manner in which the sensor or sensor subassembly is ported is not critical to the invention, however. The sensor or sensor subassembly is preferably a portable sensor or portable sensor subassembly that can be ported (e.g., carried or otherwise moved) manually (e.g., personally-ported as a personally ported/hand-held sensor or a personally-ported/hand-held sensor subassembly). A hand-held unit (i.e., synonymously, a personally-ported unit) can be carried on a persons body, and can include for example a unit adapted to be physically held by a person's hand or otherwise positioned on a person's body (e.g., on a person's wrist, using for example a wrist-band, on a person's arm, using for example an arm-band, on a person's waist, using for example a waist-belt, on a person's shoulder's or back, using for example a back-pack such as a framed back-pack assembly, etc.) The sensor or sensor subassembly can also be ported mechanically (e.g., with the use of a mechanical implement such as a manually-operated mechanical system) and/or robotically (e.g., with the use of an automated robotic-controlled system).

In some embodiments, the sensor or sensor subassembly can be ported fluidically, for example, using hydraulic or pneumatic porting approaches. In one example, a ported sensor subassembly could be internal to (i.e., within a fluidic system) rather than external to (i.e., outside of a fluidic system)—such as for example in a long (e.g., transnational) pipeline having installed (fixed) sensing elements at various locations along the pipeline, and having a ported sensor subassembly flowing in the fluid within the pipeline, and generally interfacing with the installed sensing elements via transmission circuitry both installed locally on the pipeline and installed within the ported sensor subassembly.

Interfacing a Ported Sensor Subassembly—Segmented Sensor Functionality

As described above in connection with the generally preferred approaches, systems, and apparatus (e.g., in connection with FIGS. 1, 2A and 3A), the ported sensor subassembly is interfaced with one or more fluidic systems to form an interfaced sensor. The interfaced sensor is operational for monitoring a property of a fluid within the fluidic system. The fluid property can be monitored in real time, in near real time, or in time-delayed modes of operation.

With further reference to FIGS. 2A and 4A, in one approach, the ported sensor subassembly 10 comprises one or both of a data retrieval circuit or a signal processing circuit, to be interfaced with an already-installed sensor or sensor subassembly that comprises a sensing element 50. Alternatively, in another approach (not shown in FIG. 2A or 4A), the ported sensor subassembly comprises a sensing element to be interfaced with an already-installed sensor subassembly that comprises one or both of a data retrieval circuit or a signal processing circuit.

Figure 2B:
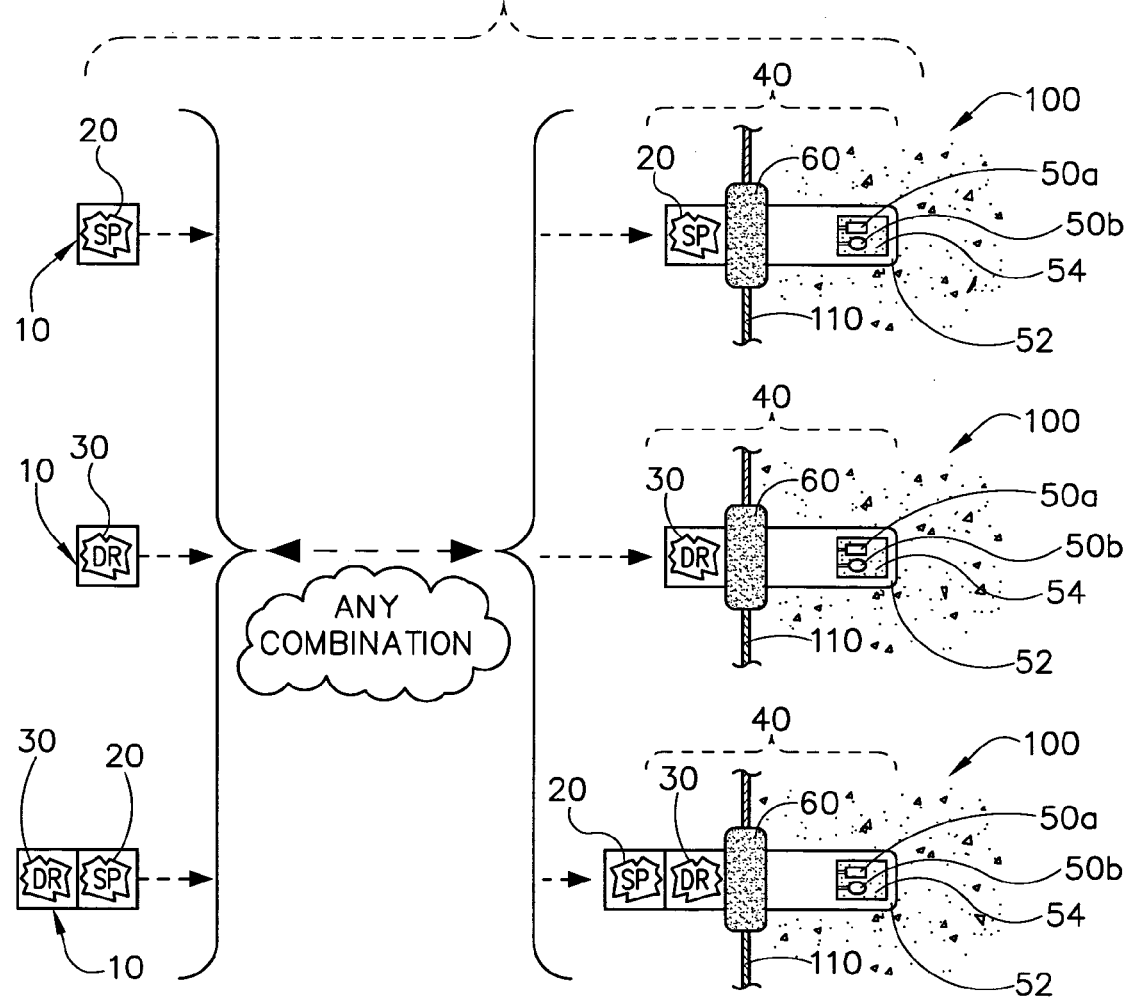

With reference to FIG. 2B, it can be appreciated that a ported sensor subassembly 10 having a variety of internal configurations can be interfaced with an already-installed sensor/sensor subassembly 40 also having a variety of configurations, to form an interfaced sensor (not shown in FIG. 2B, but indicated in a removed (disinterfaced) form as 80').

In particular, the preinstalled sensor/sensor subassembly 40 can comprise one or more sensing elements 50a, 50b (e.g., a flexural resonator and a temperature sensing element, in combination), optionally situated in a sensing element housing 52 such that a sensing surface of the sensing elements 50a, 50b can be exposed to the fluid (e.g., via housing window 54). Optionally the preinstalled sensor/sensor subassembly 40 can further comprise either or both of a signal processing circuit 20 (indicated as "SP") or a data retrieval circuit 30 (indicated as "DR") in electrical communication with the one or more sensing elements, and preferably in electrical communication with each other as appropriate. The installed sensor/sensor subassembly 40 can also optionally comprise a coupling 60 providing electrical or mechanical access across the barrier. The particular location of the signal processing circuitry 20 and/or data retrieval circuitry 30 of the installed sensor/sensor-subassembly 40 is not critical. In some embodiments (e.g., in applications involving high-temperature and/or flammable fluids), it may be advantageous to provide the preinstalled circuitry 20, 30 external to the fluidic system (e.g., fixedly mounted on a surface of barrier 110 opposing the fluid-side surface of the barrier 110), for example as shown in FIG. 2B, and in electrical communication with one or more of the sensors 50a, 50b. In other embodiments the circuitry 20, 30 can be mounted on the fluid-side surface of the barrier 110.

The ported sensor subassembly 10 can likewise comprise either or both of a signal processing circuit 20 (indicated as "SP") or a data retrieval circuit 30 (indicated as "DR"). The ported sensor subassembly is preferably adapted for providing, upon interfacing to the fluidic system, electrical communication with the one or more of sensing elements 50a, 50b, signal processing circuitry 20, or data retrieval circuitry 30, in each case of the installed sensor/sensor subassembly 40.

Hence, FIG. 2B schematically represents nine combinations of schema for interfacing segmented portions of an interfaced sensor. Since, as discussed herein (above and below), the signal processing circuit 20 and the data retrieval circuit 30 can each include multiple circuits of different functionality, an even higher number of more specific combinations are represented in FIG. 2B, and all such combinations and permutations are contemplated as being within the scope of the invention. Notably, in view of the aforedescribed various combinations of which sensor components are included in the preinstalled sensor/sensor subassembly 40, the preinstalled unit can be a preinstalled sensor that already has operational sensing capability alone (prior to interfacing of the ported subassembly with the fluidic system). In this case, the ported sensor subassembly 10 can provide additional functionality to the preinstalled sensor 40. As one preferred example, the preinstalled sensor 40 can comprise a sensing element (e.g., a flexural resonator), a signal processing circuit 20 (e.g., comprising amplifier circuitry), and a data retrieval circuit 30 (e.g. comprising data memory circuitry, perhaps adapted for recording raw data received from the sensing element). A ported sensor subassembly can include, in this preferred example, a signal processing circuit (e.g., for importing the stored raw data and processing the same) and/or a data retrieval circuit (e.g., for storing the processed data and/or for transmitting the processed data). In an alternative case, the preinstalled unit can be a sensor subassembly 40 that obtains operational sensing capability only upon interfacing of the ported subassembly 10 with the fluidic system 100.

In preferred embodiments involving an interfaced sensor formed from a segmented sensor subassembly, the fluidic system can comprise one or more installed sensing elements 50a, 50b (e.g., flexural resonator sensing element), and also an installed data retrieval circuit 30. The data retrieval circuit 30 can comprise data display circuitry such as a light (e.g., an light-emitting diode (LED)) for indicating a status of a fluid under test) or such as a readout (e.g., an LED readout display) or such as a graphical user interface (e.g., computer monitor). The ported sensor subassembly can comprise a signal processing circuitry 20, such that a sensing period can be initiated by a person interfacing the ported signal processing circuitry 20 with the installed sensor/sensor subassembly 40. The person can then read out some information locally from the display circuitry. Based on the read-out information, the person can take some further action, such as reporting a status, or changing a condition of the fluid or of the fluidic system. Particular down-stream processing and/or further actions are also discussed below.

In an alternative preferred embodiment involving an interfaced sensor formed from a segmented sensor subassembly, the fluidic system can comprise one or more installed sensing elements 50a, 50b (e.g., flexural resonator sensing element), and also an installed signal processing circuit 20. The signal processing circuit 20 can comprise signal conditioning circuitry and data derivation circuitry. The ported sensor subassembly can comprise a data display circuitry such as a light (e.g., an light-emitting diode (LED)) for indicating a status of a fluid under test) or such as a readout (e.g., an LED readout display) or such as a graphical user interface (e.g., computer monitor). In operation, a sensing period can be initiated or can be observed (if an ongoing, already-in-progress sensing operation) by a person interfacing the ported data display circuitry with the installed sensor/sensor subassembly 40. The person can then read out some information locally from the display circuitry. Based on the read-out information, the person can take some further action, such as reporting a status, or changing a condition of the fluid or of the fluidic system. Particular down-stream processing and/or further actions are also discussed below.

In a further alternative preferred embodiment involving an interfaced sensor formed from a segmented sensor subassembly, the fluidic system can comprise one or more installed sensing elements 50a, 50b (e.g., flexural resonator sensing element), and both an installed signal processing circuit 20, and an installed data retrieval circuitry. For example, the installed signal processing circuit 20 can comprise signal conditioning circuitry and data derivation circuitry. The installed data retrieval circuitry can comprise a data storage circuit including memory for capturing raw data stream or a data stream generated by the signal processing circuit (e.g., a conditioned data stream or a derived data stream). In this embodiment, the ported sensor subassembly can comprise a further data retrieval circuit, such as a data display circuitry and/or a data storage circuit. In such a case, in operation, collected data residing in the installed memory circuit can be transmitted to and either displayed in or stored in the ported unit, for later collection and/or analysis at a remote data repository. For example, the ported sensor subassembly could be a memory stick (jump drive), and the data just transferred to a remote data repository via such memory stick (jump drive). The same or other person can then read out some information remotely from the repository. Based on the read-out information, the person can take some further action, such as reporting a status, or changing a condition of the fluid or of the fluidic system. Particular down-stream processing and/or further actions are also discussed below.

Figure 2C:
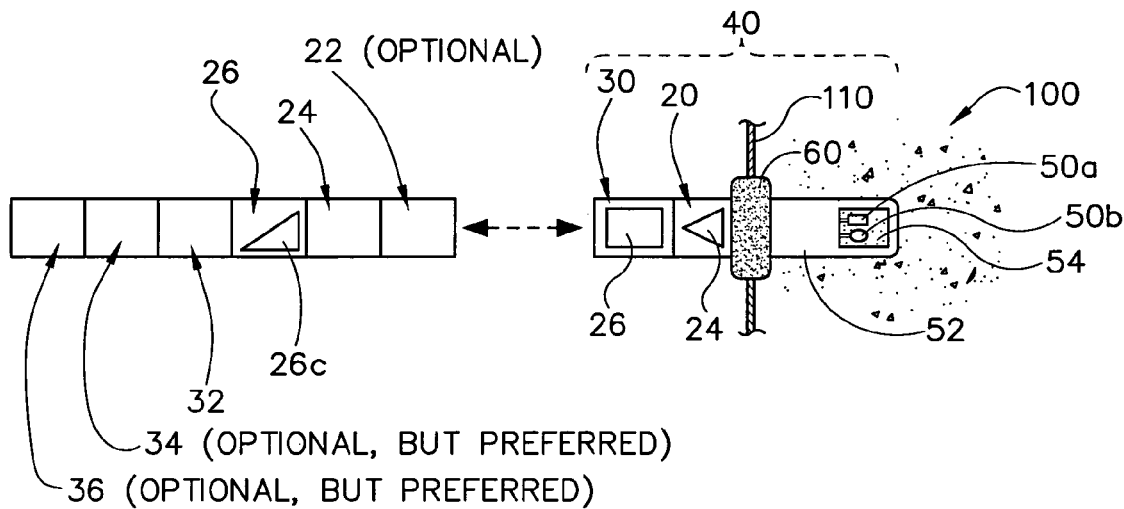

In a particularly preferred embodiment, shown schematically in FIG. 2C, the installed subassembly 40 comprises a first sensing element 50a that is a flexural resonator (e.g., a tuning fork resonator) and a second sensing element 50b that is a temperature sensing element (e.g., an RTD detector or a thermistor). The installed subassembly 40 further comprises a set of conductive paths (not shown) providing electrical communication through the barrier 110 via an electrical coupling 60 to a signal processing circuit 20, preferably situated on the external side of the barrier 110 of the fluidic system 100 (e.g., mounted on the external side of the coupling 60, as shown). The signal processing circuit 20 of this particularly-preferred embodiment includes a signal conditioning circuit 24 that comprises (or in some embodiments consists essentially of) an amplifier circuit comprising one or more amplifiers or one or more preamplifiers, effective for or configured for amplifying one or more input signals received from one or both of the sensing elements 50a, 50b, including preferably at least an input signal received from the flexural resonator sensing element 50a. The ported sensor subassembly 10 of this particularly-preferred embodiment preferably comprises at least a data retrieval circuit 30, but most preferably comprises both a signal processing circuit 20 and a data retrieval circuit 30.

In an especially preferred embodiment, the embodiment described in the immediately preceding paragraph in connection with FIG. 2C can further comprise, in the installed subassembly 40, an installed memory media, preferably such as a signal-processing memory as an accessible portion of a signal conditioning circuit 24 (not shown) and/or as an accessible portion of a data derivation circuit 26 (as shown) and/or as data storage circuit 32 (not shown). In a preferred approach, for example, the memory media can comprise electronic data storage media, such as non-volatile memory (e.g., ROM, PROM, EE-PROM, FLASH memory etc.), and can typically be pre-loaded with and/or accessible for loading user-defined data (e.g., calibration data, correlation data, data defining approximated fluid properties) as well as pre-loaded and/or accessible for loading user defined data that is system-specific information and/or sensing-element specific information, in each case such as an identifying indicia. The ported sensor subassembly 10 of this particularly-preferred embodiment preferably comprises both a signal processing circuit 20 and a data retrieval circuit 30. The signal processing circuit 20 can comprise, with further reference to FIGS. 4B and 4C and the discussion below relating thereto, an optional signal activation circuit 22, a signal conditioning circuit 24 and a data derivation circuit 26, wherein the data derivation circuit 26 comprises microprocessor circuitry 26c configured for processing data originating from the one or both of the flexural resonator sensing element 50a and/or the temperature sensing element 50b in conjunction with user-defined data (e.g., calibration data) accessible from the installed memory media. The data retrieval circuit 30 of the ported sensor subassembly 10 of this particularly preferred embodiment preferably comprises, with further reference to FIGS. 4B and 4C, at least a data storage circuit 32 and preferably also either or both of a data display circuit 34 or a data transmission circuit 36.

Interfacing Across a barrier

As described above in connection with the generally preferred approaches, systems, and apparatus (e.g., in connection with FIGS. 1, 2A and 3A), the ported sensor or ported sensor subassembly can be interfaced with the fluidic system across a barrier that defines at least a portion of the fluidic system. Preferably, the ported sensor the sensor or sensor subassembly is interfaced across the barrier without substantially compromising the integrity of the fluid system.

With further reference to FIGS. 3A through 3D, a ported sensor subassembly 10 can be interfaced with a fluidic system 100 across a barrier 110 using a coupling 60. The coupling 60 can generally be a mechanical coupling, an electrical coupling and/or a magnetic coupling. In one approach, the coupling 60 can comprise one or more bodies 62 having a first surface 63 on the internal fluid-side of the barrier 110, and an opposing second surface 64 on the external side of the barrier 110. The coupling 60 and/or the body 62 can be affixed to (e.g., fixedly mounted on, fixedly attached to) the barrier 110. Alternatively, the coupling 60 and/or the body 62 can be integrally formed with the barrier 110. The coupling 60 and/or the body 62 and/or a component of the coupling and/or the body can alternatively be removably engaged with the barrier 110. In any case, the coupling 60 and/or the body 62 can comprise one or more components (e.g. circuit modules) that are installed components of the fluidic system, and/or one or more components (e.g., circuit modules) that are components of the ported sensor 1 or ported sensor subassembly 10 and which are functional as coupling components when the ported sensor or ported sensor subassembly are interfaced with the fluidic system.

As shown in FIG. 3B, the coupling 60 can further comprise one one or more conductive paths 66a, 66b (e.g., including wired electrical leads) extending through the body 62 between the first surface 63 and the second surface 64 thereof. The one or more conductive paths 66a, 66b can each have corresponding end terminals 67a, 67b, 67c, 67d preferably exposed at one or more surfaces 63, 64 of the body 62. The conductive path terminals 67a, 67b, 67c, 67d can be adapted for electrical connection with another component such as a sensing element 50 (not shown), signal processing circuitry (not shown) and/or data retrieval circuitry (not shown). The terminals 67a, 67b, 67c, 67d can comprise, for example, contact pins or contact pads.

FIG. 3C shows another example, in which the coupling 60 can comprise a body 62 comprising one or more communication circuitry modules 68a, 68b adapted for transmitting and/or receiving (e.g., transceiving) electromagnetic radiation (e.g., microwave, infrared, radio-frequency (RF), optical, etc.) and/or for transmitting and/or receiving magnetic fields through the body 62 between the first surface 63 and the second surface 64 thereof. The one or more communication circuitry modules 68a, 68b can optionally each have corresponding terminals 69a, 69b preferably exposed at one or more surfaces 63, 64 of the body 62. The terminals 69a, 69b of the communication circuitry modules 68a, 68b can be adapted for electrical connection with another component such as a sensing element 50 (not shown), signal processing circuitry (not shown) and/or data retrieval circuitry (not shown). The terminals 69a, 69b can comprise, for example, contact pins or contact pads.

In FIG. 3D, an alternative embodiment is shown where the coupling 60 comprises an integral region of the barrier 110 of the fluidic system 100, generally indicated as 70, and optionally defined by one or more markings 71 on barrier 110. For example, the one or more markings 70 could indicate a region on a first surface 111 on the internal fluid-side of the barrier 110 (no marking shown), and/or on an opposing second surface 112 on the external side of the barrier 110 (shown as marking 71). The coupling 60 of FIG. 3D can further comprise one or more communication circuitry modules 68a, 68b adapted for transmitting and/or receiving (e.g., transceiving) electromagnetic radiation (e.g., microwave, infrared, radio-frequency (RF), optical, etc.) and/or for transmitting and/or receiving magnetic fields through the barrier 110 between the first surface 111 and the second surface 112 thereof. The one or more communication circuitry modules 68a, 68b can optionally have corresponding terminals 69a, 69b preferably exposed at one or more surfaces. The terminals 69a, 69b of the communication circuitry modules 68a, 68b can be adapted for electrical connection with another component such as a sensing element 50 (not shown), signal processing circuitry (not shown) and/or data retrieval circuitry (not shown). The terminals 69a, 69b can comprise, for example, contact pins or contact pads.

Referring again to FIG. 3A, and with further reference to FIGS. 3E through 3G, a ported sensor 1 or ported sensor subassembly 10, in either case comprising a sensing element as part of the ported unit, can be interfaced with a fluidic system 100 across a barrier 110 using a coupling 60. In this embodiment, the coupling 60 is preferably a mechanical coupling that allows access for a sensing element 50' (associated with the ported sensor 1) across the barrier 110 of the fluidic system 100. Since such access can preferably be effected during operation of the fluidic system, it is advantageously appreciated that the access should be effected without compromising the integrity of the fluidic system operations. In general, this can be accomplished, for example, with a coupling 60 comprising one or more bodies 62 having a first surface 63 on the internal fluid-side of the barrier 110, and an opposing second surface 64 on the external side of the barrier 110. The coupling 60 and/or the body 62 can be affixed to (e.g., fixedly mounted on, fixedly attached to) the barrier 110. Alternatively, the coupling 60 and/or the body 62 can be integrally formed with the barrier 110. The coupling 60 and/or the body 62 and/or a component of the coupling and/or the body can alternatively be removably engaged with the barrier 110. In any case, the coupling 60 and/or the body 62 can comprise one or more components (e.g. circuit modules) that are installed components of the fluidic system, and/or one or more components (e.g., circuit modules) that are components of the ported sensor 1 and which are functional as coupling components when the ported sensor is interfaced with the fluidic system.

With reference to FIG. 3E, the body 62 can further comprise one or more passages 65 generally extending between the first surface 63 and the second surface 64 of the body 62. The passage 65 can be a straight passage such as a through-bore, or can comprise one or more turns. In the embodiment shown, at least a portion of the passage 65 can be sized to accommodate through-transit of a sensing element (e.g., flexural resonator) of a ported sensor 1. The coupling 60 and/or the body 62 can further comprise one or more valves, such as a sliding gate valve 72 (shown in an "open" position), for selectively isolating the fluid in the fluidic system 100 from the passage by operation of the one or more valves. The depicted gate valve 72 can be received in seat 73 when in a "closed" position, such that the gate valve 72 would sealingly isolate the passage 65 from the fluid. The coupling 60 and/or the body 62 can further be adapted for receiving at least a portion of the ported sensor 1 (or ported sensor subassembly 10) in sealing engagement with the body. For example, as shown the passage 65 is configured to receive probe portion 3 of the ported sensor 1. One or more seals 74a, 74b (e.g., o-ring seals) can be used to fluidically seal the ported sensor 1 (or ported sensor subassembly 10) with the coupling 60 and/or body 62, upon engagement of the ported sensor 1 with the body. As shown, seal 74a can be situated in the passage 65 such that it sealingly engages with a periphery of probe portion 3 of ported sensor 1. Also, seal 74b can be situated for sealing engagement between the second surface 64 of the body 62 and an end surface 4 of the ported sensor 1. In operation, the ported sensor 1 (or ported sensor subassembly) can be interfaced with the fluidic system by inserting the probe portion 3 thereof into passage 65 of the body 62 while the gate valve 72 is in the closed position, engaged against seat 73, such that the ported sensor 1 (or ported sensor subassembly 10) is sealingly engaged with the body 62 by seals 74a, 74b. The gate valve 74 can then be opened, such that the sensing surface of sensing element 50 can contact the fluid for sensing. After the sensing period, the gate valve 74 can be reclosed, and the ported sensor 1 (or ported sensor subassembly) can be withdrawn. In this manner, the ported sensor or ported sensor subassembly is interfaced with the fluidic system across the barrier, even during operation of the fluidic system, without compromising the integrity of the fluidic system.

Referring now to FIGS. 3F and 3G, in alternative embodiments, the body 62 can further comprise a sensing chamber 75 (FIG. 3F, FIG. 3G)/sample chamber 75 (FIG. 3G) within the body 62. The sensing/sample chamber 75 can be open-ended (as shown) at least until a ported sensor or ported sensor subassembly is interfaced with the fluidic system. One or more passages 76a, 76b can provide fluid communication between the sensing/sample chamber 75 and the fluid of the fluidic system 100. Isolation valves 78a, 78b associated with the passages 76a, 76b can selectively isolate the sensing/sample chamber 75 from the fluid in the fluidic system 100. In FIG. 3F, a single passage 76a and associated valve 78a are shown. In FIG. 3G, two passages 76a,b, and associated valves 78a, 78b are depicted. The passages 76a, 76b can be straight such as a through-bore, or can comprise one or more turns. The coupling 60 and/or the body 62 can further be adapted for receiving at least a portion of the ported sensor 1 (or ported sensor subassembly 10) in sealing engagement with the body. For example, as shown the body 62 is configured to receive probe portion 3 of the ported sensor 1. One or more seals 74a (e.g., o-ring seal) can be used to fluidically seal the ported sensor 1 (or ported sensor subassembly 10) with the coupling body 62, upon engagement of the ported sensor 1 with the body, via sealing engagement between the second surface 64 of the body 62 and an end surface 4 of the ported sensor 1. The embodiment shown in FIG. 3G includes or more additional passages, such as a sampling passage 77 that provides fluid communication between the sensing/sample chamber 75 and an external sample port 79. An isolation valves 78c can be used to isolate the sensing/sample chamber 75 from the sample port 79. Significantly, the sampling passage 77 allows for withdrawing a sample from the fluidic system that corresponds to the fluid being sensed substantially concurrently therewith. In operation, the ported sensor 1 (or ported sensor subassembly) can be interfaced with the fluidic system by inserting the probe portion 3 thereof into sensing/sampling chamber 75 of the body 62 while the isolation valves 78a, 78b are in the shut position, such that the ported sensor 1 (or ported sensor subassembly 10) is sealingly engaged with the body 62 by seal 74a. The one or more fluid isolation valves 78a, 78b can then be opened, such that the sensing/sampling chamber fills, and the sensing surface of sensing element 50 can contact the fluid for sensing. Before, during or after sensing, a portion or all of the fluid within the sensing/sample chamber can be withdrawn through passage 77 (by opening isolation valve 78c) to obtain a concurrent sample. After sampling, the isolation valve 78c can be shut. The isolation valve(s) 78a, 78b can also be shut (after sensing), and the ported sensor 1 (or ported sensor subassembly) can be withdrawn. In this manner, the ported sensor or ported sensor subassembly is interfaced with the fluidic system across the barrier, even during operation of the fluidic system, without compromising the integrity of the fluidic system.

In any of the embodiments shown in FIGS. 3A through 3G, the ported sensor 1 or the ported sensor subassembly 10 can be positioned to form an interfaced sensor, and can be held in place as an interfaced sensor during one or more sensing periods by any appropriate manner. For example, the ported unit could be held in place only by hand (human applied force) during the sensing period. Alternatively, the ported unit can be held in the interfaced position using a mechanical locking device (e.g., bolts, clamps, etc.). As another alternative, the ported unit can be magnetically coupled to the fluidic system to form the interfaced sensor.

In one embodiment, with reference to FIG. 3F, for example, the initially-ported unit could comprise a ported sensor 1 having a sensing element 50 that is interfaced with the fluidic system 100 through a coupling 62. The coupling 62 and the sensing element 50 can be specially adapted such that after the initial interfacing, the sensing element is translated from the ported sensor 1 to become fixedly attached to the fluidic system. Upon disinterfacing, the ported-away unit would then be a ported sensor subassembly 10 having an absence of the sensing element. In this hybrid approach, a sensing element 50 could be periodically installed into the fluidic system using the ported-to sensor 1, with intermittent sensing periods using the ported-away sensor subassembly 10.

Sensing with Interfaced Sesnor

The interfaced sensor can be advantageously applied to sense the fluid by collecting data, and typically a data stream that is fluid dependent, and that can be processed to identify and evaluate particular fluid property characteristics.

In any of the aforementioned and/or following-mentioned approaches and embodiments, the signal processing circuitry can comprise one or more circuit modules for processing data originating from the sensing element (generally, directly or indirectly). The signal processing circuitry can comprise each such circuit module alone (i.e., individually) or in various combinations and permutations. The data being processed can be raw data (previously unprocessed data) typically coming either directly from the sensing element or from a data storage media (i.e., data memory circuitry) that captured the data directly from the sensing element. Alternatively, the data being processed by one or more circuit modules of the signal processing circuit can be previously processed data (e.g., from another module thereof).

Figure 4B:
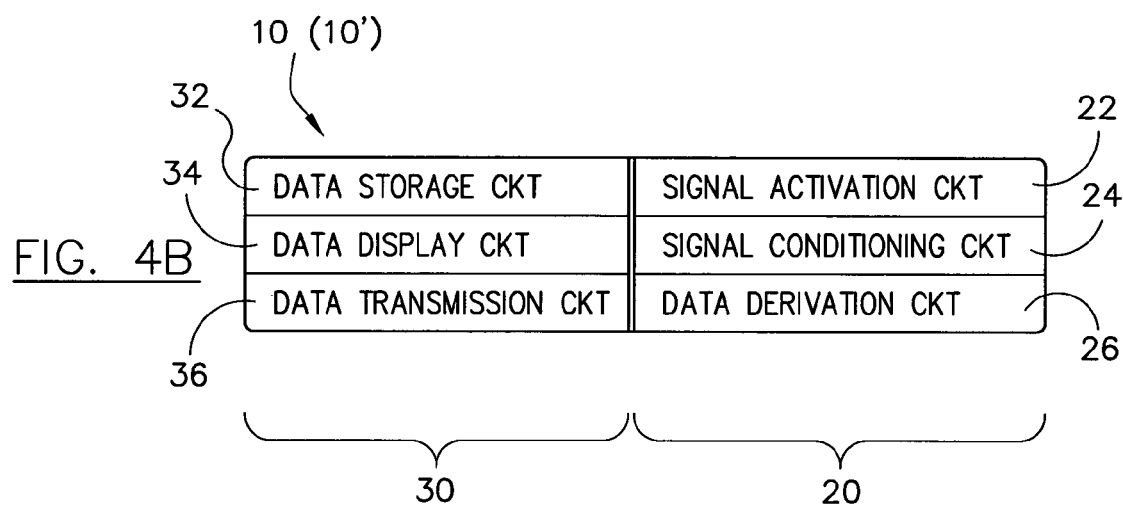

Generally, referring now to FIGS. 4A and 4B and to FIGS. 5A and 5B, the signal processing circuit 20 can comprise one or more circuits (or circuit modules) for activating a sensing element and/or for processing data originating with a sensing element, including generally for example: a signal activation circuit 22 (generally optional, e.g., for providing an electronic stimulus to the sensing element during active sensing, as discussed in more detail below); a signal conditioning circuit 24 for processing data originating from the sensing element (generally preferred, e.g, for altering an electronic characteristic of a data signal, typically resulting in a conditioned data or data stream); and/or a data derivation circuit 26 for processing data originating from the sensing element (generally preferred, e.g., for identifying, selecting or interpreting a particular electronic characteristic of a data signal, typically resulting in derived data or data stream that is more closely related to the property (or properties) of interest (e.g., has higher information content and/or greater information value) than a raw data stream and/or a conditioned data or data stream).

Figure 4C:
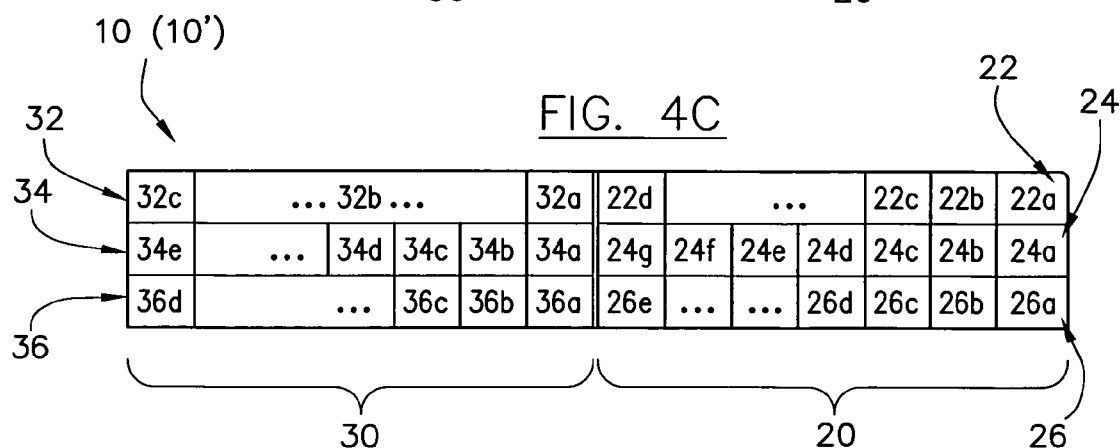

In particular, with further reference to FIGS. 4C and 5C, the signal processing circuit 20 can comprise one or more circuits (or circuit modules) as signal conditioning circuits 24, such as for example: signal input circuitry 24a (e.g., for receiving a response signal from the sensing element); amplifying circuitry 24b (e.g. including pre-amplifiers and amplifiers, for amplifying a signal); biasing circuitry 24c (e.g., for offsetting or otherwise changing a reference frame relating to the signal, including such as for reducing analog signal offsets in the response signal); converting circuitry 24d (e.g., analog-to-digital (A/D) converting circuitry for digitizing data or a data stream); microprocessor circuitry 24e (e.g., for microprocessing operations involving data originating from the sensing element and/or user-defined data); signal-processing memory 24f (e.g., typically being accessible to one or more signal processing circuits or circuit modules for providing data thereto, such as for example system-specific and/or sensing-element-specific identifying indicia, user-defined data for signal conditioning, etc.); and/or signal output circuitry 24g (e.g., for outputting a conditioned signal to another circuit module (e.g., to a data derivation circuit and/or to a data retrieval circuit).

Referring again to FIGS. 4C and 5C, the signal processing circuit 20 can comprise one or more circuits (or circuit modules) as data derivation circuits 26, such as for example: signal input circuitry 26a (e.g., for receiving a response signal from the sensing element or from one or more data conditioning circuits 24); signal detection circuitry 26b (e.g, for identifying and/or detecting one or both of phase data and/or amplitude data and/or frequency data of the response signal); microprocessor circuitry 26c (e.g., for microprocessing operations involving data originating from the sensing element, typically involving a microprocessor configured for processing one or more software operations such as software algorithms or firmware algorithms (e.g., a data-fitting algorithm) for determining a parameter of the fluid that is associated with a property thereof, and/or typically for processing user-defined data (e.g., predefined data and/or substantially concurrently-defined data) in conjunction with the data originating from the sensing element, and/or typically involving user-initiated, user-controllable, and/or user-interactable processing protocols, typically for determining a parameter using a calibration with a fitting algorithm, for determining a parameter using a correlation algorithm, for determining a change in a detected signal characteristic (e.g., frequency, amplitude) or for determining a a determined parameter); signal-processing memory 26d (e.g., typically including electronic data storage media, such as non-volatile memory (e.g., ROM, PROM, EE-PROM, FLASH memory, etc.), typically being pre-loaded with and/or being accessible for loading user-defined data (e.g., calibration data, correlation data, data defining approximated fluid properties, system-specific information, sensing-element specific information such as an identifying indicia, and/or typically being accessible to one or more signal processing circuits (or circuit modules) for use thereof; and/or signal output circuitry 26e (e.g., for outputting a conditioned signal to another circuit module (e.g., to a data derivation circuit and/or to a data retrieval circuit).

Likewise, in any of the aforementioned and/or following mentioned approaches and embodiments, referring again to FIGS. 4A and 4B and to FIGS. 5A and 5B, the data retrieval circuitry 30 can comprise one or more modules for retrieving data—whether raw data or processed data. Generally, the data retrieval circuit 30 can comprise one or more circuits (or circuit modules), including a data storage circuit 32, a data display circuitry 34 and/or a data transmission circuitry 36. The data retrieval circuit 30 can be in electrical communication with the sensing element directly, or alternatively, via a signal processing circuit 20 that processes (e.g., amplifies, biases, converts, etc.) raw data coming from the sensing element.

With further reference to FIGS. 4C and 5C, the data storage circuit 32 can typically comprise: signal input circuitry 32a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26); a data storage media 32b (e.g., such as non-volatile memory (e.g., ROM, PROM, EE-PROM, FLASH memory etc.); and, signal output circuitry 32c (e.g., for outputting a stored data or stored data stream to another circuit module (e.g., to a data derivation circuit and/or to a data transmission circuit and/or to a data display circuit).

Data display circuit 34 as shown in FIGS. 4C and 5C can configured to be effective for displaying data associated with one or more properties of a fluid, or for displaying a status of the fluid, where such status is based on data associated with a property of the fluid. Hence, data display circuit 34 can include a display device, and can typically comprise: signal input circuitry 34a (e.g., for receiving raw data or a raw data stream from the sensing element, and/or for receiving conditioned data or a conditioned data stream from one or more signal conditioning circuits 24, and/or for receiving derived data or a derived data stream from one or more data derivation circuits 26, and/or for receiving stored data or stored data stream from one or more data storage circuits 32); a data-display memory 34b (e.g., such as non-volatile memory (e.g., ROM, PROM, EE-PROM, FLASH memory, etc., or random access memory (RAM), in either case typically for temporarily storing a data or data stream to-be-displayed); a microprocessor circuit 34c (e.g., for processing/modifying data, such as stored, to-be-displayed data); a visual display circuit 34d (e.g., digital computer monitor or screen; e.g., a status light such as a LED status light, e.g., a printer, e.g., an analog meter, e.g., a digital meter, e.g., a printer, e.g., a data-logging display device, e.g., preferably in some embodiments a graphical user interface, etc.); and, signal output circuitry 34e (e.g., for outputting a stored data or stored data stream—such as to another circuit module (e.g., to a data derivation circuit and/or to a data transmission circuit and/or to a data display circuit).

Data transmission circuit 36 as shown in FIGS. 4C and 5C can be configured to be effective for transmitting data originating from the sensing element. Specifically, for example, the data transmission circuit 36 can include: signal input circuitry 36a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26, and/or for receiving stored data or stored data stream from one or more data storage circuits 32); an optional microprocessor circuit 36b (e.g., for processing/modifying data, such as stored, to-be-transmitted data, and/or for controlling data transmission protocols); transmission protocol circuitry 36c (e.g., for effecting and coordinating communication protocols, such as for example a hard-wired interface circuit (e.g., TCP/IP, 4-20 mA, 0-5V, digital output, etc.), or a wireless communication circuit involving an electromagnetic radiation (e.g., such as radio frequency (RF) short range communication protocols (e.g., Bluetooth™, WiFi—IEEE Standard 80211 et seq., radio modem), land-based packet relay protocols, satellite-based packet relay protocols, cellular telephone, fiber optic, microwave, ultra-violet and/or infrared protocols), or a wireless communication circuit involving magnetic fields (e.g., magnetic induction circuits); and signal output circuitry 36d (e.g., for outputting a transmission of stored data or stored data stream—such as to another circuit module (e.g., to a data derivation circuit and/or to a data storage circuit and/or to a data display circuit).

Data transmission is particularly preferred using a data transmission circuit 36 in connection with a ported sensor subassembly that comprises a signal-processing memory and the data transmission circuit. Where the signal-processing memory comprises user-defined data, such data can be configured to be accessible to the data transmission circuit for communicating the user-defined data from the ported sensor subassembly to the fluidic system or to a remote data repository. In another preferred approach, the ported sensor subassembly can comprise a data transmission circuit for communicating data associated with one or more properties of the fluid from ported sensor subassembly to the fluidic system or to a remote data repository. In another method, the ported sensor subassembly can comprise a data storage media accessible for storing data associated with one or more properties of the fluid, and in combination therewith, a data transmission circuit for communicating stored data from the data storage media to the fluidic system or to a remote data repository, in either case preferably using a wireless communication protocol.

In any event, preferably, generated data is stored (e.g., in memory), displayed (e.g., in a graphical user interface or other display device) or (meaning additionally or alternatively) transmitted (e.g., using hard-wired or wireless communications protocols) using the data retrieval circuit of the interfaced sensor.

Although listed and represented in the figures in a particular (e.g., linear) order, there invention is not limited to use of such circuit modules in any particular order or configuration, and a person of ordinary skill in the art can determine a suitable circuit design for a particular fluidic system and a particular sensor, in view of the general and specific teaching provided herein.

Regardless of the particular configuration for the interfaced sensor, the fluid is sensed, actively or passively, using the interfaced sensor during a first sensing period to generate data associated with one or more properties of the fluid. In passive sensing mode of operation, the flexural resonator sensing element is displaced by the fluid to generate a signal (e.g., such signal being generated by piezoelectric material of sensing element, with appropriate electrodes), without application of an electronic input stimulus to the flexural resonator. In an active sensing mode of operation, an electronic stimulus (e.g., input signal having a voltage and/or frequency) is provided to the flexural resonator sensing element to initiate (via piezoelectric properties) a mechanical response in the sensing element such that at least a portion of the sensing surface of resonator displaces at least a portion of the fluid. The mechanical response is fluid dependent, and the extent of that dependence can be measured electronically, as is known in the art. With further reference to FIGS. 4B and 4C and to FIGS. 5B and 5C, a signal activation circuit 22 can comprise, for an active sensing mode of operation, a signal input circuitry 22a (e.g., for receiving a data or a data stream or instructions on active sensing signals) one or more user-defined or user-selectable signal generators, such as a frequency generator circuitry 22b, and/or such as a voltage spike generator circuitry 22c, and in each case, e.g., for providing an electronic stimulus to the sensing element, in an active sensing configuration; and signal output circuitry 22d.

In a preferred operation involving an active sensing mode, a stimulus signal (e.g., such as a variable frequency signal or a spike signal) can be intermittently or continuously generated and provided to the sensing element. A property-influenced signal, such as a frequency response, is returned from the sensing element. The return signal (e.g., frequency response) can be conditioned and components of the signal (e.g., frequency response) can be detected. The method can further includes converting the frequency response to digital form, such that the digital form is representative of the frequency response received from the sensing element. Then, first calibration variables can be fetched from a memory. As used herein, the term "fetch" should be understood to include any method or technique used for obtaining data from a memory device. Depending on the particular type of memory, the addressing will be tailored to allow access of the particular stored data of interest. The first calibration variables can define physical characteristics of the sensor or sensing element. Second calibration variables can also be fetched from memory. The second calibration variables define characteristics of the sensor or sensing element in a known fluid. The digital form is then processed when the sensing element is in the fluid under-test, and the processing uses the fetched first and second calibration variables to implement a fitting algorithm to produce data that relates to the fluid properties or fluid characteristics of the fluid under-test.

In some embodiments involving an active sensing mode and using a mechanical resonator sensing element (such as a flexural resonator sensing element), it may be preferably to employ an active sensing mode of operation involving an input stimulus signal having a frequency of not more than about 1 MHz, and preferably not more than about 500 kHz, and preferably not more than about 200 kHz, and most preferably not more than about 100 kHz. In some embodiments, even lower frequencies can be employed in the operation of the mechanical resonator sensing element, including for example frequencies of not more than about 75 kHz. Specific operational ranges include frequencies ranging from about 1 kHz to about 1 MHz, preferably from about 1 kHz to about 500 kHz, preferably from about 1 kHz to about 200 kHz, preferably from about 1 kHz to about 100 kHz, preferably from about 1 kHz to about 75 kHz, more preferably from about 1 kHz to about 50 kHz, more preferably still from about 5 kHz to about 40 kHz, even more preferably from about 10 kHz to about 30 kHz and most preferably from about 20 kHz to about 35 kHz. In such embodiments, it may be preferably to provide an input stimulus signal that has a frequency that varies over time. In such embodiments, it may be preferably to provide two or more cycles of varying a frequency over time over a predetermined range of frequencies, and preferably over a frequency range that includes the resonant frequency for the flexural resonator sensing element. Such frequency sweeping offers operational advantages that are known in the art.

In a preferred operation involving a passive sensing mode, the sensing element, preferably a mechanical resonator such as a flexural resonator, interacts with the fluid to generate a property-influenced signal. The signal from the sensing element is intermittently or continuously observed and/or retrieved by the signal processing circuit. The signal can be conditioned and components of the signal (e.g., frequency response, voltage, etc.) can be detected. The method can further include converting the response to digital form, such that the digital form is representative of the signal received from the sensor. Then, as above in the active mode, first and/or second calibration variables can be fetched from a memory. The first calibration variables can define physical characteristics of the sensor or sensing element. Second calibration variables can also be fetched from memory. The second calibration variables can define characteristics of the sensor or sensing element in a known fluid. The digital form can then processed when the sensing element is in the fluid under-test, and the processing uses the fetched first and second calibration variables to implement a fitting algorithm to produce data that relates to the fluid properties or fluid characteristics of the fluid under-test.

In preferred embodiments, one or more circuit modules of the signal processing circuit and/or the data retrieval circuit can be implemented and realized as an application specific integrated circuit (ASIC). See, for example, above-referenced U.S. Ser. No. 10/394,543 entitled "Application Specific Integrated Circuitry For Controlling Analysis For a Fluid" filed on Mar. 21, 2003 by Kolosov et al., and PCT Application. No. PCT/US04/008555 entitled "Application Specific Integrated Circuitry For Controlling Analysis For a Fluid" filed on Mar. 19, 2004 by Kolosov et al. Particularly preferred circuit configurations are described below, but should be considered generally applicable to each approach and embodiment of the inventions described herein.

User-Defined Data (e.g., Calibration, Identifying Indicia)

Generally relevant to each of the methods, systems and apparatus of the inventions, user-defined data such as calibration data, correlation data, signal-conditioning data can be employed as part of a signal processing circuit (e.g., signal conditioning and/or data derivation circuitry). Likewise, additionally or alternatively, identifying indicia such as bar-codes, electronic signatures (e.g., 64-bit serial numbers) can be used to identify one or more of: particular fluidic systems, particular locations within a fluidic system; particular fluid types; particular sensors; and/or particular sensing elements (including sensing element types (e.g., tuning fork flexural resonator), sensing element lot numbers for a set of co-manufactured sensing elements, and specific particular individual sensing elements). Such user-defined identifying indicia can be particularly useful in combination with user-defined calibration, correlation and/or signal conditioning data since such data can be specific to the fluidic system, the location, the fluid type; the sensor (type or individual sensor) and/or the particular sensing elements (including sensing element types (e.g., tuning fork flexural resonator), sensing element lot numbers for a set of co-manufactured sensing elements, and specific particular individual sensing elements). The user-defined data can be fluid-property (e.g., temperature dependent), and therefore, there can be interaction between one or more sensing elements (e.g., temperature sensing element) and a user-defined data (e.g., calibration data) for a particular fluid in a particular system using a particular resonator. The user-defined data can generally be pre-defined data or can be concurrently-defined data, and the defining can be done by a person and/or by a computer.

The level of specificity of any particular user-defined data to any particular fluidic system, fluid, sensor or sensor element will depend on the particular user-application, the property of interest, the sensor type, the required degree of accuracy, etc.

In a preferred methods, apparatus and systems, in which a flexural resonator sensing element is employed alone or in conjunction with one or more other systems, it is preferable to have accessible user-defined calibration data that includes at least (i) flexural resonator sensing element-specific (e.g., calibration) data, as well as (ii) application-specific (e.g., fluid type) data (e.g, calibration data). It is also preferable to have specific user-defined identifying indicia.

In general, there are several approaches for managing a network of interfaced sensors across multiple fluidic systems, where each sensor/system may require its own specific signal conditioning data (e.g., offset information) and/or its own specific user-defined input to a data derivation circuitry (e.g. calibration data or correlation data or approximate fluid property values, etc.).

In one approach, discussed for example in connection with FIG. 2C, each installed sensing element can have a locally installed signal-processing memory module for storing the required user-defined data. A person porting a ported sensor subassembly can then initiate a sensing operation (or retrieve an accumulated or stored data stream) using signal processing circuitry of the ported sensor subassembly. The ported signal processing circuitry can communicate with the locally-installed signal-processing memory module to get the user-defined data (e.g. calibration data) specific for sensing the fluid at that location of that fluidic system using that particular sensing element.

In an additional or alternative approach, a signal-processing memory module for storing user-defined data for data derivation can be included within the ported sensor subassembly. In some embodiments, the data can be a standard data set with a set of varying corrections for particular sensors or fluids or fluid conditions. Some sort of identifying indicia is preferably available at the site of the interfaced sensor for identifying it with particularity. In this instance, a person porting a ported sensor subassembly can then initiate a sensing operation (or retrieve an accumulated or stored data stream) by first interrogating (querying) the identifying indicia, and then using the read identifying indicia within the ported sensor subassembly to obtain the relevant user-defined data set for the fluid at that location of that fluidic system using that particular sensing element.

Other variations on this approach can likewise be beneficially applied.

Sensors Having Flexural Resonator Sensing Elements and Operation Thereof

Figure 7A:
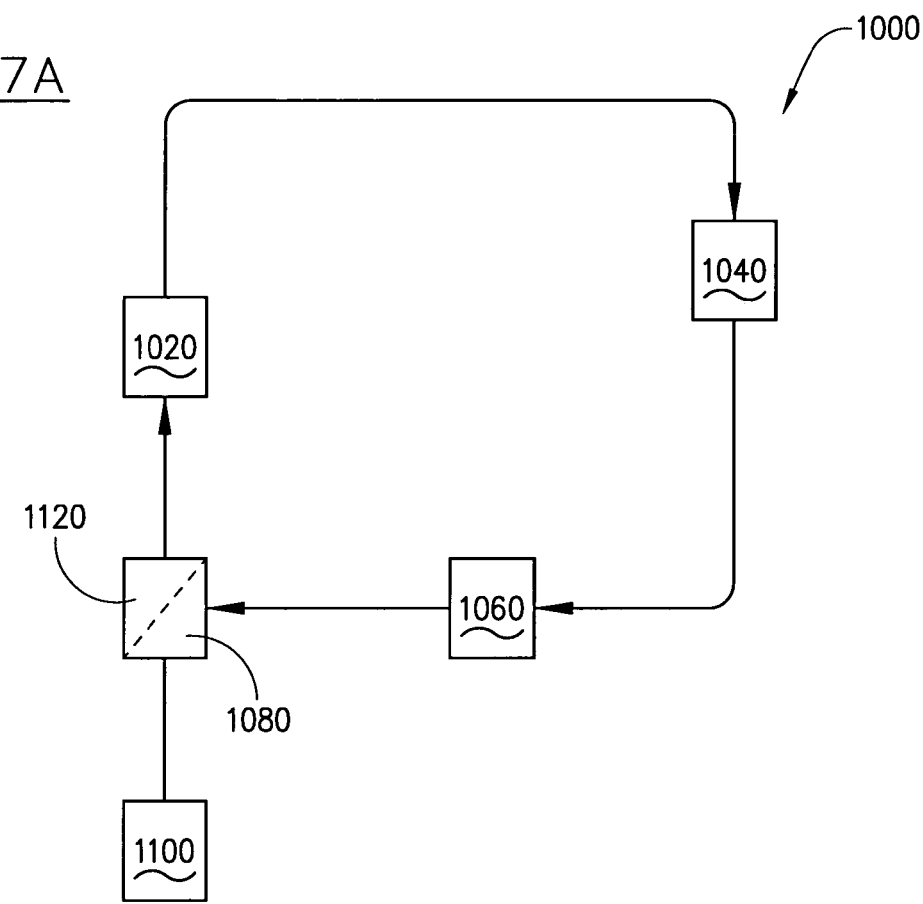

As seen in FIG. 7A, one embodiment involves the incorporation of a sensor according to the present invention into a fluidic system 1000, such as an environmental control system, that includes one or more unit operation devices 1020, 1040, 1060 such as a compressor, an expansion valve, a condenser and an evaporator through which a thermal change fluid can be cycled via one or more passages, such as in a conduit. Other components may also be employed as desired, such as one or more suitable pumps, a filter, a dryer, a suitable flow cell, or a combination of two or more thereof. Likewise, any of the above components may be omitted from a system of the present invention. Suitable valving and process monitoring instrumentation may also be employed in the fluidic system 1000.

One or more of the interfaced sensors 1080 according to the present invention is adapted for permanent or temporary placement within in one of the system components or between one of the system components. For example one or more sensors 1080 may be situated between various unit operation devices 1020, 1040, 1060. Likewise, one or more interfaced sensors may additionally or alternatively be incorporated in another component, such as a conduit, coil, filter, nozzle, dryer, pump, valve or other component, or positioned upstream or downstream therefrom. The sensor may be located in the flow path of the fluid (e.g., in a conduit), a headspace or both. In a particular embodiment, the sensor is included along with (and optionally integrated therewith) a condition monitoring device such as a temperature measurement device, a pressure measurement device, a mass flow meter, or combinations of two or more of such devices. Without limitation, an example of a combined pressure and temperature sensor is discussed in U.S. Pat. No. 5,586,445 (incorporated by reference).

Sensing in accordance with the present invention is particularly attractive for evaluating one or more of properties of the fluid, such as the level of a fluid (e.g., indicative of a system leak, a blockage in the system, or the like), the superheat condition of a fluid (e.g., the level of superheat), subcooling of a fluid, concentration of a desired component (e.g., refrigerant) in the fluid, or the presence or absence or concentration of an undesired component (e.g., contaminants) in the fluid. In particular, the sensor is effectively employed to monitor (continuously or periodically) small changes in conditions of the fluid, such as viscosity, density, viscosity/density product, dielectric constant, conductivity or combinations of two or more thereof, which are indicative of a change of one or more of the above-noted properties, or of a change in state of the fluid or the presence of contaminants, and to output the results thereof.

Optionally, the interfaced sensor, the ported sensor subassembly, or the ported sensor can be in signaling communication with a processing unit 1100 (which may include a user interface) for controlling operation of the fluidic system. The processing unit 1110 may be microprocessor integrated into the ported sensor, the ported sensor subassembly or the interfaced sensor, for example, as part of the signal processing circuitry as described above. The processing unit 1100 optionally can optionally also be in signaling communication with a condition monitoring device 1120 (shown as part of an integrated assembly with the interfaced sensor 1080. Thus, data obtained from the interfaced sensor 1080 may be processed along with other data to assist in monitoring and establishing operating conditions of the fludic system.

Thus, for example, in one aspect of the present embodiment, an interfaced sensor 1080 according to the present invention is employed to monitor at least one property of a fluid (e.g., the simultaneous monitoring of viscosity and density). Data generated from the sensor, along with other data (e.g., temperature, pressure, flow rate, or combinations thereof), for example, from the condition monitoring device 1120, can be sent to the processing unit 1100. From the data provided, the processing unit 1110, which typically will be programmed with a suitable algorithm, will process the data. In a process control embodiment, the processing unit can effect least one operation of the fluidic system selected from switching a subsystem of the fluidic system (e.g., a unit operation device 1020, 1040, 1060) or one or more components thereof between an "on" or "off" state, shutting or opening a valve in the fluidic system, changing a flow rate of the fluid, changing a pressure of the fluid, changing the operating speed or condition of one or more components of the fluidic system, or otherwise controlling operation of the fluidic system or a component thereof, providing a visual output signal, providing an audible output signal, or a combination thereof.

It will be appreciated that the above configuration of FIG. 7A permits the use of one or more modes of active sensing operations, such as excitation at one or more frequencies around resonance frequency of the resonator, or the time decay of oscillation after an electrical or mechanical impulse (e.g., a voltage spike). Passive operations can include, for example, observing passive oscillations due to ambient noise, vibrations, electromagnetic interference, etc.

The monitoring of fluid properties according to the invention may be performed under normal operating conditions of the machine into which the present sensor is placed. The present invention is particularly advantageous in that it operable over a broad range of temperatures. Thus, in one specific aspect, it is contemplated that the monitoring step occurs at a temperature below −40° C. or possibly the monitoring step occurs at a temperature above 400° C. Generally the monitoring will occur between these extremes. It is also possible that during or following monitoring, the response of the sensor is compared against another value, such as a prior response of the resonator, a response of another resonator located elsewhere in the system, a known reference value for the fluid, or a combination of two or more such comparisons. The observed response may be stored in memory or otherwise recorded. It may also be possible to have data about a particular fluid stored in memory of a suitable processor, which can be retrieved in response to a triggering event, such as inputting by a technician or reading of a fluid type by an optical detector, such as a bar code scanner.

As the fluid property changes over time, analysis can be made and the response compared with those of the fresh fluid. The identification of a difference between responses could then be used as a trigger or other output signal for communicating with diagnostics hardware, which would provide an audible or visual signal to the operator. It is also possible that a signal is outputted to a remote telemetry device, such as one located external of the system. Thus, as with any of the embodiments herein a "wireless" communications system might be employed, pursuant to which a signal that is outputted may be a radiofrequency signal or another electromagnetic signal. Comparison against reference values from the original fluid is not the only approach for generating a communication to a user about the fluid condition. It may be possible, for example, to pre-program certain expected values into a device, which then compares the real-time values obtained. Moreover, it is possible that no comparisons are made, but rather upon obtaining a certain threshold response, an output signal is generated for triggering a user notification, for triggering a system control unit to alter one or more functions of the system or a combination thereof. It is also contemplated that a sensor in a controlled fluid sample may be employed as an internal reference.

It is also possible that the response obtained from the monitoring is stored in a memory, with or without communicating the response to the user. In this manner, a service technician can later retrieve the data for analysis.

Figure 7B:
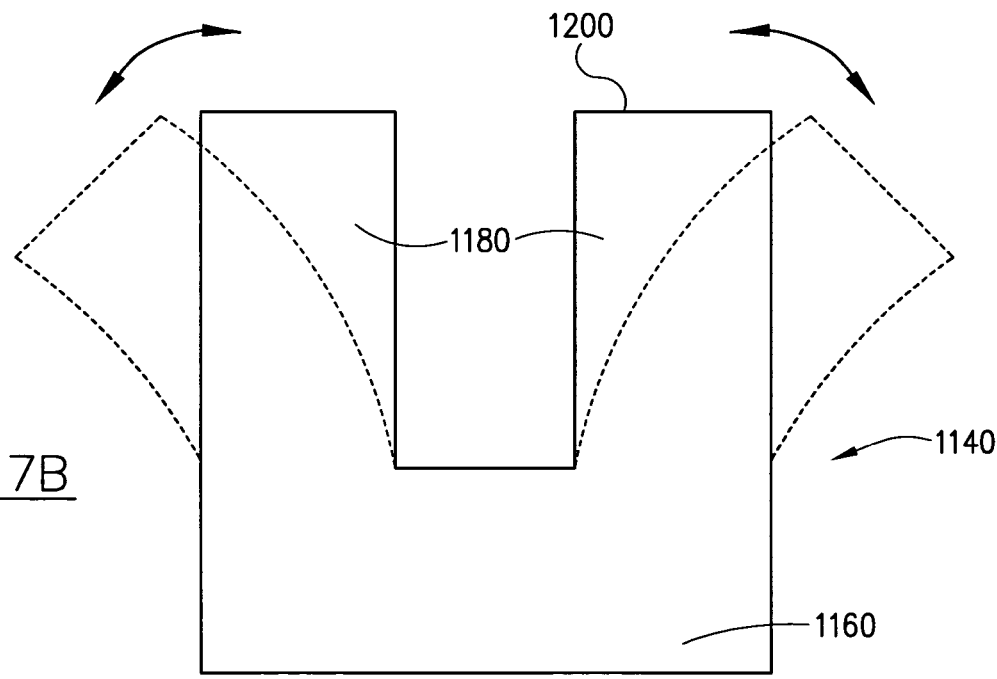

Turning now to FIG. 7B there is shown an illustration of one preferred resonator element 1140 in accordance with the present invention. The resonator element 1140 preferably includes a base 1160 that has at least two tines 1180 having tips 1200 that project from the base. The shape of the tines and their orientation relative to each other on the base may vary depending upon the particular needs of an application. For example, in one embodiment, the tines 1180 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator sensing element(s) are suitably positioned in an element holder. Alternatively, the elements (with or without a holder) may be securely attached to a wall or barrier or other surface defining one of the fluidic systems or passages into which it is placed. In yet another embodiment, the element is suitably suspended within a passage such as by a wire, screen, or other suitable structure.

Element holders may partially or fully surround the sensing elements as desired. Suitable protective shields, baffles, sheath or the like may also be employed, as desired, for protection of the elements from sudden changes in fluid flow rate, pressure or velocity, electrical or mechanical bombardment or the like to help locate an element relative to a fluid or combinations thereof. It should be appreciated that resonator elements may be fabricated from suitable materials or in a suitable manner such that may be employed to be re-useable or disposable.

Examples of approaches to materials combinations, or the packaging of sensing elements that may be employed in accordance with the present invention are disclosed, without limitation in commonly-owned U.S. Provisional Application Ser. Nos. 60/456,767 and 60/456,517 (both filed Mar. 21, 2003) (and incorporated by reference). Thus, one particular approach contemplates affixing a sensing element having a exposed sensing surface to a platform, wherein a spaced relationship is created between the exposed sensing surface and the platform. A suitable protective layer may be applied to cover the platform and/or the sensing element while maintaining an exposed sensing surface. The latter exposed sensing surface may be prepared by the use of a consumable protective layer (e.g., a polymer, starch, wax, salt or other dissolvable crystal, low melting point metal, a photoresist, or another sacrificial material) that is used to block the exposed sensing surface prior to applying the protective layer.

A plurality of the same type or different types of resonators of resonators can be used in combination. For example, a low frequency resonator may be employed with a high frequency resonator. In this manner, it may be possible to obtain a wider range of responses for a given sample.

The size of the sensing elements, especially mechanical resonator sensing elements such as flexural resonator sensing elements is not critical to the invention. In some applications, however, it should be appreciated that one advantage of the present invention is the ability to fabricate a very small sensor using the present resonators. For example, one preferred resonator has its largest dimension smaller than about 2 cm, and more preferably smaller than about 1 cm. One resonator has length and width dimensions of about 3 mm by 8 mm, and possibly as small as about 1 mm by 2.5 mm. Geometry of the resonator may be varied as desired also. For example, the aspect ratio of tines of the tuning forks, or geometrical factors of other resonators can be optimized in order to achieve better sensitivity to the properties of the gas phase, liquid phase or its particular components (e.g., a lubricant). For example, the aspect ratio of a tuning fork tine may range from about 30:1 to about 1:1. More specifically, it may range from about 15:1 to about 2:1.

It is thus seen that a preferred resonator is configured for movement of a body through a fluid. Thus, for example, as seen in FIG. 7B, the resonator may have a base and one or a plurality of tines projecting from the base. It is preferred in one aspect that any tine has at least one free tip that is capable of displacement in a fluid relative to the base. FIG. 7C illustrates a cantilever 1220 having a base 1240 and a free tip 1260. Other possible structures, seen in FIGS. 7D and 7E contemplate having a disk 1280, a plate 1300 or the like that is adapted so that one portion of it is displaceable relative to one or more variable or fixed locations 1320 (1320'). As seen in FIG. 7F, in yet another embodiment a resonator 1340 is contemplated in which a shear surface 1360 of the resonator has one or more projections 1380 of a suitable configuration, in order that the resonator may be operated in shear while still functioning consistent with the flexural or torsional resonators of the present invention, by passing the projections through a fluid.

In still other embodiments, and referring to FIGS. 7G, 7H and 7I, it is contemplated that a resonator 2000 may include an elongated member 2020 supported on its sides 2040 by a pair of arms 2060. As shown respectively in FIGS. 7G through 7I, the elongated member may be configured to oscillate side-to-side, back and forth, in twisting motions or combinations thereof.

The flexural resonator, such as the embodiment of FIG. 7B, may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, one of the materials will respond different than the other and the differences in responses will, in turn, result in the flexure of the resonator. In yet another embodiment, it is contemplated that plural resonators can be assembled together with an electrode at least partially sandwiched therebetween. In this manner, it may be possible to further protect electrodes from harsh conditions, while still achieving the desired flexure. One specific example might include a two or more lithium niobate or quartz tuning forks joined together with a gold electrode therebetween. Other configurations (e.g., an H-shaped resonator) and material combinations may be employed as well, as disclosed in U.S. Provisional Application Ser. Nos. 60/456,767 and 60/456,517 (both filed Mar. 21, 2003), incorporated by reference.

As can be seen, the selection of the specific resonator material, structure, or other characteristic will likely vary depending upon the specific intended application. Nonetheless, it is preferred that for each application, the resonator is such that one or a combination of the following features (and in one highly preferred embodiment, a combination of all features) is present: a coating, if placed upon the resonator in a thickness greater than about 0.1 micron, will not substantially detract from resonance performance; the resonator is operable and is operated at a frequency of less than about 1 MHz, and more preferably less than about 100 kHz; the resonator is substantially resistant to contaminants proximate to the sensor surface; the resonator operates to displace at least a portion of its body through a fluid; or the resonator responses are capable of de-convolution for measuring one or more individual properties of density, viscosity, viscosity/density product, conductivity or dielectric constant.

The resonator may be uncoated or coated or otherwise surface treated over some or all of its exterior surface. A preferred coating is a metal (e.g., a conductive metal similar to what may be employed for electrodes for the sensor, such as silver, gold, copper, aluminum or the like), plastic, ceramic or composite thereof, in which the coating material is substantially resistant to degradation from the fluid to which it is to be exposed or to surface build-up, over a broad temperature range. For example, one preferred embodiment, contemplates the employment of a base resonator material and a performance-tuning material. Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. In another aspect, the dielectric constant of the performance-tuning material preferably is greater than that of quartz alone, such as by a factor of 5 or more, more preferably by a factor of 10 or more and still more preferably by a factor of 20 or more.

Figure 8A:
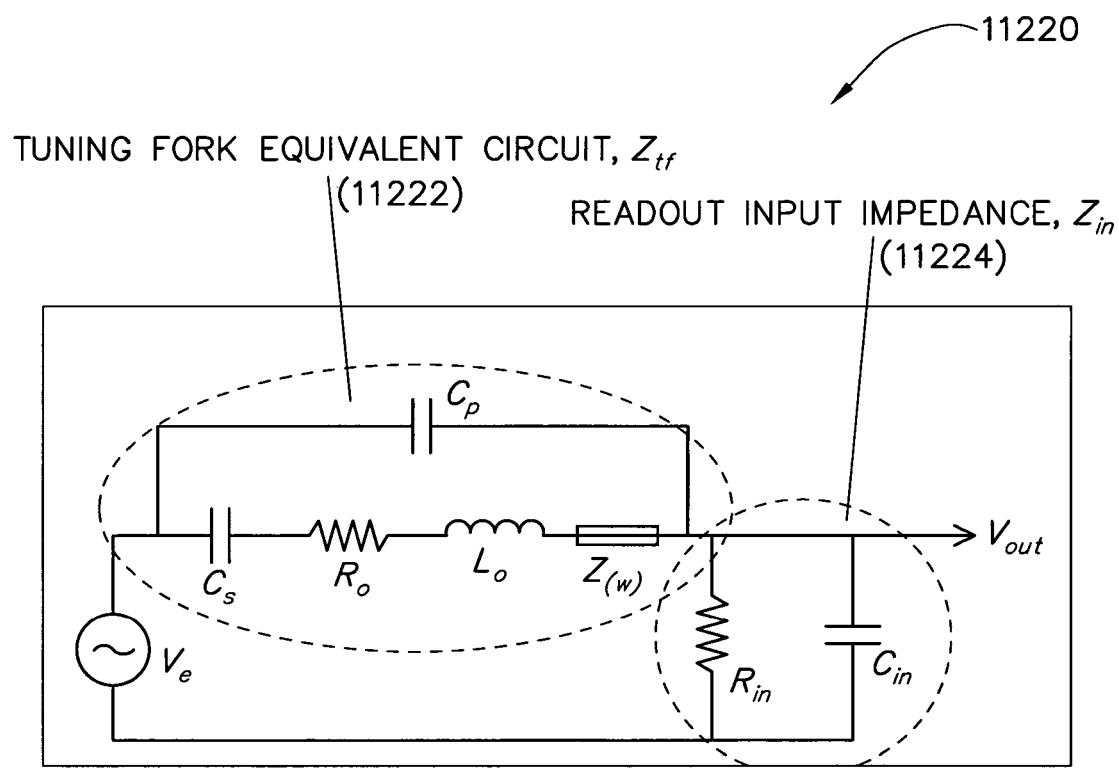

FIG. 8A illustrates a circuit diagram 11220 for a tuning fork equivalent circuit 11222 and a read-out input impedance circuit 11224. The frequency generator is coupled to the tuning fork equivalent circuit 11222 to a parallel connection of a capacitance Cp as well as a series connection of a capacitor Cs, a resistor Ro, an inductor Lo, and an equivalent impedance $Z(\omega)$. The read-out impedance circuit includes a parallel resistor Rin and a capacitor Cin. The output voltage is thus represented as Vout.

The equations shown in FIG. 8B can define the equivalent circuit. In equation (2), the Vout of the equivalent circuit is defined. In equations (3) and (4), the impedance Zin and Ztf are derived. Equation (5) illustrates the resulting impedance over frequency $Z(\omega)$. As can be appreciated, the voltage Vout, graphed verses the frequency $Z(\omega)$, necessitates the determination of several variables.

The variables are defined in equation (1) of FIG. 8B. In operation, the tuning fork's frequency response near the resonance is used to determine the variables that will define the characteristics of the fluid-under-test. The algorithm that will be used to determine the target fluid under-test characteristic parameters will require knowledge of data obtained during calibration of a tuning fork. In addition to access to calibration data, the algorithm will also utilize a data fitting process to merge approximated variables of the target fluid under-test, to the actual variable characteristics (i.e., density, viscosity, dielectric constant) for the fluid under-test.

In the circuit, it is assumed that $C_s$, $R_o$, $L_o$ are equivalent characteristics of a preferred resonator in a vacuum, $C_p$ is the equivalent parallel capacitance in a particular fluid under-test, ρ is the fluid density, η is fluid viscosity, ω is oscillation frequency. Cp is a function of k, as shown in equations (6) through (10). The constant "k" is, in one embodiment, a function of the tuning fork's geometry, and in one embodiment, defines the slope of a curve plotting (Cpmeasured, Cpcal, and Cpvaccum) verses (∈measured, ∈cal, and ∈vacuum), respectively. In a physical sense, the constant "k" is a function of the tuning fork's geometry, the geometry of the tuning fork's electrode geometry, the tuning fork's packaging (e.g., holder) geometry, the material properties of the tuning fork, or a combination of any of the above factors. The resulting value of Cp will be used to determine the dielectric constant ∈ as shown by the equations.

Further, it can be appreciated that that viscosity and density can be de-convoluted based on the equations defined in FIG. 8C. For some sensors, the value of $C_{p\ measured}$ is typically on the order of about 1 to 3 orders of magnitude greater than the value of $C_s$. Accordingly, in order to improve the ability to measure $Z(\omega)$, desirably trimming circuitry is employed as part of or in association with the signal conditioner, such as a trimming circuits. In order to more efficiently process the signal being received from the tuning fork, the signal 232 is signal conditioned to eliminate or reduce the signal offset and thus, increase the dynamic range of the signal produced by the tuning fork. Thus, the data being analyzed can be more accurately processed.

FIGS. 9A through 9C and 10A through 10C represent one set of preferred approaches and embodiments for realizing a signal processing circuitry for a flexural resonator sensor. In particular, the described approaches and embodiments are considered in the context of an interfaced sensor applied with a fluidic system within an engine, and in particular, in combination with an engine control unit (ECU), which directs overall control of multiple aspects of engine operation. This should be understood as being an example demonstrating an application and manner of realizing the present inventions, and should not be limiting on the inventions described herein.

Figure 9A:
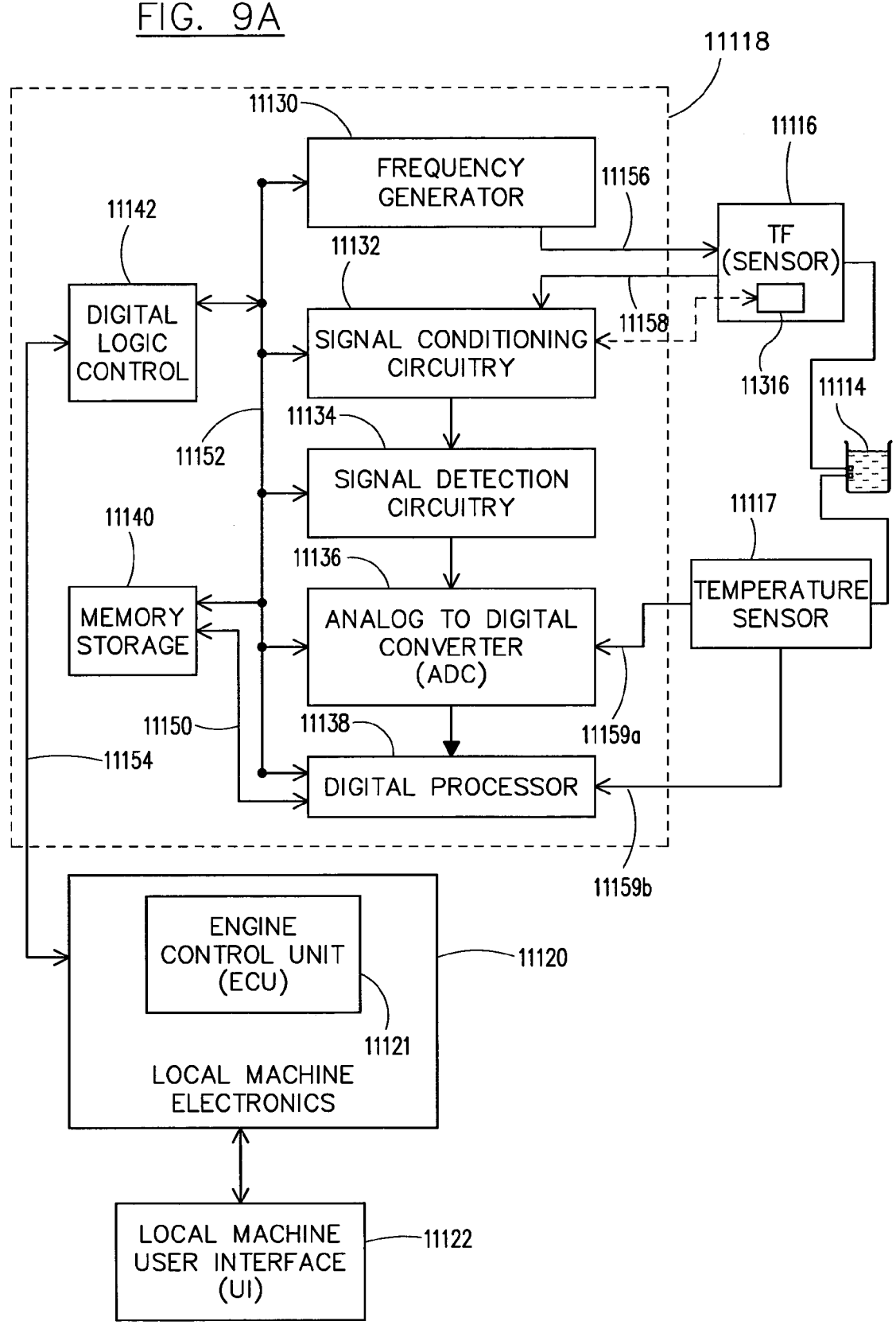

FIG. 9A illustrates a block diagram of the circuit formed, for example, in an application specific integrated circuit (ASIC) 11118 and its components, as an example of a signal processing circuit. The ASIC 11118 is designed to provide stimulus to the tuning fork 116 and receive and process data to provide information regarding the characteristics of a fluid under-test. In one embodiment, the ASIC will include a frequency generator 11130 that is configured to provide a frequency stimulus to the tuning fork 11116 by way of communication line 11156. The generated frequency is preferably a variable frequency input signal, such as a sinusoidal wave or square wave, that sweeps over a predetermined frequency range. The sweeping range will preferably include the resonance frequency range of the sensor. Preferably, the frequency is less than 100 kHz, and more preferably, is in the range of about 5 kHz and about 50 kHz, and most preferably, is in the range of about 20 kHz to about 35 kHz.

The tuning fork response over the frequency range is then monitored to determine the physical and electrical properties of the fluid under-test. The response from the tuning fork 11116 is provided to a signal conditioning circuitry block 11132, by way of a communication line 11158. In one preferred embodiment, the tuning fork 11116 will also include a capacitor 11316, which will be described in greater detail below. The capacitor 11316 is also coupled to the signal conditioning circuitry 11132. The signal conditioning circuitry 11132 is provided to receive the analog form of the signal from the tuning fork 11116 and condition it so that more efficient signal processing may be performed before further processing.

The signal conditioning circuitry 11132 will receive the analog output from the tuning fork 11116, and is designed to substantially eliminate or reduce signal offsets, thus increasing the dynamic range of the signal that is to be further processed. In this manner, further processing can concentrate on the signal itself as opposed to data associated with the signal offset.

Signal detection circuitry (SDC) 11134 is also provided, and it is coupled to the signal conditioning circuitry 11132. Signal detection circuitry 11134 will include, in one embodiment, a root mean squared (RMS) to DC converter, that is designed to generate a DC output (i.e., amplitude only) equal to the RMS value of any input received from the signal conditioning circuitry 11132. The functional operation of a RMS-to-DC converter is well known to those skilled in the art. In another embodiment, the signal detection circuitry 11134 may be provided in the form of a synchronous detector. As is well known, synchronous detectors are designed to identify a signal's phase and amplitude when preprocessing of an analog signal is desired in order to convert the analog signal into digital form. Once the signal detection circuitry block 11134 processes the signal received from the signal conditioning circuitry 11132, the signal detection circuitry 11134 will pass the data to an analog-to-digital converter (ADC) 11136. The analog-to-digital converter 11136 will preferably operate at a sampling rate of up to 10 kHz while using a 10-bit resolution. The analog-to-digital converter (ADC) can, of course, take on any sampling rate and provide any bit resolution desired so long as the data received from the signal detection circuitry is processed into digital form.

The ADC 11136 will also receive information from the temperature sensor 11117 to make adjustments to the conversion from the analog form to the digital form in view of the actual temperature in the fluid under-test 11114. In an alternative embodiment, the temperature sensor 11117 can be omitted, however, the temperature sensor 11117 will assist in providing data that will expedite the processing by the ASIC 11118.

The digital signal provided by the analog-to-digital converter 11136 is then forwarded to a digital processor 11138. The digital processor 11138 is coupled to memory storage 11140 by way of a data bus 11150 and a logic bus 11152. Logic bus 11152 is also shown connected to each of the frequency generator 11130, the signal conditioning circuitry 11132, the signal detection circuitry 11134, and the analog-to-digital converter 11136. A digital logic control 11142 is directly coupled to the logic bus 11152. The digital logic control 11142 will thus communicate with each of the blocks of the ASIC 11118 to synchronize when operation should take place by each one of the blocks. Returning to the digital processor 11138, the digital processor 11138 will receive the sensed data from the tuning fork 11116 in digital form, and then apply an algorithm to identify characteristics of the fluid under-test 11114.

The algorithm is designed to quickly identify variables that are unknown in the fluid under-test. The unknown variables may include, for example, density, viscosity, the dielectric constant, and other variables (if needed, and depending on the fluid). Further, depending on the fluid under-test 11114 being examined, the memory storage 11140 will have a database of known variables for specific calibrated tuning forks. In one embodiment, the memory storage 11140 may also hold variables for approximation of variables associated with particular fluids. In another embodiment, the memory storage 11140 will store serial numbers (or some type of identifier) to allow particular sets of data to be associated with particular tuning forks. In such a serial number configuration, the storage memory can hold unique data sets for a multitude of unique tuning forks. When a tuning fork is sold, for example, the purchaser need only input its assigned serial number into an interface, and the data set associated for that tuning fork will be used during operation. From time to time, it may be necessary to upload additional data sets to the storage memory 11140, as new tuning forks (with unique serial numbers) are manufactured.

The process for using variable data from prior calibrations and from fluids that may closely resemble the fluid under-test, will be described in greater detail below. In general, however, the digital processor 11138 may quickly access the data from the memory storage 11140, and digitally process an algorithm that will generate and output variables that define the fluid under-test 11114.

The digital processor will then communicate through the digital logic control 11142 and communication line 11154, the identified variables that characterize the fluid under-test 11114 to the local machine electronics 11120 (or some recipient computer, either locally or over a network). In one embodiment, the local machine electronics 11120 will include an engine control unit (ECU) 11121, that directly receives the data from the digital logic control 11142 through signal 11154. The engine control unit 11121 will then receive that data and, in accordance with its programmed routines, provide feedback to the local machine user interface 11122.

For example, the engine control unit 11121, may set a different threshold for when the fluid under-test 11114 (i.e., engine oil), has degraded. For example, different car manufacturers, and therefore, different engine control units for each car will define a particular viscosity, density and dielectric constant (or one or a combination thereof) that may be indicative of a need to change the oil. However, this programmable threshold level setting will differ among cars. Thus, the engine control unit 11121 will provide the local machine user interface 11122 the appropriate signals depending on the programming of the particular automobile or engine in which the engine control unit 11121 is resident.

The ASIC 11118 has been shown to include a number of component blocks, however, it should be understood that not all components need be included in the ASIC as will be discussed below. In this example, the digital processor 11138 may be physically outside of the ASIC 11118, and represented in terms of a general processor. If the digital processor 11138 is located outside of the ASIC 11118, the digital logic control 142 will take the form of glue logic that will be able to communicate between the digital processor 11138 that is located outside of the ASIC 11118, and the remaining components within the ASIC 11118. In the automobile example, if the processor 11138 is outside of the ASIC, the processor will still be in communication with the engine control unit 11121.

Figure 9B:
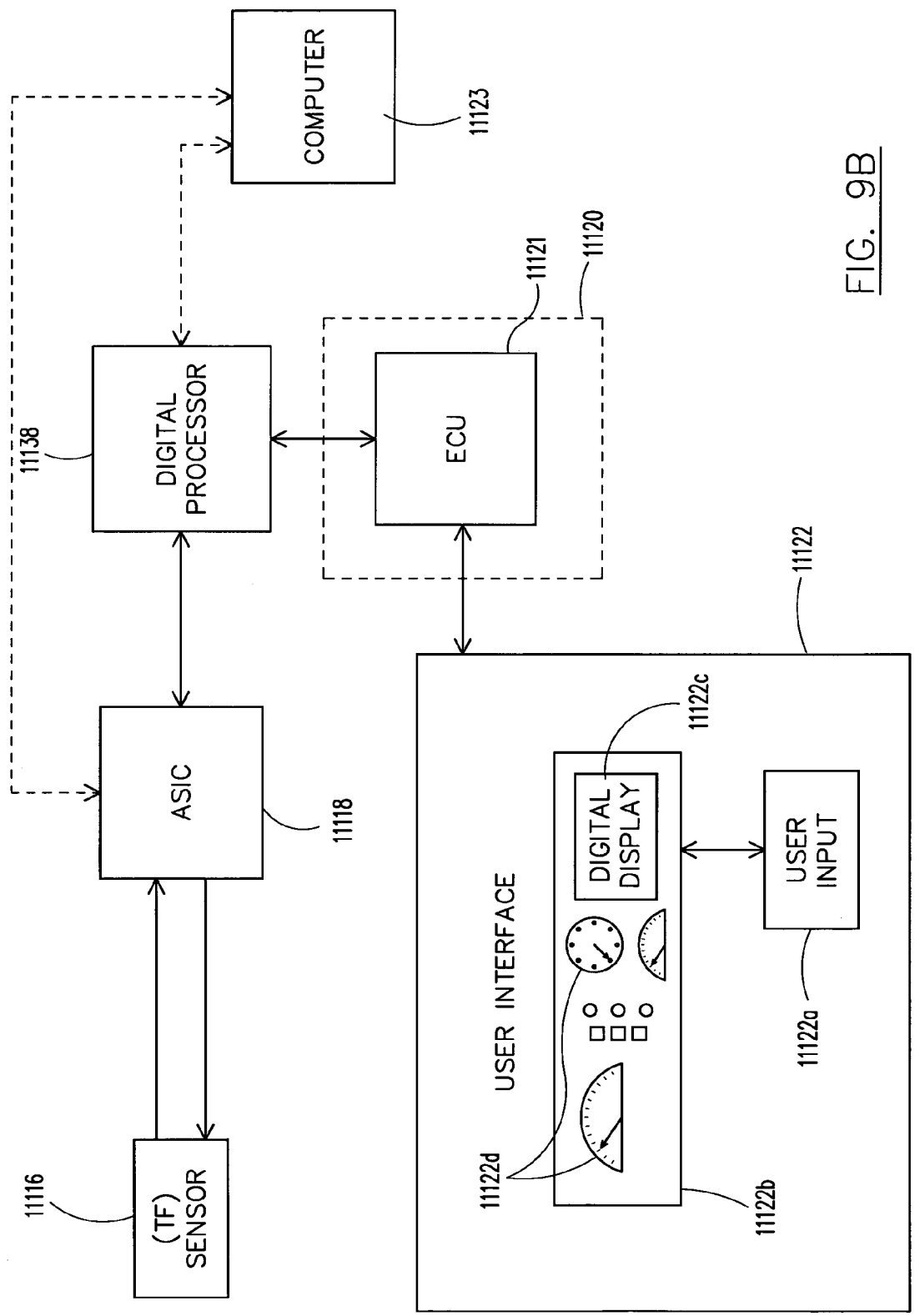

FIG. 9B illustrates an example when the digital processor 11138 is outside of the ASIC 11118. In such an embodiment, the digital processor 11138 may be integrated into a printed circuit board that is alongside of the ASIC 11118, or on a separate printed circuit board. In either case, the ASIC 11118 will be in communication with the tuning fork 11116 to provide stimulus and to process the received analog signals from the tuning fork 11116. The ASIC will therefore convert the analog signals coming from the tuning fork 11116 and convert them to a digital form before being passed to the digital processor 11138.

If the ASIC 11118 is provided on an automobile, and the digital processor 138 is outside of the ASIC 11118, the digital processor 11138 will still be able to communicate with the engine control unit 11121 of the local machine electronics 11120. The engine control unit 11121 will therefore communicate with the local machine user interface 11122. In this example, the user interface may include a user display 11122b. The user display 11122b may include analog and digital indicators 11122d. The analog and digital indicators 11122d may indicate the qualities of the fluid under-test (e.g., engine oil), and can be displayed in terms of a gauge reading to indicate to the user when the fluid under-test has degraded or needs to be changed.

In another embodiment, the user display 11122b may include a digital display 11122c (e.g., monitor) that may provide a digital output or display of the condition of the engine oil to the user through an appropriate graphical user interface (GUI). The user interface 11122 may also include a user input 11122a. The user input 11112a may be a electronic interface that would allow a service technician, for example, to provide updated calibration information for a tuning fork that is inserted in a particular vehicle, or provide adjusted approximations for new engine oils that may just have come onto the market.

By way of the user input 11122a, a service technician will be able to input new data to the ASIC 11118 through the engine control unit 11121. As mentioned above, the ASIC 11118 will include a memory storage 11140 for storing calibration data, and in some embodiments, storing approximated characteristics for fluids that may undergo sensing by tuning fork 11116.

Figure 9C:
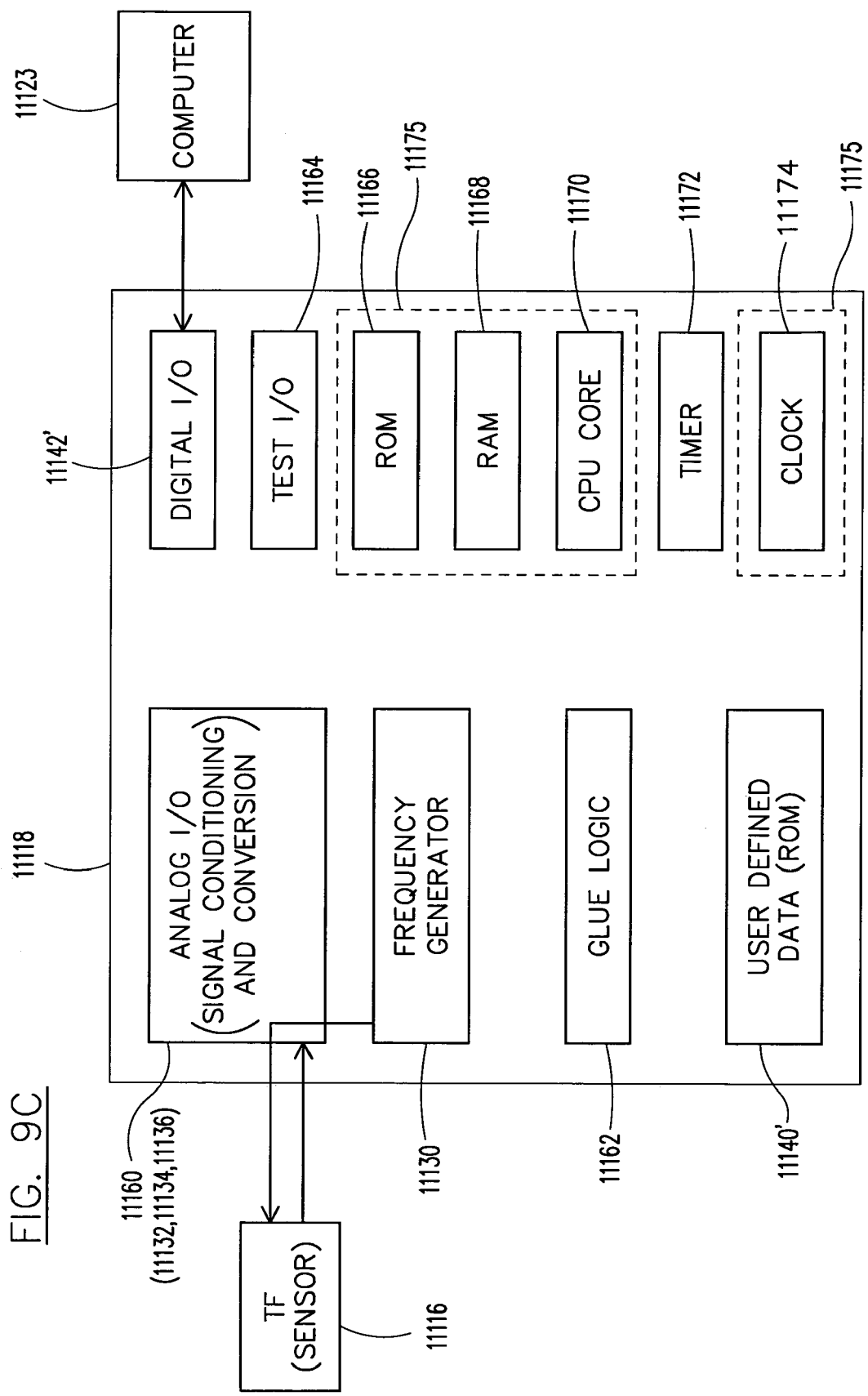
Figure 10A:
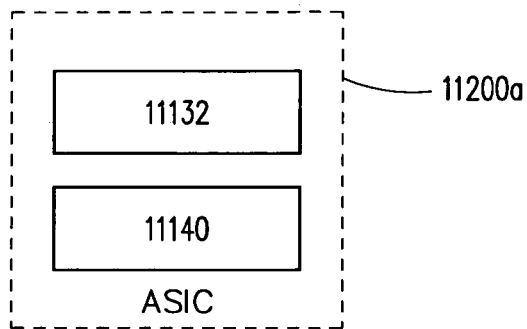
FIGS. 10A through 10D are schematic representations of alternative approaches for realizing circuitry in an ASIC.
Figure 10B:
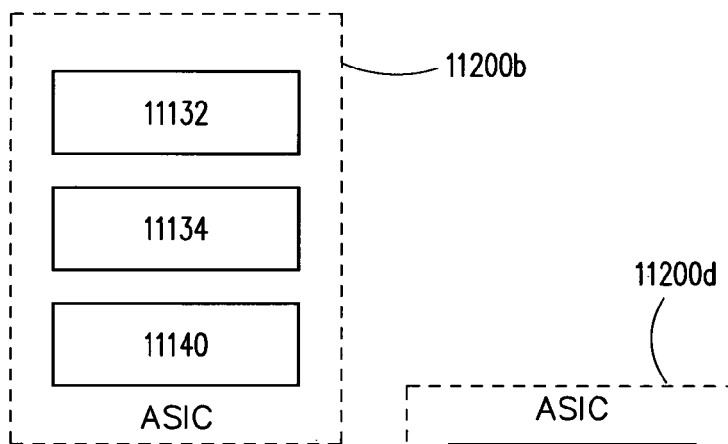
Figure 10C:
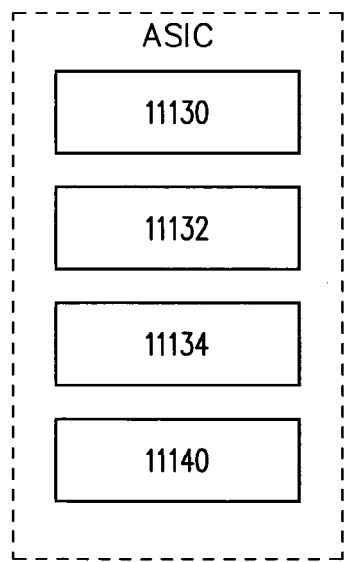
Figure 10D:
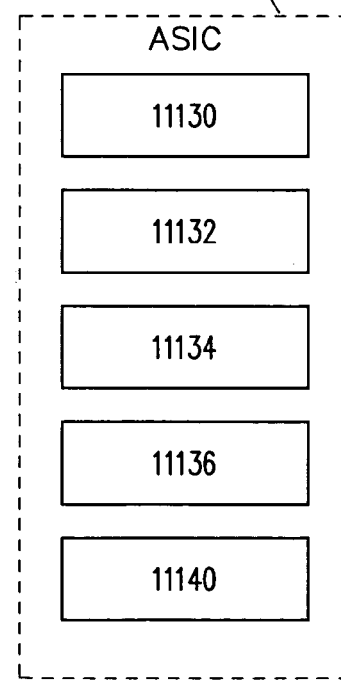

FIG. 9C illustrates another detailed block diagram of the ASIC 11118, in accordance with one embodiment of the present invention. In this example, the ASIC 11118 shows a number of blocks that may be integrated into or kept out of, the ASIC 11118. Blocks that may be kept outside of the ASIC include blocks 11175. As a high level diagram, the tuning fork 11116 is connected to an analog I/O 11160. The analog I/O is representative of blocks 11132, 11134, and 11136, in FIG. 9A above. The analog I/O block 11160 therefore performs signal conditioning and conversion of the data received from the tuning fork 11116.

Frequency generator 11130, as discussed above, will provide the variable frequency input signal to the tuning fork 11116 through the analog I/O 160. Glue logic 11162 is provided to integrate together the various circuit blocks that will reside on the ASIC 11118. As is well known, glue logic will include signaling lines, interfacing signals, timing signals, and any other circuitry that is needed to provide inputs and outputs to and from the chip that defines the ASIC 11118. All such glue logic is standard and is well known in the art. The ASIC 11118 further includes user defined data (ROM) 11140'. As mentioned above, the user-defined data 11140' may include calibration data, as well as approximated variable data for particular fluids that may become fluids under-test. The user defined data to be stored in this memory can come from any source. For example, the data may be obtained from a fluid manufacturer, a tuning fork manufacturer, a contractor party, etc. Still further, the data may be obtained in the form of a data stream, a database or over a network.

For example, FIGS. 9D and 9E provide exemplary data that may be stored within the user-defined data 11140'. As shown in FIG. 9D, a tuning fork 1.1 (designated as such to emphasize varieties in tuning forks) may provide calibration variables, as well as approximated fluid characteristics for a particular type of fluid. In the example of FIG. 9D, the selected oil type 3 has approximated fluid characteristics for density, viscosity, and dielectric constant for a particular temperature, which is depicted in this figure to be 25° C. As used herein, the term "approximated fluid characteristics" represent starting point values of fluid characteristics before the fitting algorithm is started. The starting point values are initial values defined from experience, previous tests, or educated guesses. Consequently, the starting point values, in one embodiment, approximate the actual fluid characteristic values of the fluid under-test. In this manner, convergence to the actual fluid characteristics can be expedited.

In still another embodiment, it may be possible to start with the approximated fluid characteristics at some set of fixed values (which can be zero, for example). From each fixed value, the fitting algorithm can move the value until the actual fluid characteristic value is ascertained.

Continuing with the example, the approximated fluid characteristics for the same oil type 3 may have different approximated fluid characteristics due to the rise in temperature to 40° C., in FIG. 9E. The calibration variables will also be updated to reflect the values for a particular temperature for the tuning fork 1.1. As new oil types become available to the market, it may be necessary to update the approximated fluid characteristics for the different temperature ranges so that the user-defined data can be updated in the ASIC 11118.

Referring back to FIG. 9C, a digital I/O 11140' is provided to interface with a computer 11123, and a test I/O interface 11164 is provided to enable testing of the ASIC 11118 during design simulation, during test bench testing, during pre-market release, and during field operation. The ASIC 11118 will also include a timer 11172 to provide coherent operation of the logic blocks contained in ASIC 11118. As mentioned above, the ROM block 11166, the RAM block 11168, the CPU core 11170, and the clock 11174, can optionally be included in the ASIC 11118 or removed and integrated outside of the ASIC 11118. The ROM 11166 will include programming instructions for circuit interfaces and functionality of the ASIC 11118, the RAM 11168 will provide the CPU core 11170 with memory space to read and write data being processed by the CPU core 11170, and the clock 11174 will provide the ASIC with proper signal alignment for the various signals being processed by the blocks of the ASIC 11118.

FIGS. 10A through 10D depict alternative configurations for various circuit modules of the ASIC 11118.

General Schema Re Data Collection for Complex Arrangements

The methods and systems and apparatus of the invention can be used to monitor fluidic systems for various purposes. The inventions can be advantageously used, for example, to monitor fluids in any of a number of field applications, as discussed previously, and in further detail below. Use of the methods and systems and apparatus can be also generally described, for example, with regard to preferred data architecture schema. Such schema are generally applicable to a variety of specific end-use applications. The following discussion illustrates some preferred schema, and illustrate the significant advantages that can be realized using the methods and apparatus of the present invention.

Figure 11A:
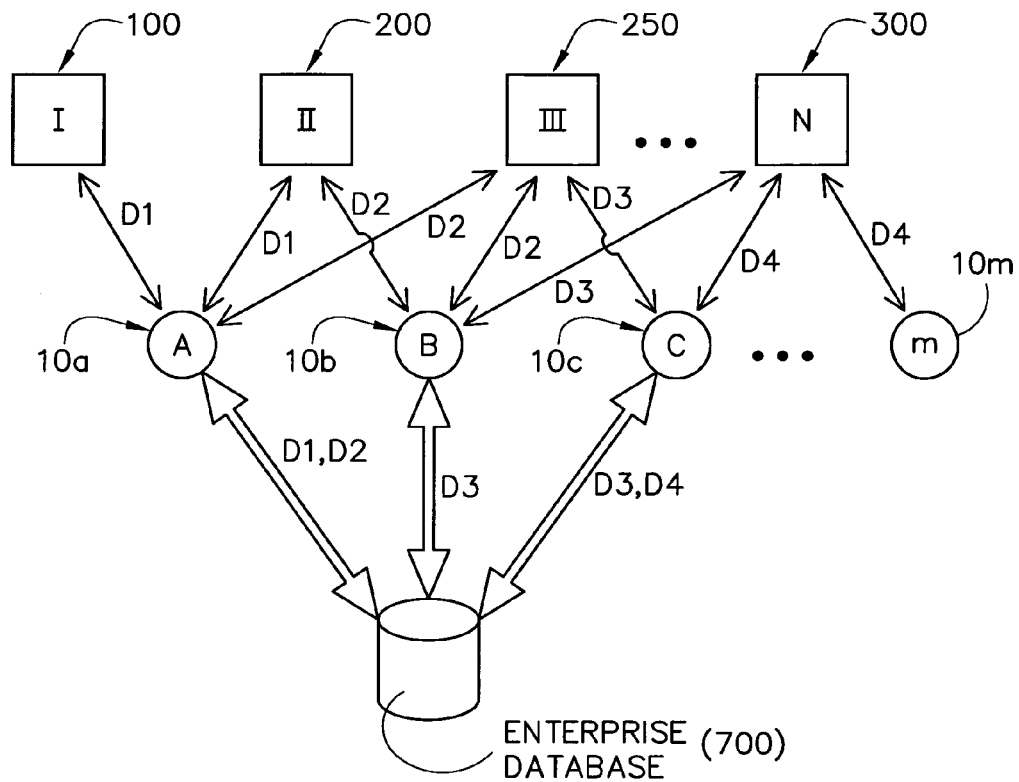
FIGS. 11A through 11D are schematic representations of various schema for advantageously using the methods, apparatus and systems of the inventions for generating data associated with one or more properties of fluids in a plurality of fluidic systems, and for warehousing such generated data (or a selected subset thereof) in one or more common database (e.g., as a remote data repository).
Figure 11B:
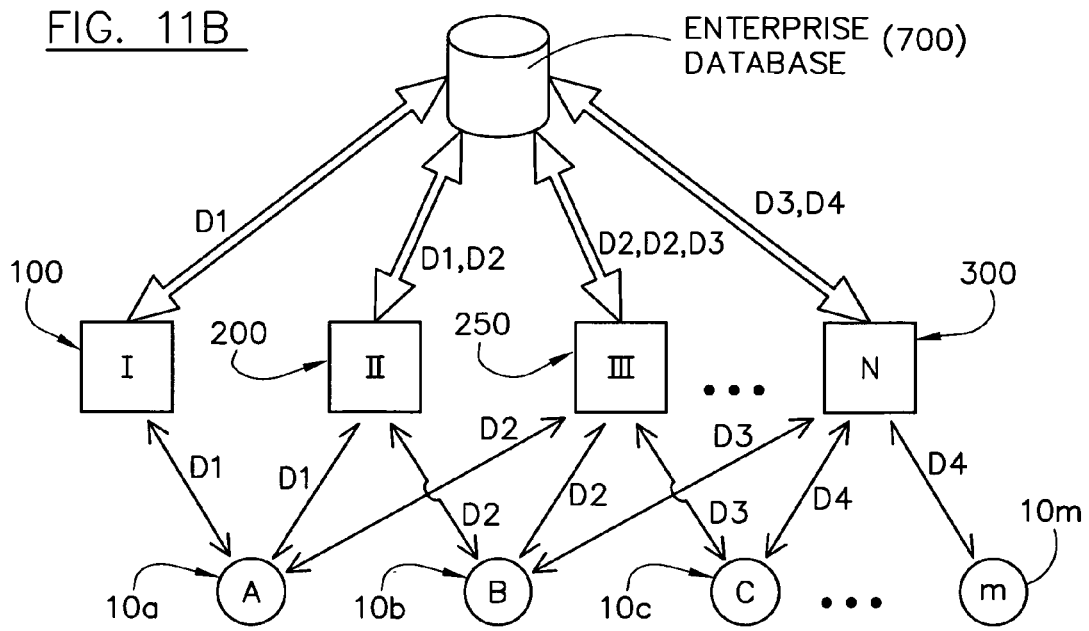

With reference to FIGS. 11A and 11B, for example, a plurality of ported units (e.g., ported sensors (not shown) or ported sensor subassemblies shown as 10a, 10b, 10c, . . . 10m, labeled as A, B, C, . . . m, respectively) can be interfaced with a plurality of fluidic systems 100, 200, 250, . . . 300, labeled as I, II, III, . . . N. As shown in these figures, ported unit A can be in the possession of a first service technician and can be interfaced sequentially in time (e.g., over a first series of days) with: fluidic system I (e.g., on day 1 labeled as D1), fluidic system II (e.g., on day 2 labeled as D2). Ported unit B can be in the possession of a second service technician and can also be interfaced sequentially in time (e.g., over a second series of days) with: fluidic system II (e.g., on day 2 labeled as D2), fluidic system III (e.g., at a later time on day 2 labeled as D2), and with fluidic system N (e.g., on day 3 labeled as D3). Ported unit C can be in the possession of a third service technician and can be interfaced sequentially in time (e.g., over a series of days) with: fluidic system III (e.g., on day 3 labeled as D3) and then with fluidic system N (e.g., on day 4 labeled as D4). Ported unit m can be in the possession of an $m^{th}$ service technician and can be interfaced sequentially in time (e.g., over a series of days) with one or more fluidic systems, such as shown with fluidic system N (e.g., on day 4 labeled as D4). In the schema depicted in FIG. 11A, each of the ported units 10a, 10b, 10c, 10m can comprise a data retrieval circuit that comprises a data transmission circuit that allows for efficient regular electrical communication of data with a central common database 700 (e.g., located on a central server) of an enterprise. This schema may be particularly advantageous where the fluidic systems I, II, III . . . N are monitored at widely disparate locations across a substantial geographical distance—where direct local communications between the fluidic systems and a central database would be impractical. In the schema depicted in FIG. 11B, however, efficient electrical communications may alternatively be regularly effected using a data transmission circuit installed within each of the fluidic systems I, II, III . . . N in electrical communication with the central common database 700 of the enterprise. This schema may be advantageous applied where the fluidic systems I, II, III . . . N are situated within a distance where direct local communications between the fluidic systems and a central database would be practical.

In either of the aforementioned schema, the central database 700 can act as a remote data repository for the enterprise, for collecting and recording data collected by different people, on different systems at different times. The central database 700 can likewise act as a source of data for downstream data processing (e.g., use in a process control system, and/or use in tracking trends in fluidic system operations, and/or use in planning and/or scheduling maintenance to a fluidic system, etc.), and/or in research or development activities. Further downstream processing activities are discussed herein above, and in greater detail hereinafter.

Figure 11C:
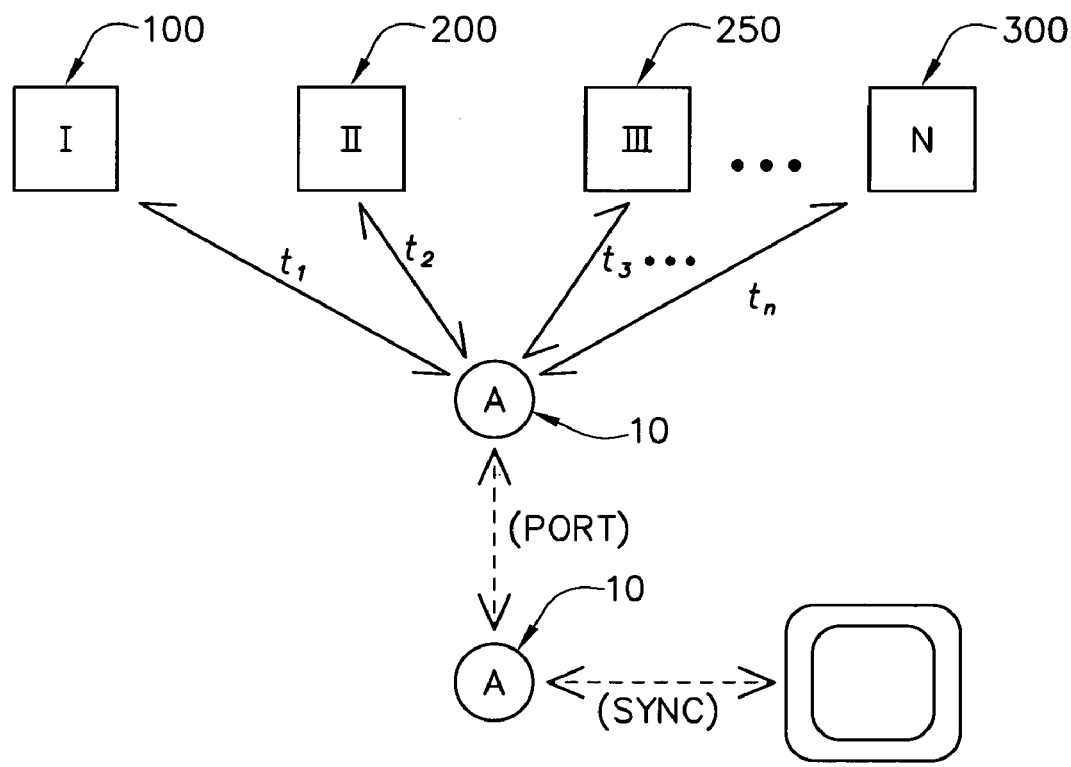

Another generally applicable schema, depicted in FIG. 11C, may be more effective for smaller enterprise operations, such as for small business operators servicing fluidic systems. One or more ported units (e.g., ported sensors (not shown) or ported sensor subassemblies shown as a single unit 10, labeled as A can be sequentially interfaced with a plurality of fluidic systems 100, 200, 250, . . . 300, labeled as I, II, III, . . . N. As shown in this figure, ported unit A can be in the possession of a service technician and can be interfaced sequentially in time with: fluidic system I (e.g., at time 1 labeled as t1), fluidic system II (e.g., at time 2 labeled as t2), fluidic system III (e.g., at time 3 labeled as t3), and then at fluidic system N (e.g., at time n labeled as tn). In this schema, the ported unit 10 can comprise a data retrieval circuit (e.g., such as a data storage circuit) that allows for data collection in the field at various times at various fluidic systems, and allows for later (e.g., same day or later day) porting of the ported unit having the collected data back to a central office. The ported unit 10 can also comprise a data transmission circuit configured to allow for electrical communication of the collected data with a personal computer 710 acting as a common database 700 (e.g., via synchronization protocols, such as can be effected using Palm™ Operating System or similar data transfer protocols). This schema may be particularly advantageous for smaller business enterprises desiring less capital expenditure for infrastructure, but needing to monitor fluidic systems I, II, III . . . N at disparate locations and at different times.

Figure 11D:
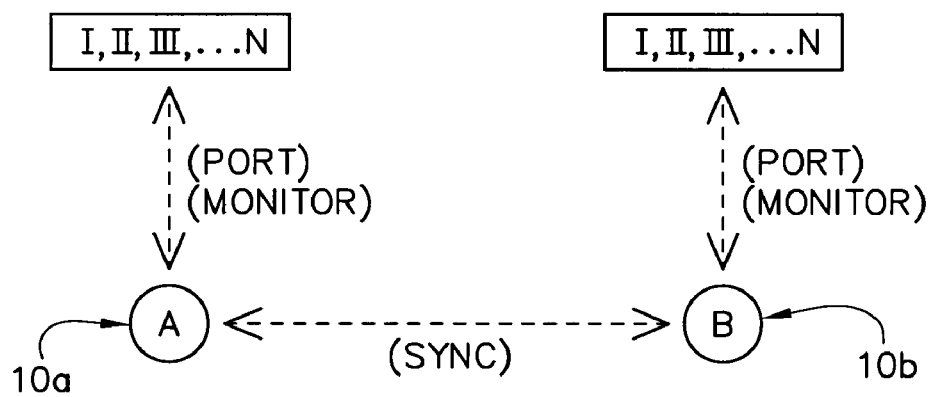

A further generally applicable schema, depicted in FIG. 11D, may be effectively applied by itself and/or in combination with one or more of the aforementioned schema. FIG. 11D shows a "unit-to-unit" data sharing schema, in which a first ported unit (e.g., a ported sensor (not shown) or a ported sensor subassemblies shown as 10a, labeled as A) and a second ported unit (e.g., a ported sensor (not shown) or a ported sensor subassemblies shown as 10b, labeled as B) can be independently operated (e.g., to monitor different fluidic systems at different times). Each of the ported units 10a, 10b can comprise a data retrieval circuit (e.g., such as a data storage circuit) that allows for data collection in the field at various times at various fluidic systems, as well as a data transmission circuit configured to allow for electrical communication of the collected data with another ported unit 10a, 10b. Advantageously, such unit-to-unit data sharing schema allows for substantial flexibility in field monitoring operations.

In general in the methods and systems and apparatus of the inventions, including in connection with the general schema outlined above, the number of subassemblies m included within the plurality of ported units (e.g., ported sensors or ported sensor subassemblies) is not critical, but can advantageously include four or more, preferably eight or more, preferably fifteen or more, preferably twenty-five or more, preferably forty or more, preferably seventy or more, or preferably one-hundred or more. Likewise, in general, the number of fluidic systems N included within the plurality of fluidic systems is not critical, but can advantageously include four or more, preferably eight or more, preferably fifteen or more, preferably twenty-five or more, preferably forty or more, preferably seventy or more, or preferably one-hundred or more. The number of ported units can be the same or different from the number of fluidic systems.

Downstream Data Processing

The methods and systems and apparatus of the invention can be used as described herein to monitor fluids in fluidic systems to generate data associated with one or more properties of the fluids. The data generated can be used directly, for example, as described herein for status evaluation, fluid property logging, fluid property tracking, etc., among other uses. Such data can also be subsequently further processed for further subsequent uses (i.e., downstream) for various purposes. Such downstream processing of the data or data stream (represented for example by a signal or signal stream), typically but not necessarily in connection with other data from other independent sources, can be effectively applied to generate higher level information or knowledge based on the directly generated data, for example for purposes such as one or more of: process monitoring, process control (e.g., involving automated or manual control schemes, such as feedback or feed forward control schemes), fluid maintenance (e.g., fluid replacement (whole or partial), fluid enhancement (e.g., adding one more additives or removing one or more contaminants), fluid operating conditions (e.g., temperature, pressure, flowrate, etc.), predictive maintenance, materials or process research, materials or process development, quality control, fluid analysis, and especially maintenance or service applications involving any of the foregoing, among others.

Specific End-Use Applications

The methods and systems and apparatus of the invention can be used to monitor fluidic systems for various purposes. The inventions can be advantageously used, for example, to monitor fluids in any of the field applications and/or fluidic systems and/or fluid types as shown in FIGS. 12A through 12C.

Particularly preferred applications involve heating, ventilating, air conditioning and refrigeration (HVAC&R) applications. In these applications, the fluidic systems can include circulating fluids such as circulating refrigerants, circulating coolants, circulating lubricants and circulating oils. In general, many fluids used in HVAC&R fluidic systems can be collectively referred to as thermal change fluids—fluids which have a thermal property change within the fluidic system, for example, typically within each cycle of a fluidic system, including for example, changes due to one or more unit operations (e.g., fluid compression, fluid expansion, heat transfer, etc.). Hence, a thermal change fluid can include: refrigerants, coolants, lubricants, oils and mixtures thereof. For example, coolant being compressed in an HVAC&R fluidic system can include compressor lubricant or oil. Also, the engines driving such compressors or other devise can have their own isolated fluidic systems (e.g., circulating oil fluidic system).

Transportation vehicles are also particularly preferred.

Fluidic systems in heavy machinery, such as engines and compressors are also particularly preferred.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. An apparatus for use in monitoring a property of a fluid in a fluidic system, the apparatus comprising
   a plug adapted for removable engagement with the fluidic system, and
   a flexural resonator mounted on a first surface of the plug and having a sensing surface for contacting the fluid,
   the plug being adapted for electrical communication between the flexural resonator and one or more of a signal processing circuit, or a data retrieval circuit,
   one or more conductive paths extending through the plug and providing electrical communication between the flexural resonator and one or more contacts on a second surface of the plug, such that a removable sensor subassembly can be interfaced with the flexural resonator through the one or more contacts, and
   a temperature sensor mounted on the first surface of the plug, and one or more conductive paths extending through the plug and providing electrical communication between the temperature sensor and one or more contacts on the second surface of the plug.

2. The apparatus of claim 1, wherein the removable sensor subassembly comprises a signal processing circuit in electrical communication with the flexural resonator.

3. The apparatus of claim 2, wherein the removable sensor subassembly further comprises a data retrieval circuit in electrical communication with the signal processing circuit.

4. The apparatus of claim 1, wherein the removable sensor subassembly further comprises a data retrieval circuit in electrical communication with the flexural resonator.

5. An apparatus for use in monitoring a property of a fluid in a fluidic system, the apparatus comprising
   a structure supporting a fluid filter and adapted for engagement with the fluidic system, and
   a flexural resonator mounted on or integrated with the support structure and having a sensing surface for contacting the fluid,
   the support structure being adapted for providing electrical communication between the flexural resonator and a data retrieval circuit,
   one or more conductive paths providing electrical communication between the flexural resonator and one or mare contacts on an accessible surface of the support structure, such that a removable sensor subassembly can be interfaced with the flexural resonator through the one or more contacts
   a temperature sensor mounted on or integrated with the support structure, and the one or more conductive paths providing electrical communication between the temperature sensor and the one or more contacts the accessible surface of the support structure.

6. The apparatus of claim 5, wherein the removable sensor subassembly comprises a signal processing circuit in electrical communication with the flexural resonator.

7. The apparatus of claim 6, wherein the removable sensor subassembly further comprises a data retrieval circuit in electrical communication with the signal processing circuit.

8. The apparatus of claim 5, wherein the removable sensor subassembly further comprises a data retrieval circuit in electrical communication with the flexural resonator.

* * * * *